US011952421B2

(12) United States Patent
Vu et al.

(10) Patent No.: US 11,952,421 B2
(45) Date of Patent: Apr. 9, 2024

(54) BISPECIFIC ANTIBODIES AGAINST CD3EPSILON AND ROR1

(71) Applicant: BRISTOL-MYERS SQUIBB COMPANY, Princeton, NJ (US)

(72) Inventors: Minh Diem Vu, Wollerau (CH); Klaus Strein, Weinheim (DE); Oliver Ast, Bassersdorf (CH); Tanja Fauti, Zurich (CH); Anne Freimoser-Grundschober, Zurich (CH); Ralf Hosse, Cham (CH); Christian Klein, Bonstetten (CH); Ekkehard Moessner, Kreuzlingen (CH); Samuel Moser, Rotkreuz (CH); Ramona Murr, Zurich (CH); Pablo Umana, Wollerau (CH); Sabine Jung-Imhof, Planegg (DE); Stefan Klostermann, Neuried (DE); Michael Molhoj, Munich (DE); Joerg Regula, Munich (DE); Wolfgang Schaefer, Mannheim (DE)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/517,296

(22) PCT Filed: Oct. 8, 2015

(86) PCT No.: PCT/EP2015/073308
§ 371 (c)(1),
(2) Date: Apr. 6, 2017

(87) PCT Pub. No.: WO2016/055592
PCT Pub. Date: Apr. 14, 2016

(65) Prior Publication Data
US 2017/0306018 A1 Oct. 26, 2017

(30) Foreign Application Priority Data

Oct. 9, 2014 (EP) .................................... 14188378
Oct. 14, 2014 (EP) .................................... 14188727

(51) Int. Cl.
*A61K 39/00* (2006.01)
*C07K 16/28* (2006.01)

(52) U.S. Cl.
CPC ...... *C07K 16/2809* (2013.01); *C07K 16/2803* (2013.01); *A61K 2039/505* (2013.01); *C07K 2317/31* (2013.01); *C07K 2317/64* (2013.01); *C07K 2317/73* (2013.01); *C07K 2317/77* (2013.01)

(58) Field of Classification Search
CPC .............................................. A61K 3039/505
See application file for complete search history.

(56) References Cited

U.S. PATENT DOCUMENTS

| | | | |
|---|---|---|---|
| 4,816,567 | A | 3/1989 | Cabilly et al. |
| 5,202,238 | A | 4/1993 | Fell, Jr. et al. |
| 5,204,244 | A | 4/1993 | Fell et al. |
| 5,273,743 | A | 12/1993 | Ahlem et al. |
| 5,837,242 | A | 11/1998 | Holliger et al. |
| 5,837,821 | A | 11/1998 | Wu |
| 6,294,654 | B1 | 9/2001 | Bogen et al. |
| 6,303,341 | B1 | 10/2001 | Hiatt et al. |
| 6,331,415 | B1 | 12/2001 | Cabilly et al. |
| 6,551,592 | B2 | 4/2003 | Lindhofer et al. |
| 6,838,254 | B1 | 1/2005 | Hamers et al. |
| 7,150,872 | B2 | 12/2006 | Whitlow et al. |
| 7,235,641 | B2 | 6/2007 | Kufer et al. |
| 7,655,759 | B2 | 2/2010 | Hamers et al. |
| 8,212,009 | B2 | 7/2012 | Kipps et al. |
| 8,592,562 | B2* | 11/2013 | Kannan ................... A61P 37/04 530/387.3 |
| 9,228,023 | B2* | 1/2016 | Rohlff .................. C07K 16/005 |
| 9,963,513 | B2 | 5/2018 | Vu et al. |
| 10,077,315 | B2 | 9/2018 | Vu et al. |
| 10,233,237 | B2* | 3/2019 | Kannan ............. C07K 16/2863 |
| 10,253,104 | B2 | 4/2019 | Vu et al. |
| 10,683,369 | B2 | 6/2020 | Vu et al. |
| 10,851,171 | B2 | 12/2020 | Vu et al. |
| 10,968,276 | B2 | 4/2021 | Moore et al. |
| 11,124,577 | B2 | 9/2021 | Vu et al. |
| 2008/0181890 | A1 | 7/2008 | Lazar et al. |
| 2008/0227958 | A1 | 9/2008 | Thompson et al. |
| 2009/0148438 | A1 | 6/2009 | Nuttal et al. |
| 2012/0282177 | A1 | 11/2012 | Rohlff et al. |
| 2013/0078249 | A1* | 3/2013 | Ast ....................... C07K 16/468 424/136.1 |
| 2013/0251642 | A1 | 9/2013 | Rader et al. |
| 2013/0251723 | A1 | 9/2013 | Rohlff et al. |

(Continued)

FOREIGN PATENT DOCUMENTS

EP 0307434 3/1989
EP 1870459 A1 12/2007

(Continued)

OTHER PUBLICATIONS

Shaefer et al. (Proc. Natl. Acad. Sci. USA. Jul. 5, 2011; 108 (27): 11187-92).*
Kontermann et al. (MAbs. Mar.-Apr. 2012; 4 (2): 182-97).*
Zhang et al. (Sci. Rep. Jul. 24, 2014; 4: 5811; pp. 1-7).*
Fenn et al. (PLoS One. 2013; 8 (4): e61953; electronically published Apr. 17, 2013; pp. 1-7).*
Schaefer et al. (Proc. Natl. Acad. Sci. USA. Jul. 5, 2011; 108 (27): 11187-92).*
Bönisch et al. (Nat. Biotechnol. Feb. 2014; 32 (2): 191-8).*
Lewis et al. (Nat. Biotechnol. Feb. 2014; 32 (2): 191-8).*
Mezzanzanica D. et al : 11 Human Ovarian Carcinoma Lysis by Cytotoxic T Cells Targeted by Bispecific Monoclonal Antibodies : Analysis of the Antibody Components 11 , International Journal of Cancer, John Wiley & Sons, Inc, US, vol. 41, No. 4, Jan. 1, 1988, (Jan. 1, 1988) , pp. 609-615.

(Continued)

*Primary Examiner* — Stephen L Rawlings
(74) *Attorney, Agent, or Firm* — Jones Day

(57) ABSTRACT

The present invention relates to bispecific antibodies against ROR1 and CD3, their manufacture and use.

6 Claims, 24 Drawing Sheets

Specification includes a Sequence Listing.

(56) References Cited

U.S. PATENT DOCUMENTS

| | | | |
|---|---|---|---|
| 2014/0154254 A1* | 6/2014 | Kannan | C07K 16/468 424/136.1 |
| 2014/0242079 A1 | 8/2014 | Bacac et al. | |
| 2014/0370020 A1 | 12/2014 | Kuramochi et al. | |
| 2015/0315296 A1* | 11/2015 | Schaefer | C07K 16/22 424/136.1 |
| 2016/0046705 A1* | 2/2016 | Kannan | A61P 19/00 424/130.1 |
| 2016/0075785 A1* | 3/2016 | Ast | C07K 16/32 424/136.1 |
| 2016/0297881 A1 | 10/2016 | Vu et al. | |
| 2017/0204199 A1* | 7/2017 | Sanches | C07K 16/32 |
| 2017/0306033 A1* | 10/2017 | Kannan | C07K 16/2869 |
| 2017/0306036 A1* | 10/2017 | Vu | C07K 16/2809 |
| 2017/0327580 A1 | 11/2017 | Vu et al. | |
| 2019/0153086 A1* | 5/2019 | Kannan | C07K 16/22 |
| 2019/0352427 A1 | 11/2019 | Vu et al. | |
| 2020/0231673 A1* | 7/2020 | Ast | A61P 35/00 |
| 2020/0255521 A1 | 8/2020 | Vu et al. | |
| 2020/0283545 A1 | 9/2020 | Vu et al. | |
| 2020/0385471 A1 | 12/2020 | Vu et al. | |
| 2021/0070873 A1 | 3/2021 | Vu et al. | |
| 2022/0002427 A1 | 1/2022 | Vu et al. | |
| 2022/0017631 A1 | 1/2022 | Vu et al. | |
| 2023/0057602 A1 | 2/2023 | Burgess et al. | |
| 2023/0172923 A1 | 6/2023 | Jeyaraju et al. | |

FOREIGN PATENT DOCUMENTS

| | | | |
|---|---|---|---|
| EP | 2647707 A1 | 10/2013 | |
| EP | 2789630 A1 * | 10/2014 | A61P 35/00 |
| EP | 2787078 | 5/2019 | |
| WO | 88/07089 A1 | 9/1988 | |
| WO | 92/18149 A1 | 10/1992 | |
| WO | 95/27060 A2 | 10/1995 | |
| WO | 1996/027011 A1 | 9/1996 | |
| WO | 98/050431 A2 | 11/1998 | |
| WO | 1999/37791 A1 | 7/1999 | |
| WO | WO 2000/041474 | 7/2000 | |
| WO | 2002/44215 A2 | 6/2002 | |
| WO | 2002/087618 A1 | 11/2002 | |
| WO | 2003/014161 A2 | 2/2003 | |
| WO | 2003/025018 A2 | 3/2003 | |
| WO | 2003/048209 A1 | 6/2003 | |
| WO | 2004/058822 A2 | 7/2004 | |
| WO | 2004/076489 A1 | 9/2004 | |
| WO | 2005/016950 A1 | 2/2005 | |
| WO | 2005/040413 A1 | 5/2005 | |
| WO | 2005/100605 A1 | 10/2005 | |
| WO | 2006/072620 A1 | 7/2006 | |
| WO | 2006/093794 A1 | 9/2006 | |
| WO | 2006/113665 A2 | 10/2006 | |
| WO | WO 2007/019620 | 2/2007 | |
| WO | WO-2007042261 A2 * | 4/2007 | A61K 39/39558 |
| WO | 2007/051077 A2 | 5/2007 | |
| WO | 2007/110205 A2 | 10/2007 | |
| WO | 2007/146957 A2 | 12/2007 | |
| WO | 2007/146968 A2 | 12/2007 | |
| WO | 2007/147901 A1 | 12/2007 | |
| WO | 2008/036449 A2 | 3/2008 | |
| WO | 2008/076868 A2 | 6/2008 | |
| WO | 2008/103849 A2 | 8/2008 | |
| WO | 2008/119353 A1 | 10/2008 | |
| WO | 2008/119567 A2 | 10/2008 | |
| WO | 2009/080251 A1 | 7/2009 | |
| WO | 2009/080252 A1 | 7/2009 | |
| WO | 2009/080253 A1 | 7/2009 | |
| WO | 2009/080254 A1 | 7/2009 | |
| WO | 2009/089004 A1 | 7/2009 | |
| WO | 2009/117531 A1 | 9/2009 | |
| WO | 2010/08069 A1 | 1/2010 | |
| WO | WO 2010/037835 | 4/2010 | |
| WO | 2010/063785 A2 | 6/2010 | |
| WO | 2010/124188 A1 | 10/2010 | |
| WO | 2010/129304 A2 | 11/2010 | |
| WO | 2010/145792 A1 | 12/2010 | |
| WO | 2011/014659 A2 | 2/2011 | |
| WO | 2011/050262 A2 | 4/2011 | |
| WO | 2011/054007 A1 | 5/2011 | |
| WO | 2011/079902 A2 | 7/2011 | |
| WO | 2011/90754 A1 | 7/2011 | |
| WO | 2011/143545 A1 | 11/2011 | |
| WO | 2011/159847 A2 | 12/2011 | |
| WO | 2012/045085 A1 | 4/2012 | |
| WO | 2012/058768 A1 | 5/2012 | |
| WO | 2012/075158 A1 | 6/2012 | |
| WO | 2012/076066 A1 | 6/2012 | |
| WO | 2012/076727 A1 | 6/2012 | |
| WO | WO-2012075158 A1 * | 6/2012 | C07K 16/2857 |
| WO | 2012/097313 A2 | 7/2012 | |
| WO | 2012/116927 A1 | 9/2012 | |
| WO | 2012/130831 A1 | 10/2012 | |
| WO | 2012/131555 A2 | 10/2012 | |
| WO | WO-2012158818 A2 * | 11/2012 | A61K 39/39558 |
| WO | 2013/02362 A1 | 1/2013 | |
| WO | 2013/12733 A1 | 1/2013 | |
| WO | 2013/026839 A1 | 2/2013 | |
| WO | WO 2013/026837 | 2/2013 | |
| WO | WO-2013026839 A1 * | 2/2013 | C07K 16/468 |
| WO | 2013/096291 A2 | 6/2013 | |
| WO | 2013/157954 A1 | 10/2013 | |
| WO | WO 2013/157953 | 10/2013 | |
| WO | WO 2013/174873 | 11/2013 | |
| WO | 2014/031174 A1 | 2/2014 | |
| WO | 2014056783 A1 | 4/2014 | |
| WO | WO-2014056783 A1 * | 4/2014 | A61P 35/00 |
| WO | WO 2014/110601 | 7/2014 | |
| WO | WO 2014/122143 | 8/2014 | |
| WO | WO 2014/122144 | 8/2014 | |
| WO | 2014131712 A1 | 9/2014 | |
| WO | 2014153002 A1 | 9/2014 | |
| WO | 2014/167022 A1 | 10/2014 | |
| WO | 2014167022 A1 | 10/2014 | |
| WO | 2013065708 A1 | 4/2015 | |
| WO | WO 2016/020309 | 2/2016 | |
| WO | WO 2016/020332 | 2/2016 | |
| WO | WO 2016/055592 | 4/2016 | |
| WO | WO2016055592 A1 * | 4/2016 | |
| WO | WO 2016/087531 | 6/2016 | |
| WO | WO 2017/021450 | 2/2017 | |
| WO | WO 2018/083204 | 5/2018 | |
| WO | WO 2020/219978 | 10/2020 | |
| WO | WO 2021/092056 | 5/2021 | |
| WO | WO 2021/092060 | 5/2021 | |
| WO | WO 2021/163329 | 8/2021 | |
| WO | WO 2021/222552 | 11/2021 | |

OTHER PUBLICATIONS

International Search Report of PCT/EP2015/073308.

S. Zhang, et al., ROR1 is expressed in human breast cancer and associated with enhanced tumor-cell growth, PLoS One. 2012;7(3):e31127.

T. Yamaguchi, et al., NKX2-1/TITF1/TTF-1-Induced ROR1 is required to sustain EGFR survival signaling in lung adenocarcinoma, Cancer Cell. Mar. 20, 2012;21(3):348-61.

Dimopoulos, MA and Terpos, E., Multiple myeloma, Ann Oncol. Oct. 2010;21 Suppl 7:vii143-50.

Worn, A. and Pluckthun, A., Stability engineering of antibody single-chain Fv fragments, J Mol Biol. Feb. 2, 2001;305(5):989-1010.

Atwell, S., et al., Stable Heterodimers from Remodeling the Domain Interface of a Homodimer using a Phage Display Library, J. Mol. Biol. (1997) 270, 26-35.

Barnes, L. M., et al., Advances in animal cell recombinant protein production: GS-NS0 expression system, Cytotechnology 32: 109-123, 2000.

Barnes, L. M., et al., Characterization of the Stability of Recombinant Protein Production in the GS-NS0 Expression System, Biotechnology and Bioengineering, vol. 73, No. 4, May 20, 2001.

(56) References Cited

OTHER PUBLICATIONS

Baskar, S., et al., Targeting malignant B cells with an immunotoxin against ROR1, mAbs 4:3, 349-361; May/Jun. 2012.
Bruggemann, M, et al., Designer mice: the production of human antibody repertoires in transgenic animals, Year Immunol. 1993;7:33-40.
Brunhouse, R. and Cebra. J. J., Isotypes of IgG: comparison of the primary structures of three pairs of isotypes which differ in their ability to activate complement, Mol Immunol. Nov. 1979;16(11):907-17.
Carter, P., et al., Humanization of an anti-p185HER2 antibody for human cancer therapy, Proc Natl Acad Sci U S A. May 15, 1992;89(10):4285-9.
Daneshmanesh, A. H., et al., Ror1, a cell surface receptor tyrosine kinase is expressed in chronic lymphocytic leukemia and may serve as a putative target for therapy, Int. J. Cancer: 123, 1190-1195 (2008).
Desplancq D., et al., Multimerization behaviour of single chain Fv variants for the tumour-binding antibody B72.3, Protein Eng. Aug. 1994;7(8):1027-33.
Durocher, Y., et al., High-level and high-throughput recombinant protein production by transient transfection of suspension-growing human 293-EBNA1 cells, Nucleic Acids Res. Jan. 15, 2002;30(2):E9.
Hudecek, M., et al., The B-cell tumor-associated antigen ROR1 can be targeted with T cells modified to express a ROR1-specific chimeric antigen receptor, Blood, Nov. 25, 2010 z vol. 116, No. 22.
Kontermann, Ronald E., Dual targeting strategies with bispecific antibodies, MAbs. Mar.-Apr. 2012;4(2):182-97.
Matthias, M., et al., A small bispecific antibody construct expressed as a functional single-chain molecule with high tumor cell cytotoxicity, Proc Natl Acad Sci U S A. Jul. 18, 1995;92(15):7021-5.
Masiakowski, P. and Carroll, R. D., A novel family of cell surface receptors with tyrosine kinase-like domain, J Biol Chem. Dec. 25, 1992;267(36):26181-90.
Merchant, A. M., et al., An efficient route to human bispecific IgG, Nat Biotechnol. Jul. 1998;16(7):677-81.
Morris, S. L., et al., Variable region domain exchange influences the functional properties of IgG, J Immunol. Mar. 15, 1998;160(6):2802-8.
Neuberger, M. S., et al., A hapten-specific chimaeric IgE antibody with human physiological effector function, Nature. Mar. 21-27, 1985;314(6008):268-70.
Norderhaug, L., et al., Versatile vectors for transient and stable expression of recombinant antibody molecules in mammalian cells, J Immunol Methods. May 12, 1997;204(1):77-87.
Orlandi, R., et al., Cloning immunoglobulin variable domains for expression by the polymerase chain reaction, Proc. Natl. Acad. Sci. USA, vol. 86, pp. 3833-3837, May 1989.
Rebagay, G., et al., ROR1 and ROR2 in Human Malignancies: Potentials for Targeted Therapy, Front Oncol. Apr. 18, 2012;2:34.
Schaefer, W., et al., Immunoglobulin domain crossover as a generic approach for the production of bispecific IgG antibodies, Proc Natl Acad Sci U S A. Jul. 5, 2011;108(27):11187-92.
Schlaeger, Ernst-Jurgen, The protein hydrolysate, Primatone RL, is a cost-effective multiple growth promoter of mammalian cell culture in serum-containing and serum-free media and displays anti-apoptosis properties, J Immunol Methods. Aug. 14, 1996;194(2):191-9.
Schlaeger, Ernst-Jurgen and Christensen, Klaus, Transient gene expression in mammalian cells grown in serum-free suspension culture, Cytotechnology. Jul. 1999;30(1-3):71-83.
Topp, M. S., et al., Targeted therapy with the T-cell-engaging antibody blinatumomab of chemotherapy-refractory minimal residual disease in B-lineage acute lymphoblastic leukemia patients results in high response rate and prolonged leukemia-free survival, J Clin Oncol. Jun. 20, 2011;29(18):2493-8.
Werner, R. G., et al., Appropriate mammalian expression systems for biopharmaceuticals, Arzneimittelforschung. Aug. 1998:48(8):870-80.

Xie, Z., et al., A new format of bispecific antibody: highly efficient heterodimerization, expression and tumor cell lysis, J Immunol Methods. Jan. 2005;296(1-2):95-101.
Yang, S. Y., et al., A common pathway for T lymphocyte activation involving both the CD3-Ti complex and CD2 sheep erythrocyte receptor determinants, J Immunol. Aug. 15, 1986;137(4):1097-100.
Office Action dated Nov. 15, 2019 in corresponding Japanese Patent Application No. 2017-518525.
Bonisch et al., 2017, "Novel CH1:CL interfaces that enhance correct light chain pairing in heterodimeric bispecific antibodies," Protein Engineering, Design & Selection, 30(9):685-696.
Fenn et al., 2013, "Crystal Structures of an Anti-Ang2 CrossFab Demonstrates Complete Structural and Functional Integrity of the Variable Domain," PLoS One, 8(4): e61953.
Lewis et al., 2014, "Generation of bispecific IgG antibodies by structure-based design of an orthogonal Fab interface," Nature Biotechnology, 32(2):191-198.
Anasetti et al., 1992, "Treatment of acute graft-versus-host disease with a nonmitogenic anti-CD3 monoclonal antibody," Transplantation, 54(5):844-851.
Baskar et al., 2008, "Unique Cell Surface Expression of Receptor Tyrosine Kinase ROR1 in Human B-Cell Chronic Lymphocytic Leukemia," Clinical Cancer Research, 14(2):396-404.
Boerner et al., 1991, "Production of antigen-specific human monoclonal antibodies from in vitro-primed human splenocytes," The Journal of Immunology, 147(1):86-95.
Burton et al., 1980, "The C1q receptor site on immunoglobulin G," Nature, 288(2789):338-344.
Cain, 2011, "Crossing over to bispecificity," Science-Business eXchange, 4:783.
Cohen et al., 1972, "Nonchromosomal Antibiotic Resistance in Bacteria: Genetic Transformation of *Escherichia coli* by R-Factor DNA," Proceedings of the National Academy of Sciences, 69(8):2110-2114.
Dreier et al., 2002, "Extremely potent, rapid and costimulation-independent cytotoxic T-cell response against lymphoma cells catalyzed by a single-chain bispecific antibody," International Journal of Cancer, 100(6):690-697.
Edelman et al., 1969, "The Covalent Structure of an Entire (gamma)G Immunoglobulin Molecule," Proceedings of the National Academy of Sciences, 63(1):78-85.
Hezareh et al., 2001, "Effector Function Activities of a Panel of Mutants of a Broadly Neutralizing Antibody against Human Immunodeficiency Virus Type 1," Journal of Virology, 75(24):12161-12168.
Idusogie et al., 2000, "Mapping of the C1q Binding Site on Rituxan, a Chimeric Antibody with a Human IgG1 Fc," The Journal of Immunology, 164(8):4178-4184.
International Search Report and Written Opinion dated Jan. 19, 2016 for PCT/EP2015/073308 (11 pages).
Jakobovits et al., 1993, "Analysis of homozygous mutant chimeric mice: deletion of the immunoglobulin heavy-chain joining region blocks B-cell development and antibody production," Proceedings of the National Academy of Sciences, 90(6):2551-2555.
Kaufman, R.J., 2000, "Overview of vector design for mammalian gene expression," Molecular Biotechnology, 16:151-160.
Klein et al., 2012, "Progress in overcoming the chain association issue in bispecific heterodimeric IgG antibodies," mAbs, 4(6):653-663.
Klinger et al., 2012, "Immunopharmacologic response of patients with B-lineage acute lymphoblastic leukemia to continuous infusion of T cell-engaging CD19/CD3-bispecific BiTE antibody blinatumomab," Blood, 119(26):6226-6233.
Lukas et al., 1981, "Inhibition of C1-mediated immune hemolysis by monomeric and dimeric peptides from the second constant domain of human immunoglobulin G," The Journal of Immunology, 127(6):2555-2560.
Mack et al., 1995, "A small bispecific antibody construct expressed as a functional single-chain molecule with high tumor cell cytotoxicity," Proceedings of the National Academy of Sciences, 92(15):7021-7025.

(56) References Cited

OTHER PUBLICATIONS

Morgan et al., 1995, "The N-terminal end of the CH2 domain of chimeric human IgG1 anti-HLA-DR is necessary for C1q, Fc gamma RI and Fc gamma RIII Binding," Immunology, 86(2):319-324.

Morrison et al., 1998, "Variable region domain exchange influences the functional properties of IgG," Journal of Immunology, 160(6):2802-2808.

Morrison et al., 1984, "Chimeric human antibody molecules: mouse antigen-binding domains with human constant region domains," Proceedings of the National Academy of Sciences, 81(21):6851-6855.

Ridgway et al., 1996, "'Knobs-into-holes' engineering of antibody CH3 domains for heavy chain heterodimerization," Protein Engineering Design & Selection, 9(7):617-621.

Riechmann et al., 1988, "Reshaping human antibodies for therapy," Nature, 332:323-327.

Sondermann et al., 2000, "The 3.2-Å crystal structure of the human IgG1 Fc fragment-FcγRIII complex," Nature, 406(6793):267-273.

Thommesen et al., 2000, "Lysine 322 in the human IgG3 CH2 domain is crucial for antibody dependent complement activation," Molecular Immunology, 37(16):995-1004.

Van Dijk and Van De Winkel, 2001, "Human antibodies as next generation therapeutics," Current Opinion in Chemical Biology, 5(4):368-374.

Woof and Burton, 2004, "Human antibody-Fc receptor interactions illuminated by crystal structures," Nature Reviews Immunology, 4(2):89-99.

Yang et al., 2011, "Therapeutic Potential and Challenges of Targeting Receptor Tyrosine Kinase ROR1 with Monoclonal Antibodies in B-Cell Malignancies," PLoS One, 6(6):e21018.

* cited by examiner

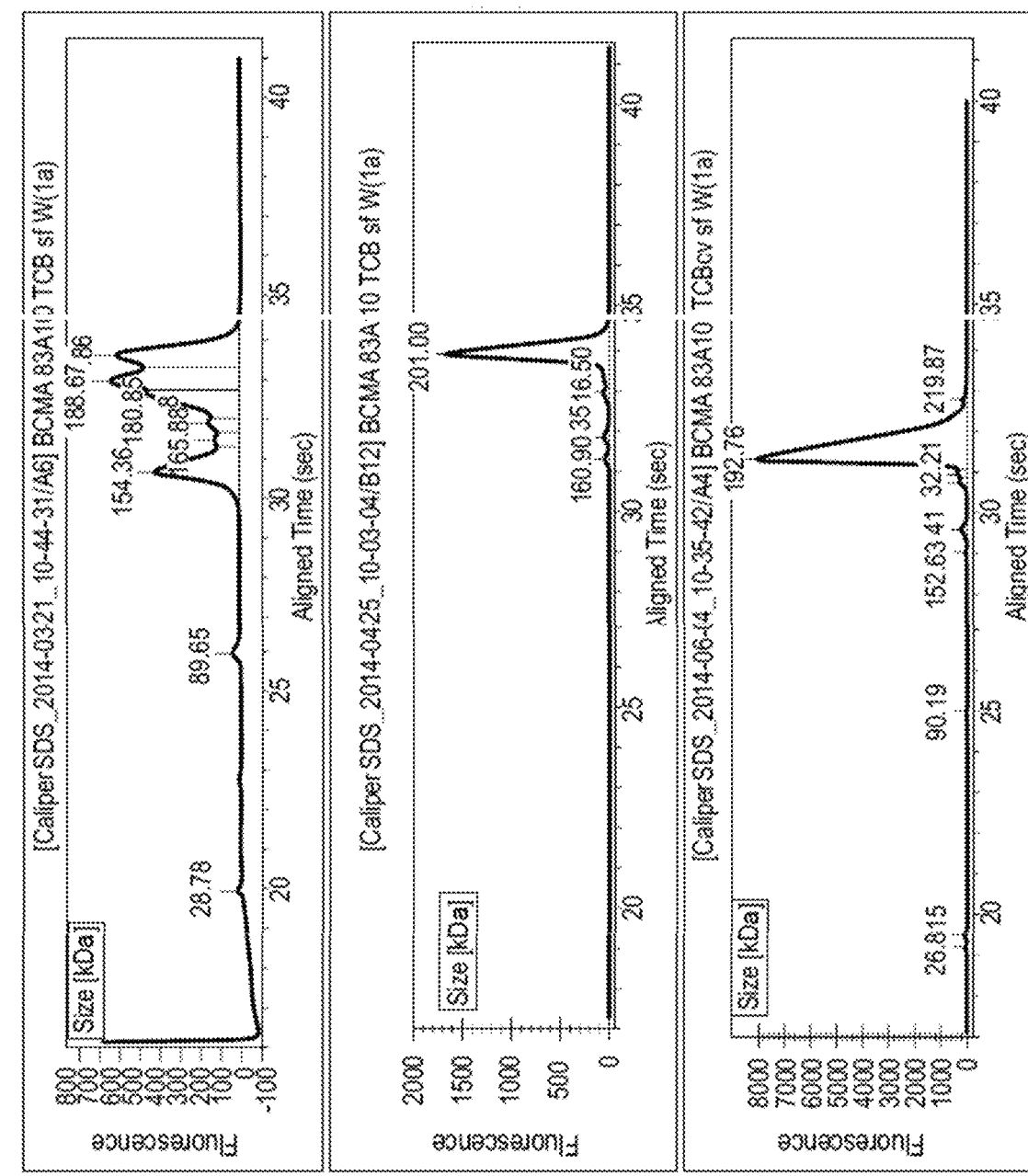

83A10-TCB
Pur. methods: PA
Purity: 61.3%
Yield: 26.2 mg/L
Amount: 24.3 mg
Monomer: 63.7%
LC-MS: n.d.

83A10-TCBcv
Pur. methods: PA
Purity: 81.0%
Yield: 51.5 mg/L
Amount: 50.2 mg
Monomer: 68.2%
LC-MS: n.d.

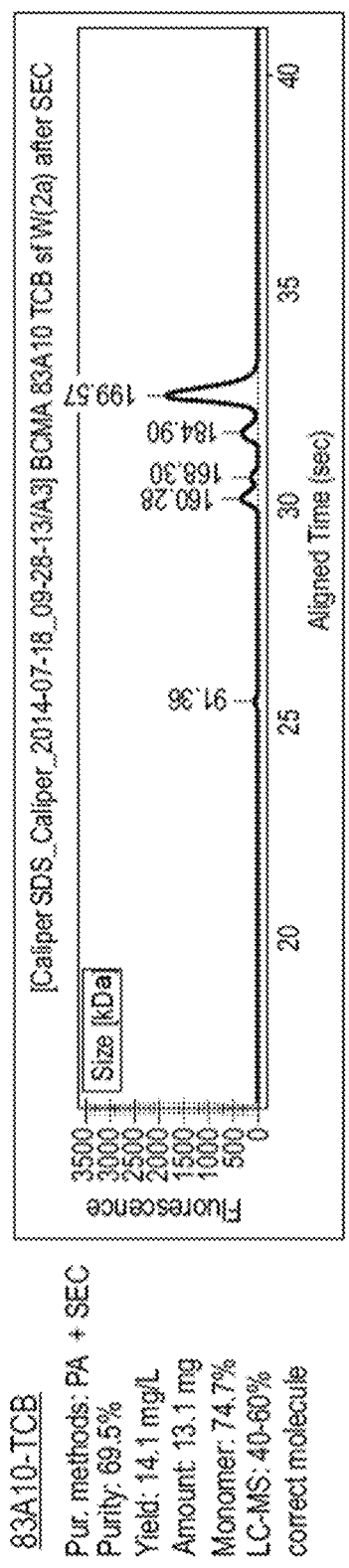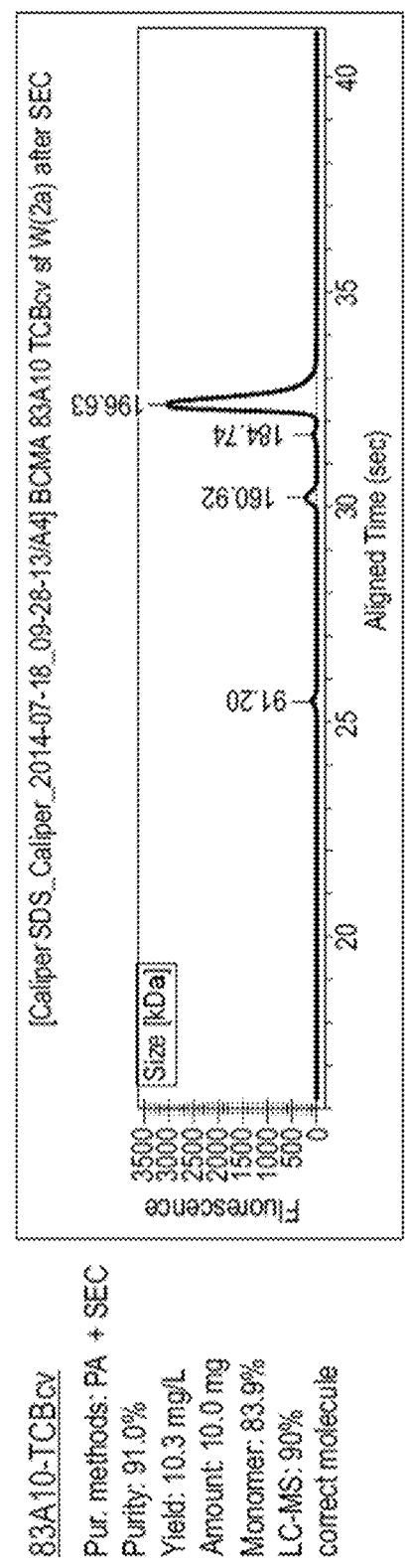
FIG. 3H
83A10-TCB
Pur. methods: PA + SEC
Purity: 69.5%
Yield: 14.1 mg/L
Amount: 13.1 mg
Monomer: 74.7%
LC-MS: 40-60% correct molecule
FIG. 3I
83A10-TCBcv
Pur. methods: PA + SEC
Purity: 91.0%
Yield: 10.3 mg/L
Amount: 10.0 mg
Monomer: 83.9%
LC-MS: 90% correct molecule

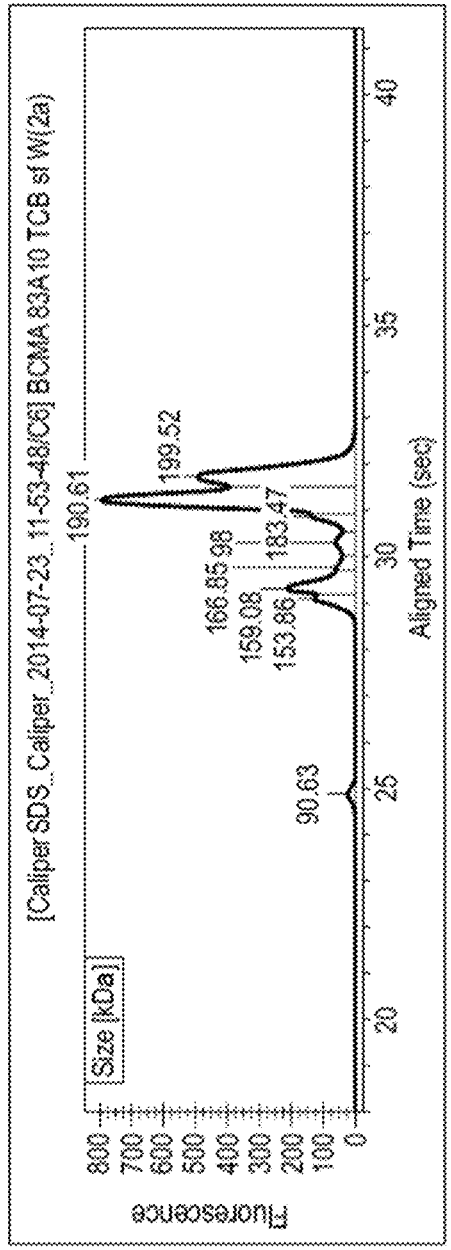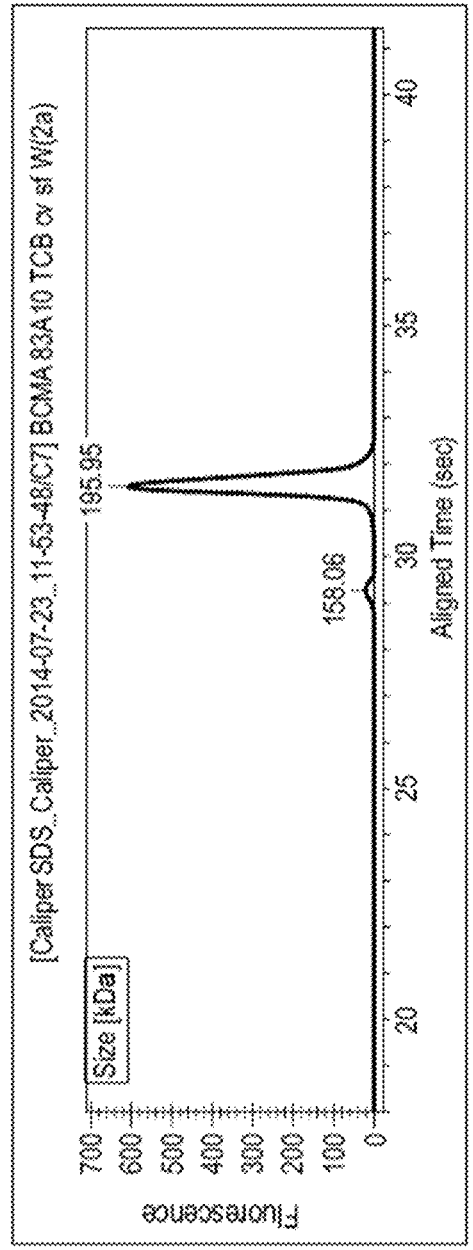

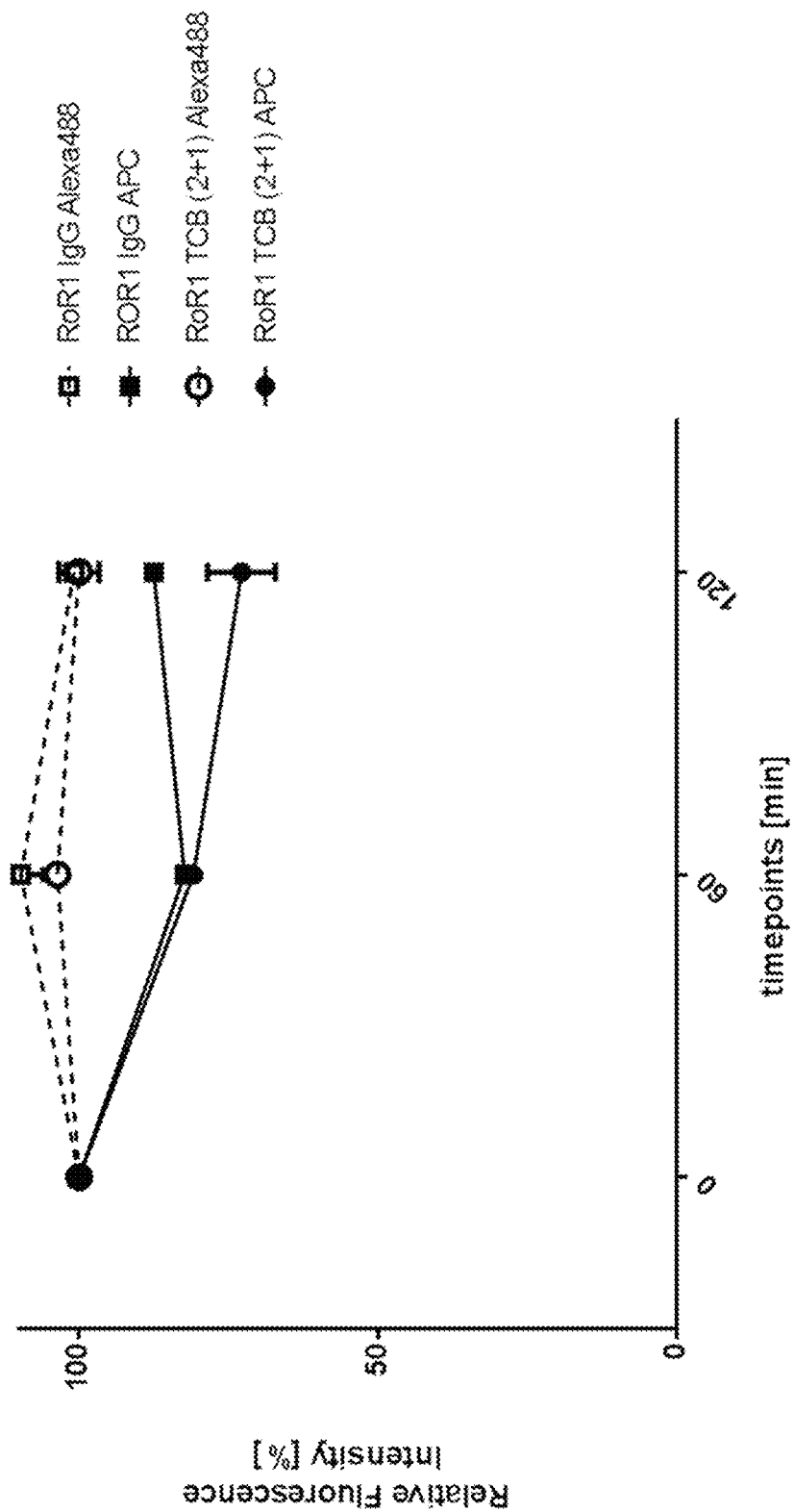

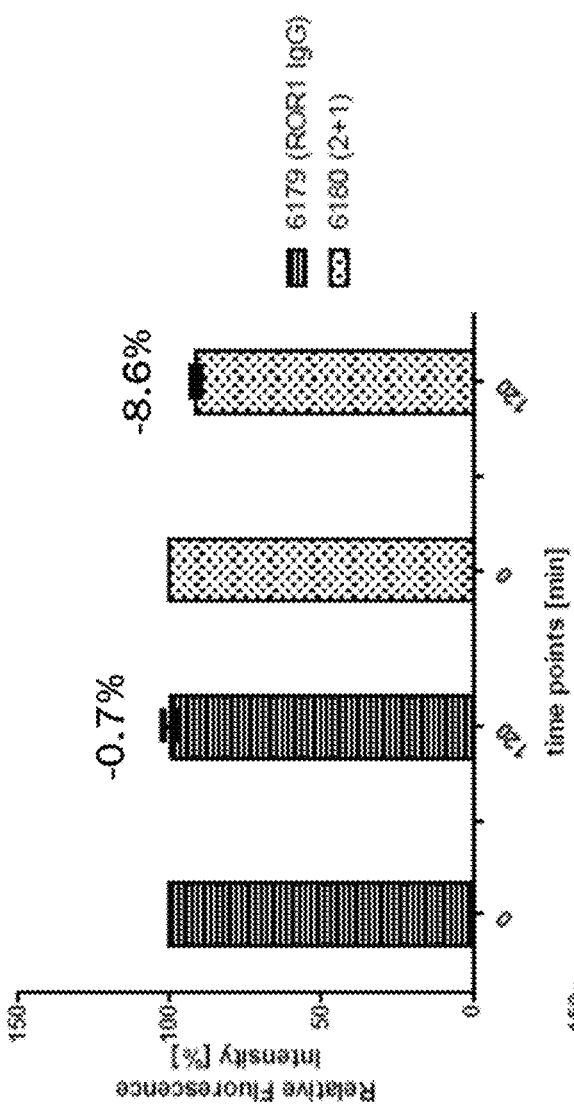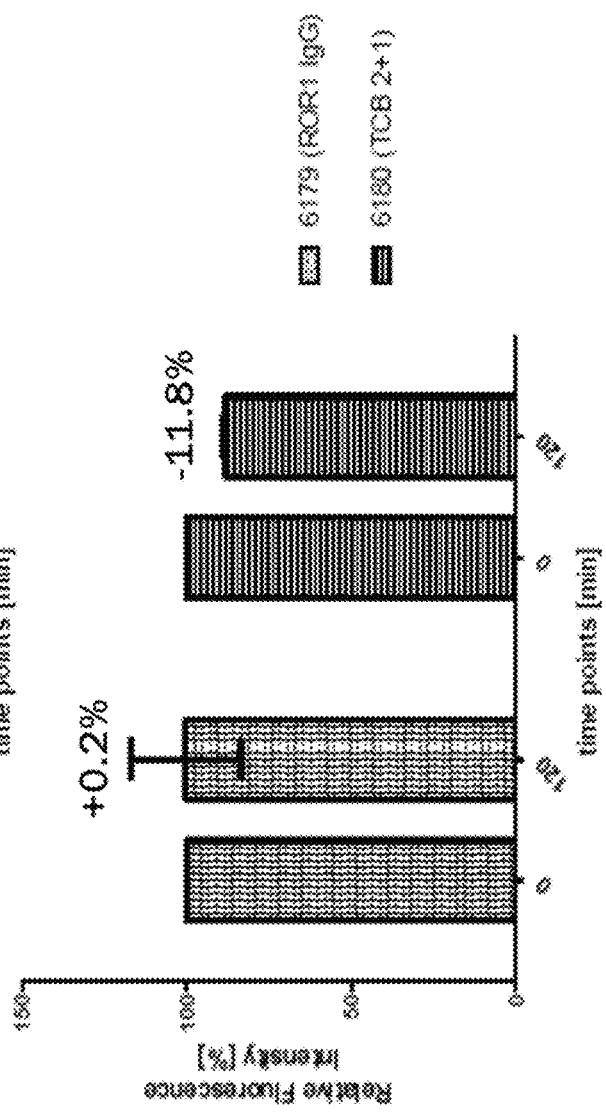

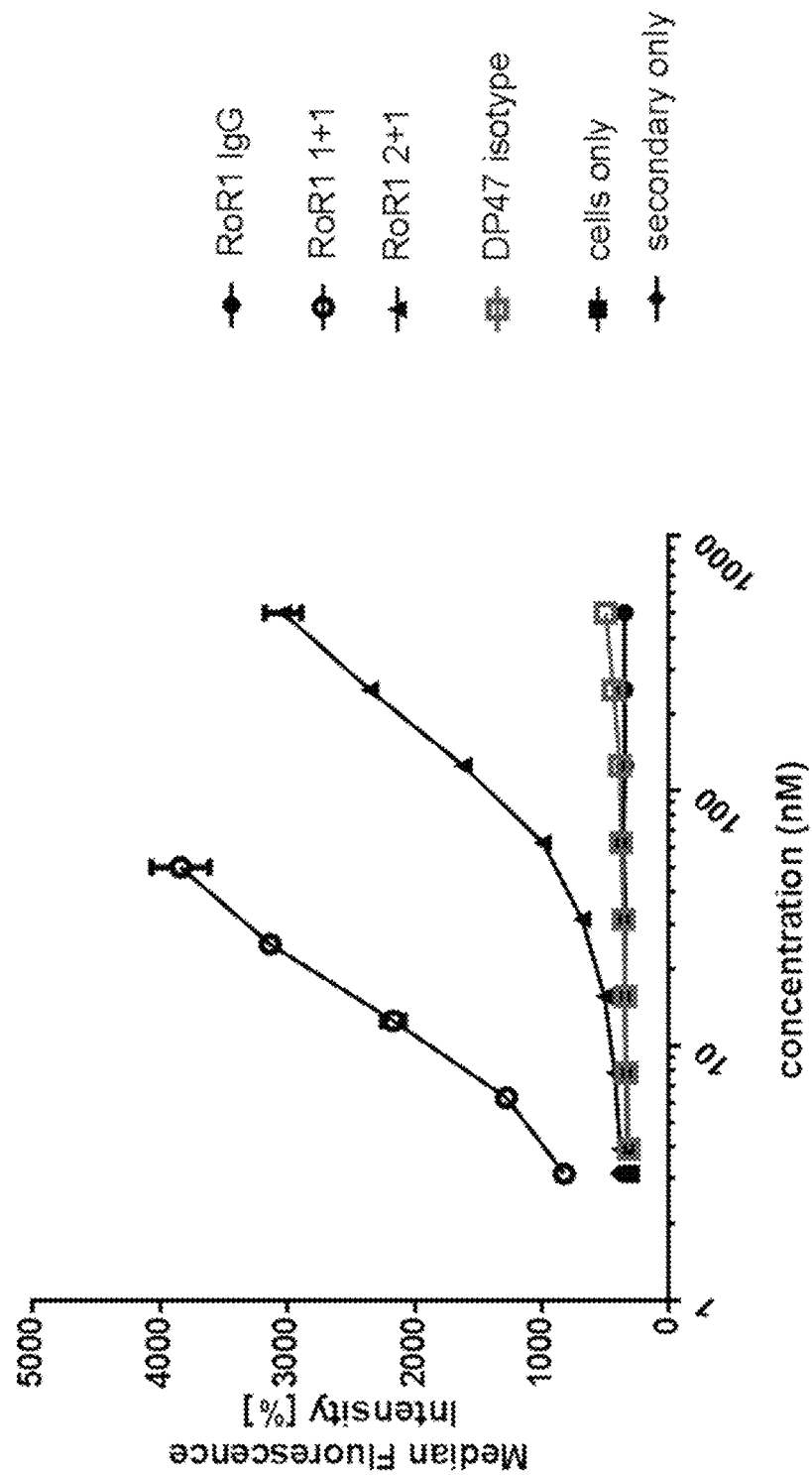

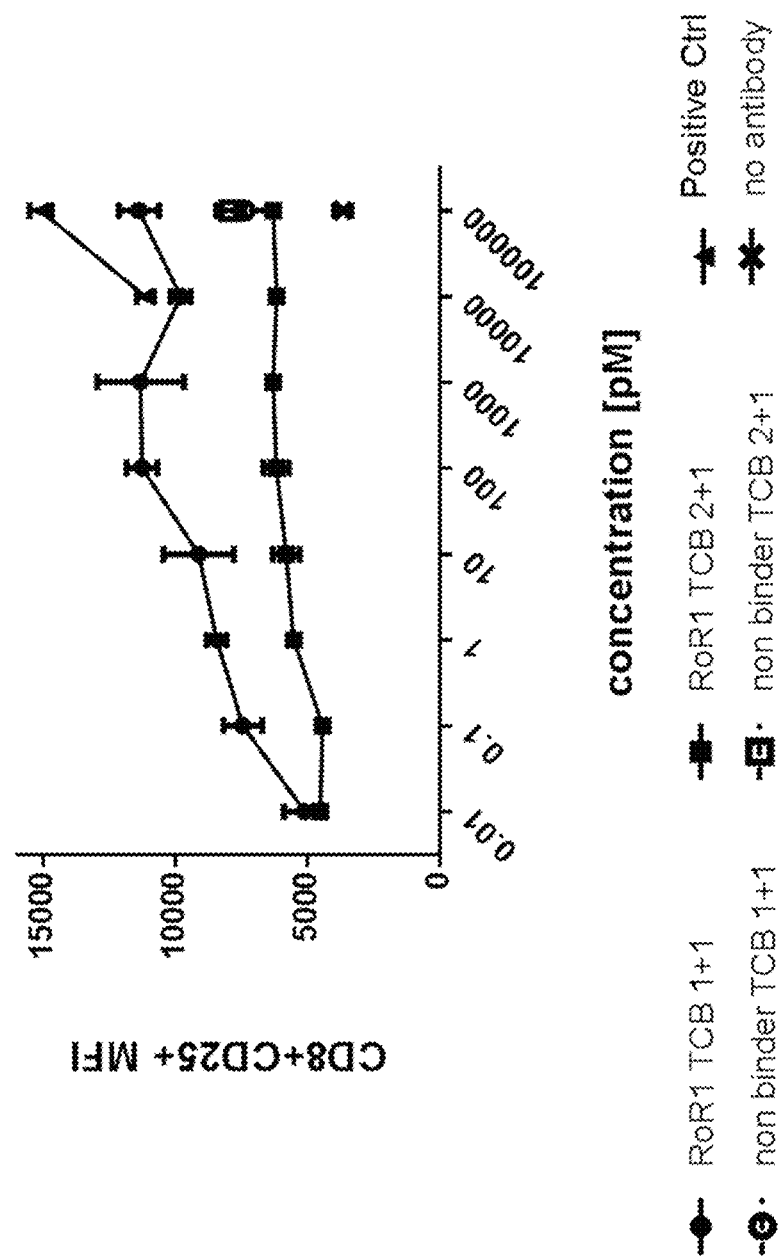

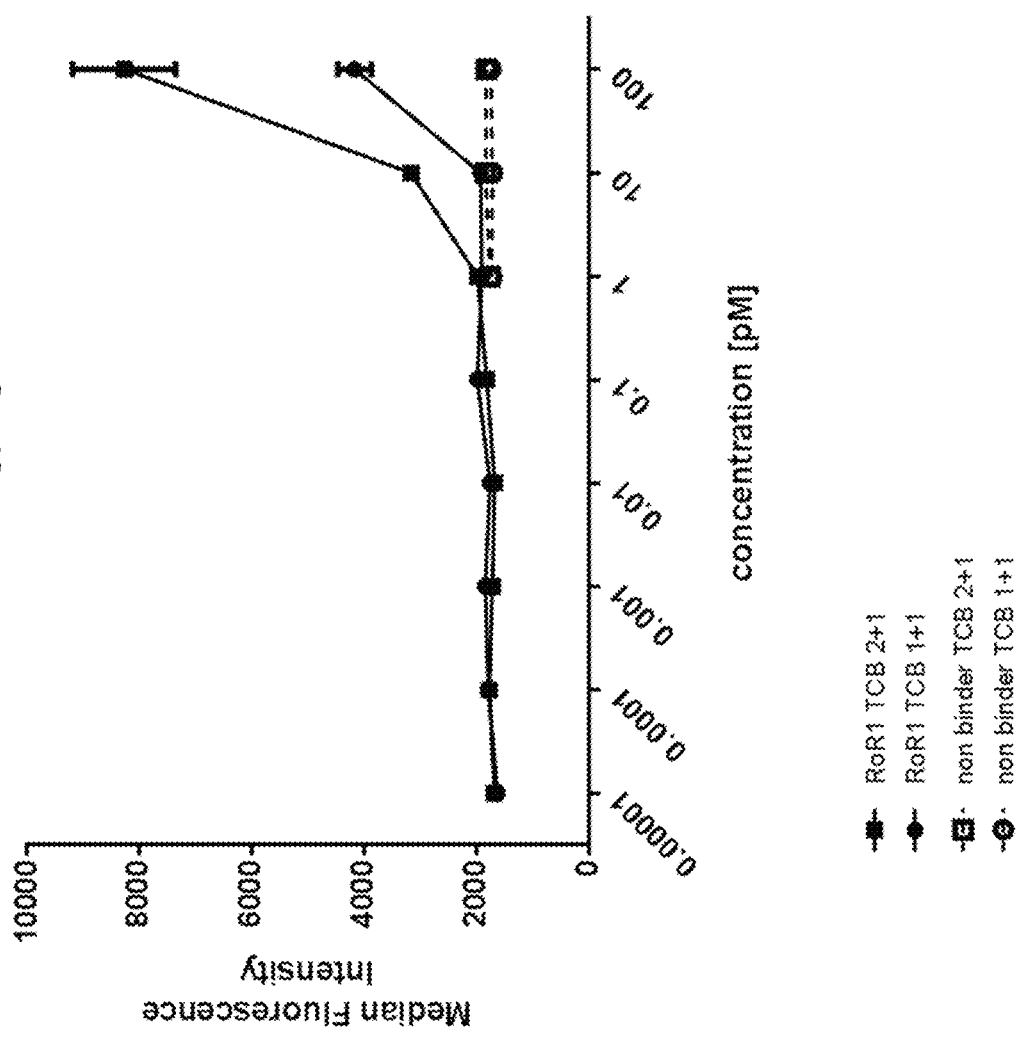

BISPECIFIC ANTIBODIES AGAINST CD3EPSILON AND ROR1

CROSS-REFERENCE TO RELATED APPLICATION

This present application claims benefit of priority from International Application No. PCT/EP2015/073308, filed Oct. 8, 2015, which claims priority from EP Application No. 14188378.5, filed Oct. 9, 2014 and EP Application No. 14188727.3, filed Oct. 14, 2014.

JOINT RESEARCH AGREEMENT

The instant application is directed to an invention(s) that was made as a result of activities undertaken within the scope of a Joint Research Agreement made between ENGMAB AG (now ENGMAB SÀRL) and F. HOFF-MANN-LA ROCHE LTD.

SEQUENCE LISTING

The instant application contains a Sequence Listing submitted via EFS-Web and hereby incorporated by reference in its entirety. Said ASCII copy, created on Oct. 18, 2019, is named 298068-00164.txt and is 113,816 bytes in size.

The present invention relates to novel bispecific antibodies against CD3ε and ROR1, their manufacture and use.

BACKGROUND OF THE INVENTION

ROR1 (synonyms: tyrosine-protein kinase transmembrane receptor ROR1, EC=2.7.10.1, neurotrophic tyrosine kinase, receptor-related 1, UniProtKB Q01973) is a tyrosine-protein kinase receptor. The receptor is described in Masiakowski P., Carroll R. D., J. Biol. Chem. 267:26181-26190(1992) "A novel family of cell surface receptors with tyrosine kinase-like domain." WO9218149 and WO9527060 mention ROR-1 as Rtk-2 and antibodies against ROR-1. WO2002087618 mentions a method of controlling the growth and differentiation of cancer by selectively inhibiting a growth factor receptor. Such a receptor would be Ror1 or Ror2. WO2005100605 mentions ROR1 as a therapeutic target for breast cancer and anti ROR1 antibodies which specifically bind to ROR1, to the extracellular region of ROR1 (M1-V406) and ROR1 fragments Q73-V139, E165-I299, K312-C391. WO2007051077 relates to an anti-ROR1 antibody and its use in lymphoma cell detection. WO2008103849 also mentions anti-ROR1 antibodies. Rabbani H. et al., Blood (ASH Annual Meeting Abstracts) 2010 116: Abstract 916) discloses the use of anti ROR1 antibodies for the treatment of chronic Lymphocytic leukemia (CLL). Rabbani used anti-ROR1 an antibody against the extracellular domain, an antibody against the CRD region (ligand binding site for Wnt proteins) and an antibody against the kringle domain. Daneshmanesh A H et al., Int. J. Cancer, 123 (2008) 1190-1195 relates to an anti ROR1 antibody that binds to the extracellular domain fragment WNISSELNKDSYLTL (SEQ ID NO:18) and an anti ROR1 antibody that binds to the intracellular domain fragment KSQKPYKIDSKQAS (SEQ ID NO:20). Also the use of such antibodies for the treatment of CLL is mentioned.

WO2011159847 relates to an anti-ROR1 antibody as a conjugate with a biologically active molecule for the treatment of ROR1 cancer like lymphoma or adenocarcinoma. WO2008076868, WO2008103849, WO201008069, WO2010124188, WO2011079902, WO2011054007, WO2011159847, WO2012076066, WO2012076727, WO2012045085, and WO2012097313 relate also to ROR1 binding molecules or anti ROR1 antibodies. WO2012075158 relates to an anti-ROR1 antibody comprising as light chain variable domain (VL) the sequence of SEQ ID NO:2 and as variable heavy chain domain (VH) the sequence of SEQ ID NO:6, and as respective CDRs the sequences of SEQ ID NO: 3, 4, 5, 7, 8, 9. This antibody is further named as MAB1. WO201209731 relates to an anti-ROR1 antibody comprising as light chain variable domain (VL) the sequence of SEQ ID NO:45 and as variable heavy chain domain (VH) the sequence of SEQ ID NO:42. This antibody is further named as MAB2. WO2012075158 relates to an anti-ROR1 antibody comprising as light chain variable domain (VL) the sequence of SEQ ID NO:46 and as variable heavy chain domain (VH) the sequence of SEQ ID NO:43. This antibody is further named as MAB3. WO2012075158 relates to an anti-ROR1 antibody comprising as light chain variable domain (VL) the sequence of SEQ ID NO:47 and as variable heavy chain domain (VH) the sequence of SEQ ID NO:44. This antibody is further named as MAB4.

WO2005040413 is directed to a screening method for the identification and/or validation of inhibitors of a receptor tyrosine kinase activity, including ROR1.

WO2008036449, WO2011014659 and WO2011050262 mention bispecific antibodies wherein one target can be ROR1. WO2007146968 mention multivalent single-chain binding proteins with effector function and ROR1 and CD3 are mentioned as possible targets. WO2011054007 is directed to a method of treatment of cancer administering an affinity reagent which binds to the extracellular domain of ROR1. Bispecific antibodies with CD3 are also mentioned. WO2014031174 mentions bispecific antibodies which are specific to two different epitopes of ROR1. The preferred antibody D10 strongly internalizes at 37° C. in MDA MB 231 epithelial breast adenocarcinoma. Yang and Baskar PLos ONE 6 (2011) e21018, like WO2012075158, mention also anti-ROR1 antibody R12. Rebagay R. et al., Frontiers in Oncology (2012) 7, Article 34, 1-8 mention that RORs are pharmaceutical targets and a means to deliver cytotoxic agents in the cells which express the target on the cell surface. Rebagay also mention bispecific antibodies such as BiTE. Strong internalization is favorable for armed antibodies i.e. antibody drug conjugates according to Rebagay. D. Mezzanzanica D et al., Int. Journal of Cancer, 41 (1988) 609-615 investigated a therapeutic approach by retargeting CTLs by a bispecific antibody consisting of MOv18 (a poorly internalizing folate receptor alpha antibody specific for human ovarian carcinoma cells) and an anti-CD3 antibody (OKT3 or TR66). Hudecek M et al., Blood, 116 (2010), 4532-4541, mention that ROR1 is expressed by B cell chronic lymphocytic leukemia (B-CLL) and mantle cell lymphoma (MCL). Such cells can be targeted by activated CD8$^+$ T cells transfected with, and expressing scFv from murine anti-ROR1 antibody 2A2. Such cells are useful for treatment of B cell malignancies. Baskar S. et al., mAbs 4:3 (2012) 349-361 relate to the targeting of malignant B cells with an immunotoxin BT-1 comprising scFv 2A2 anti-ROR1 conjugated to PE38 toxin. The immunotoxin is partially internalized and induces apoptosis.

The TCR/CD3 complex of T-lymphocytes consists of either a TCR alpha (α)/beta (β) or TCR gamma (γ)/delta (δ) heterodimer coexpressed at the cell surface with the invariant subunits of CD3 labeled gamma (γ), delta (δ), epsilon (ε), zeta (ζ), and eta (η). Human CD3ε is described under UniProt P07766 (CD3E_HUMAN). An anti CD3ε antibody described in the state of the art is SP34 (Yang S J, The Journal of Immunology (1986) 137; 1097-1100). SP34 reacts with both primate and human CD3. SP34 is available from PharMingen™ (BD Biosciences). A further anti CD3 antibody described in the state of the art is UCHT-1 (see WO2000041474). A further anti CD3 antibody described in the state of the art is BC-3 (Fred Hutchinson Cancer Research Institute; used in Phase I/II trials of GvHD, Anasetti C et al., Transplantation 54: 844 (1992)).

A wide variety of recombinant bispecific antibody formats have been developed in the recent past, e.g. by fusion of, e.g. an IgG antibody format and single chain domains (see Kontermann R E, mAbs 4:2, (2012) 1-16). Bispecific antibodies wherein the variable domains VL and VH or the constant domains CL and CH1 are replaced by each other are described in WO2009080251 and WO2009080252.

An approach to circumvent the problem of mispaired byproducts, which is known as 'knobs-into-holes', aims at forcing the pairing of two different antibody heavy chains by introducing mutations into the CH3 domains to modify the contact interface. On one chain bulky amino acids were replaced by amino acids with short side chains to create a 'hole'. Conversely, amino acids with large side chains were introduced into the other CH3 domain, to create a 'knob'. By coexpressing these two heavy chains (and two identical light chains, which have to be appropriate for both heavy chains), high yields of heterodimer formation ('knob-hole') versus homodimer formation ('hole-hole' or 'knob-knob') was observed (Ridgway J B, Presta L G, Carter P; and WO1996027011). The percentage of heterodimer could be further increased by remodeling the interaction surfaces of the two CH3 domains using a phage display approach and the introduction of a disulfide bridge to stabilize the heterodimers (Merchant A M, et al, Nature Biotech 16 (1998) 677-681; Atwell S, Ridgway J B, Wells J A, Carter P., J Mol Biol 270 (1997) 26-35). New approaches for the knobs-into-holes technology are described in e.g. in EP 1870459A1. Although this format appears very attractive, no data describing progression towards the clinic are currently available. One important constraint of this strategy is that the light chains of the two parent antibodies have to be identical to prevent mispairing and formation of inactive molecules. Thus this technique is not appropriate for easily developing recombinant, bispecific antibodies against two targets starting from two antibodies against the first and the second target, as either the heavy chains of these antibodies and/or the identical light chains have to be optimized. Xie, Z., et al, J Immunol Methods 286 (2005) 95-101 refers to a format of bispecific antibody using scFvs in combination with knobs-into-holes technology for the FC part. WO2012116927 and WO2010145792 mention exchanging the CH1 and CL domains. WO2009080254 mentions knob in hole constructs for producing bispecific antibodies. WO 2006093794 relates to heterodimeric protein binding compositions. WO199937791 describes multipurpose antibody derivatives. Morrison, S. L., et al., J. Immunol. 160 (1998) 2802-2808 refers to the influence of variable region domain exchange on the functional properties of IgG.

WO 201302362 relate to heterodimerized polypeptides. WO201312733 relates to polypeptides comprising heterodimeric Fc regions. WO2012131555 relates to engineered heterodimeric immunoglobulins. EP 2647707 relates to engineered hetero-dimeric immunoglobulins. WO2009080251, WO 2009080252, WO 2009080253, WO 2009080254 and Schaefer, W. et al, PNAS, 108 (2011) 11187-1191 relate to bivalent, bispecific IgG antibodies with a domain crossover. The multispecific antibodies with VH/VL replacement/exchange in one binding to prevent light chain mispairing (CrossMabVH-VL) which are described in WO2009080252, (see also Schaefer, W. et al, PNAS, 108 (2011) 11187-1191) clearly reduce the byproducts caused by the mismatch of a light chain against a first antigen with the wrong heavy chain against the second antigen (compared to approaches without such domain exchange). However their preparation is not completely free of side products. The main side product is based on a Bence-Jones-type interaction (Schaefer, W. et al, PNAS, 108 (2011) 11187-1191).

Accordingly there is a need for bispecific antibodies against CD3ε and ROR1 with VH/VL exchange which can be produced in high yield and easily purified.

Ovarian cancer is the leading cause of death from gynecologic cancer in the United States and the seventh most common cancer and the eighth most common cause of death from cancers in women. An estimated 21,980 new cases of ovarian cancer and 14,270 deaths related to ovarian cancers are expected in the United States in 2014. Worldwide, nearly 225,000 women will be diagnosed with ovarian cancer, and more than 140,000 will die of the disease (Cancer Facts & Figures 2014). The incidence of ovarian cancer increases with age and is most prevalent in the eighth decade of life. About half of the women diagnosed with ovarian cancer are 63 years or older. Ovarian cancer usually has a relatively poor prognosis. If diagnosed at the localized stage, the 5-year survival rate is 92%, however, only 15% of all cases are detected at this stage. The majority of cases (61%) are diagnosed after the disease has already metastasized. For women diagnosed with distant metastases, the 5-year survival rate is 27%. Despite advances in surgery and chemotherapy over the past two decades, only modest progress has been achieved in improving the overall survival in patients with ovarian cancer. Although the majority of women with advanced ovarian cancer respond to first-line chemotherapy, most responses are not durable. More than 80% of patients will have a recurrence of their disease after first-line treatment, and more than 50% will die of recurrent disease within 5 years of diagnosis. Targeted therapy is a newer type of cancer treatment that uses drugs or other substances to identify and attack cancer cells while doing little damage to normal cells. The targeted therapy drug that has been studied the most in ovarian cancer is bevacizumab (Avastin®). In studies, bevacizumab has been shown to shrink or slow the growth of advanced ovarian cancers. Trials to see if bevacizumab works even better when given along with chemotherapy have shown good results in terms of shrinking (or stopping the growth of) tumors, but it has not yet been shown to help women live longer. WO2007146957 relate to inhibiting tumor growth with ROR1-antagonizing agents. Such agents can be e.g. antibodies against ROR1 and identified by screening with tumor cell lines. As such screening tumor cell lines ovarian cancer cell lines are mentioned. U.S. Pat. No. 8,212,009 relates to a method for treating a ROR1 related cancer in a subject. The ROR1 related cancer are among others also ovarian cancer. WO2011054007 relates to a method for the treatment of ovarian cancer comprising administering an antibody against ROR1. Accordingly there is a need for a ROR1 based agent for the treatment of ovarian cancer.

SUMMARY OF THE INVENTION

The invention relates to a bispecific antibody specifically binding to the two targets human CD3ε (further named also as "CD3") and the extracellular domain of human ROR1 (further named also as "ROR1").

The invention relates to a bispecific bi- or trivalent antibody specifically binding to CD3 and ROR1, wherein the variable domains VL and VH in a light chain and the respective heavy chain are replaced by each other, characterized in comprising a constant domain CL wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat). Preferably the antibody is monovalent for CD3 binding. Preferably in addition to the amino acid replacement at position 124 in the constant domain CL the amino acid at position 123 is substituted independently by lysine (K), arginine (R) or histidine (H). Preferably the antibody is monovalent for CD3 binding and amino acid 124 is K, amino acid 147 is E, amino acid 213 is E, and amino acid 123 is R or K. Preferably amino acid 123 is R for a kappa light chain and K for a lambda light chain.

The invention relates to a bispecific antibody specifically binding to CD3 and ROR1, characterized in comprising
a) the first light chain and the first heavy chain of a first antibody which specifically binds to ROR1; and
b) the second light chain and the second heavy chain of a second antibody which specifically binds to CD3, and wherein the variable domains VL and VH in the second light chain and second heavy chain of the second antibody are replaced by each other; and
c) wherein in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to EU index of Kabat) (see e.g. FIGS. 1A, 1C, 1F, 1H, 1J).

Preferably said bispecific antibody described in the last preceding paragraph is further characterized in that said bispecific antibody comprises in addition a Fab fragment of said first antibody (further named also as "ROR1-Fab") and in the constant domain CL said ROR1-Fab the amino acid at position 124 is substituted independently by lysine (K), arginine (R) or histidine (H) (numbering according to Kabat), and wherein in the constant domain CH1 of said ROR1-Fab the amino acid at positions 147 and the amino acid at position 213 is substituted independently by glutamic acid (E), or aspartic acid (D) (numbering according to EU index of Kabat) (see e.g. FIGS. 1C, 1F).

The invention further relates to a bispecific antibody specifically binding to CD3 and ROR1, characterized in comprising
a) the first light chain and the first heavy chain of a first antibody which specifically binds to ROR1; and
b) the second light chain and the second heavy chain of a second antibody which specifically binds to CD3, and wherein the variable domains VL and VH in the second light chain and second heavy chain of the second antibody are replaced by each other; and wherein
c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to EU index of Kabat) (see e.g. FIGS. 1B, 1D, 1G, 1I, 1K).

Preferably said bispecific antibody described in the last preceding paragraph is further characterized in that said bispecific antibody comprises in addition a second Fab fragment of said first antibody ("ROR1-Fab") (see e.g. FIG. 1D, 1G).

Preferably in addition to the amino acid replacement at position 124 in the constant domain CL of the first or second light chain the amino acid at position 123 is substituted independently by lysine (K), arginine (R) or histidine (H).

Preferably in the constant domain CL the amino acid at position 124 is substituted by lysine (K), in the constant domain CH1 the amino acid at position 147 and the amino acid at position 213 are substituted by glutamic acid (E). Preferably in addition in the constant domain CL in the amino acid at position 123 is substituted by arginine (R).

Preferably in the constant domain CL the amino acid at position 124 is substituted by lysine (K), in the constant domain CH1 the amino acid at position 147 and the amino acid at position 213 are substituted by glutamic acid (E). Preferably in addition in the constant domain CL in the amino acid at position 123 is substituted by lysine (K).

In a preferred embodiment of the invention the antibody according to the invention consists of one Fab fragment of an antibody specifically binding to CD3 (further named also as "CD3-Fab"), and one Fab fragment of an antibody specifically binding to ROR1 (further named also as "ROR1-Fab(s)") and a Fc part, wherein the CD3-Fab and the ROR1-Fab are linked via their C-termini to the hinge region of said Fc part. Either the CD3-Fab or the ROR1-Fab comprises aa substitution and the CD3-Fab comprises crossover (FIGS. 1A and 1B).

In a preferred embodiment of the invention the antibody according to the invention consists of one CD3-Fab, and one ROR1-Fab and an Fc part, wherein the CD3-Fab and the ROR1-Fab are linked via their C-termini to the hinge region of said Fc part and a second ROR1-Fab, which is linked with its C-terminus to the N-terminus of the CD3-Fab. The CD3-Fab comprises crossover and either the CD3-Fab or both ROR1-Fabs comprise aa substitution (FIGS. 1C, 1D, 1F,1G). Especially preferred is a bispecific antibody comprising ROR1-Fab-Fc-CD3-Fab-ROR1-Fab, wherein both ROR1-Fabs comprise aa substitution and the CD3-Fab comprises VL/VH crossover (FIG. 1C). Especially preferred is a bispecific antibody consisting of ROR1-Fab-Fc-CD3-Fab-ROR1-Fab, wherein both ROR1-Fabs comprise aa substitution Q124K, E123R, K147E and K213E (kappa light chain) or E124K, E123K, K147E and K213E (lambda light chain) and the CD3-Fab comprises VL/VH crossover. Especially preferred is a bispecific antibody consisting of ROR1-Fab-Fc-CD3-Fab-ROR1-Fab, wherein both ROR1-Fabs comprise aa substitution Q124K, E123R, K147E and K213E (kappa light chain) or E124K, E123K, K147E and K213E (lambda light chain) and the CD3-Fab comprises VL/VH crossover. Especially preferred is that both ROR1-Fabs comprise as CDRs the CDRs of antibody MAB1, or as VH/VL the VH/VL of MAB1.

In a preferred embodiment of the invention the antibody according to the invention consists of two ROR1-Fabs and an Fc part, wherein the ROR1-Fabs are linked via their C-termini to the hinge region of said Fc part and a CD3-Fab, which is linked with its C-terminus to the N-terminus of one ROR1-Fab. The CD3-Fab comprises crossover and either the CD3-Fab or both ROR1-Fabs comprise aa substitution (FIGS. 1F and 1G).

In a preferred embodiment of the invention the antibody according to the invention consists of one CD3-Fab, which is linked via its C-terminus to the hinge region of said Fc part and a ROR1-Fab, which is linked with its C-terminus to the N-terminus of the CD3-Fab. The CD3-Fab comprises crossover and either the CD3-Fab or the ROR1-Fab comprise aa substitution (FIGS. 1H and 1I).

In a preferred embodiment of the invention the antibody according to the invention consists of one ROR1-Fab, which is linked via its C-terminus to the hinge region of said Fc part and a CD3-Fab, which is linked with its C-terminus to the N-terminus of the ROR1-Fab. The CD3-Fab comprises crossover and either the CD3-Fab or the ROR1-Fab comprise aa substitution (FIGS. 1J and 1K).

In a further embodiment of the invention the bispecific antibody according to the invention is
a) of construct ROR1 Fab-Fc-CD3 Fab-ROR1 Fab,
b) comprises VL/VH crossover within the Fab fragment of the anti-CD3 antibody,
c) comprises a human IgG1Fc part,
d) comprises within the Fc part substitution of Pro329 with glycine and substitutions of Leu234 by alanine and Leu235 by alanine, and
e) in the constant domain CL of both ROR1 Fabs the amino acid at position 124 is substituted by lysine (K) and at position 123 by arginine (R) for a kappa light and lysine (K) for a lambda light chain, in the constant domain CH1 the amino acid at position 147 and the amino acid at position 213 are substituted by glutamic acid (E).

The Fab fragments are chemically linked together by the use of an appropriate linker according to the state of the art. Appropriate linkers are described e.g. in US 20140242079. Preferably a (Gly4-Ser1)2 linker (SEQ ID NO:19) is used (Desplancq D K et al., Protein Eng. 1994 August; 7(8):1027-33 and Mack M. et al., PNAS Jul. 18, 1995 vol. 92 no. 15 7021-7025). Linkage between two Fab fragments is performed between the heavy chains. Therefore the C-terminus of CH1 of a first Fab fragment is linked to the N-terminus of VH of the second Fab fragment (no crossover) or to VL (crossover). Linkage between a Fab fragment and the Fc part is performed according to the invention as linkage between CH1 and CH2.

The first and a second Fab fragment of an antibody specifically binding to ROR1 are preferably derived from the same antibody and preferably identical in the CDR sequences, variable domain sequences VH and VL and/or the constant domain sequences CH1 and CL. Preferably the amino acid sequences of the first and a second Fab fragment of an antibody specifically binding to ROR1 are identical. Preferably the ROR1 antibody is an antibody comprising the CDR sequences of antibody MAB1, an antibody comprising the VH and VL sequences of antibody MAB1, or an antibody comprising the VH, VL, CH1, and CL sequences of antibody MAB1.

Preferably the bispecific antibody comprises as Fab fragments and Fc part, not more than one Fab fragment of an anti-CD3 antibody, not more than two Fab fragments of an anti-ROR1 antibody and not more than one Fc part, preferably a human Fc part. Preferably the second Fab fragment of an anti-ROR1 antibody is linked via its C-terminus either to the N-terminus of the Fab fragment of an anti-CD3 antibody or to the hinge region of the Fc part. Preferably linkage is performed between CH1 of ROR1-Fab and VL of CD3-Fab (VL/VH crossover).

Preferably the antibody portion specifically binding to human CD3, preferably the Fab fragment, is characterized in comprising a variable domain VH comprising the heavy chain CDRs of SEQ ID NO: 12, 13 and 14 as respectively heavy chain CDR1, CDR2 and CDR3 and a variable domain VL comprising the light chain CDRs of SEQ ID NO: 15, 16 and 17 as respectively light chain CDR1, CDR2 and CDR3 of the anti-CD3ε antibody (CDR MAB CD3 H2C). Preferably the antibody portion specifically binding to human CD3 is characterized in that the variable domains are of SEQ ID NO:10 and 11 (VHVL MAB CD3 H2C).

Preferably the antibody portion specifically binding to human CD3, preferably the Fab fragment, is characterized in comprising a variable domain VH comprising the heavy chain CDRs of SEQ ID NO: 23, 24 and 25 as respectively heavy chain CDR1, CDR2 and CDR3 and a variable domain VL comprising the light chain CDRs of SEQ ID NO: 26, 27 and 28 as respectively light chain CDR1, CDR2 and CDR3 of the anti-CD3ε antibody (CDR MAB CD3 CH2527). Preferably the antibody portion specifically binding to human CD3 is characterized in that the variable domains are of SEQ ID NO:21 and 22 (VHVL MAB CD3).

Preferably the antibody portion, preferably the Fab fragment, specifically binding to human ROR1 is characterized in comprising a variable domain VH comprising the heavy chain CDRs CDR1H of SEQ ID NO:7, a CDR2H of SEQ ID NO:8, a CDR3H of SEQ ID NO: 9 and comprising a variable domain VL comprising the light chain CDRs CDR1L of SEQ ID NO:3, a CDR2L of SEQ ID NO:4, a CDR3L of SEQ ID NO: 5 (CDR MAB1).

Preferably the antibody portion, preferably the Fab fragment, specifically binding to human ROR1 is characterized in comprising a VH of SEQ ID NO: 6 and a VL of SEQ ID NO: 2 (VHVL MAB1).

The invention relates to a bispecific antibody specifically binding to the extracellular domain of human ROR1 and to human CD3ε, characterized in comprising a heavy and light chain set of polypeptides SEQ ID NO:37, SEQ ID NO:38, SEQ ID NO:39, and SEQ ID NO:40.

The invention relates to a bispecific antibody specifically binding to the extracellular domain of human ROR1 and to human CD3ε, characterized in comprising a heavy and light chain set of polypeptides SEQ ID NO:37, SEQ ID NO:38, SEQ ID NO:39, and SEQ ID NO:41.

The invention further relates to a nucleic acid set encoding a respective heavy and light chain set.

Preferably the bispecific antibody according to the invention comprising constant heavy regions CH2/CH3 of IgG1 subclass is characterized in comprising the mutations L234A, L235A and P329G (numbering according to EU index of Kabat) to avoid FcR and C1q binding and minimizing ADCC/CDC. The advantage is that such an antibody of the invention mediates its tumor cell killing efficacy purely by the powerful mechanism of T-cell redirection/activation. Additional mechanisms of action like effects on complement system and on effector cells expressing FcR are avoided and the risk of side-effects is decreased.

The invention comprises preferably a heavy chain of an antibody according to the invention consisting of (from N-to-C-terminus) VH(ROR1)-CH1(ROR1)-VL(CD3)-CH1(CD3)-CH2-CH3, preferably of SEQ ID NO: 37, as well as the respective encoding nucleic acids. These polypeptides and respective nucleic acids are useful for the production of a bispecific antibody according to the invention.

The amino acid (aa) exchanges (further mentioned as "charge variants") outside of the CDRs of the bispecific antibodies according to the invention provide considerably improved production/purification without changing biological properties like binding to ROR1. By introduction of the aa exchanges (charge variants) according to the invention light chain LC mispairing and the formation of side products in production is significantly reduced and therefore purification is facilitated.

The invention relates to a bispecific antibody specifically binding to the two targets human CD3ε and the extracellular domain of human ROR1 which does not internalize. The bispecific antibody according to the invention is preferably characterized in not internalizing in a concentration of 1 nM in primary B-CLL cells at 37° C. during two hours. The bispecific antibody according to the invention is preferably characterized in that the bispecific antibody does not internalize in a cell based assay at 37° C. during 2 hrs, using ROR1-positive primary B-CLL cells and used at an antibody concentration of 1 nM, whereby not internalize means, that the mean fluorescence intensity (MFI), as detected by flow cytometry, of a bispecific antibody upon binding to ROR1-positive primary B-CLL cells measured at time 0 is not reduced more than 50%, preferably not more than 30% when re-measured after a 2 hr-incubation at 37° C.

Preferably the bispecific antibody according to the invention is a bivalent antibody and characterized in comprising a monovalent anti-ROR1 antibody specifically binding to ROR1, and a monovalent antibody specifically binding to CD3. A bivalent antibody is preferred if its said mean fluorescence intensity (MFI), as detected by flow cytometry, upon binding to ROR1-positive cells measured at time 0 is not reduced more than 50%, preferably not more than 30% by internalization when re-measured after a 2 hr-incubation at 37° C. Preferably the bispecific antibody according to the invention is a bivalent antibody and characterized in comprising a monovalent anti-ROR1 antibody specifically binding to ROR1, and a monovalent antibody specifically binding to CD3. Preferably the monovalent antibody specifically binding to CD3 is a Fab fragment, preferably a CD3 crossFab. Such a bivalent antibody is preferred if its said mean fluorescence intensity (MFI), as detected by flow cytometry, upon binding to ROR1-positive cells measured at time 0 is not reduced more than 50%, preferably not more than 30% by internalization when re-measured after a 2 hr-incubation at 37° C. Preferably the bispecific antibody according to the invention is a trivalent antibody and characterized in comprising a bivalent anti-ROR1 antibody specifically binding to ROR1, and a monovalent antibody specifically binding to CD3. Preferably the monovalent antibody specifically binding to CD3 is a Fab fragment or preferably a CD3 crossFab. A trivalent antibody is preferred if its said mean fluorescence intensity (MFI), as detected by flow cytometry, upon binding to ROR1-positive cells measured at time 0 is not reduced more than 50%, preferably not more than 30% by internalization when re-measured after a 2 hr-incubation at 37° C.

Preferably the bispecific antibody according to the invention does not internalize in said cell based assay at 37° C. during 24 hrs.

Preferably the bispecific antibody according the invention does not internalize in said cell based assay if used in a concentration between 0.1 pM and 200 nM.

A further embodiment of the invention is an antibody according to this invention with an affinity ratio of ROR1 to CD3 of 5000:1 to 5:1, as determined by Kd values using surface plasmon resonance. Such an antibody is favorable because of its stronger binding to malignant cells over T cells. Preferably the Kd values are about 100 nM for the CD3 antibody and about 50 pM to 50 nM for the ROR1 antibody.

Preferably the B-CLL cells are used according to the invention in a cell concentration of $1\times10^6$ cells/mL (primary PBMC from CLL patients) or $1\times10^6$ cells/mL (ATCC CCL-155) or $1\times10^6$ cells/mL (ATCC CRL-3004).

Preferably the antibody portion specifically binding to CD3 is characterized in being humanized. Preferably the CD3 Mab according to the invention binds to the same epitope of CD3ε as antibody H2C (described in WO2008119567) and/or antibody CH2527 (described in WO2013026839) or is preferably antibody H2C or CH2527.

Preferably the antibody portion specifically binding to ROR1 is characterized in comprising a light chain variable domain (VL) comprising as respective variable light chain CDRs the CDRs of SEQ ID NO: 3, 4, 5 and a heavy chain variable domain (VH) comprising as respective variable heavy chain CDRs the CDRs of SEQ ID NO:7, 8, 9. Preferably the antibody portion specifically binding to ROR1 is characterized in comprising as light chain variable domain (VL) a sequence being at least 90% identical to the sequence of SEQ ID NO:2 and as variable heavy chain domain (VH) a sequence being at least 90% identical to the sequence of SEQ ID NO:6, Preferably the antibody portion specifically binding to ROR1 is characterized in comprising as light chain variable domain (VL) the sequence of SEQ ID NO:2 and as variable heavy chain domain (VH) the sequence of SEQ ID NO:6. Preferably the antibody portion specifically binding to ROR1 is characterized in being humanized. Preferably the ROR1 Mab according to the invention binds to the same epitope of ROR1 as the Mab mentioned above.

A further embodiment of the invention is a method for the preparation of a bispecific antibody according to the invention comprising the steps of transforming a host cell with one or more vectors comprising nucleic acid molecules encoding the respective antibodies or fragments, culturing the host cell under conditions that allow synthesis of said antibody molecule; and recovering said antibody molecule from said culture.

Preferably the method for the preparation of a bispecific antibody according to the invention comprising the steps of
a) transforming a host cell with one or more vectors comprising nucleic acid molecules encoding the heavy and light chain set of polypeptides SEQ ID NO:37, 38, 39, and 40, or the set of SEQ ID NO:37, 38, 39, and 41
b) culturing the host cell under conditions that allow synthesis of said antibody molecule; and
c) recovering said antibody molecule from said culture.

A further embodiment of the invention is a host cell comprising vectors comprising nucleic acid molecules encoding an antibody according to the invention.

A further embodiment of the invention is a host cell comprising vectors comprising nucleic acid molecules encoding the light chain and heavy chain of an antibody specifically binding to the first target and vectors comprising nucleic acid molecules encoding the light chain and heavy chain of an antibody specifically binding to the second target, wherein the variable domains VL and VH are replaced by each other.

A further preferred embodiment of the invention is a pharmaceutical composition comprising an antibody according to the invention and a pharmaceutically acceptable excipient.

A further preferred embodiment of the invention is a pharmaceutical composition comprising an antibody according to the invention for use as a medicament. A further preferred embodiment of the invention is an antibody according to the invention or a pharmaceutical composition comprising an antibody according to the invention for use as a medicament in the treatment of ROR1-positive hematological malignancies comprising chronic lymphocytic leukemia (CLL), hairy cell leukemia (HCL), acute lymphoblastic leukemia (ALL), acute myeloid leukemia (AML), chronic myeloid leukemia (CML), mantle cell lymphoma (MCL), marginal zone lymphoma (MZL), diffuse large B cell lymphoma (DLBCL), multiple myeloma (MM) and follicular lymphoma (FL). ROR1 is significantly and uniformly expressed on the cell surface of these various blood cancers. A further embodiment of the invention is an antibody according to the invention or a pharmaceutical composition comprising an antibody according to the invention for use as a medicament in the treatment of leukemias and non-Hodgkin lymphomas expressing ROR1. A preferred embodiment of the invention is an antibody according to the invention or a pharmaceutical composition comprising an antibody according to the invention for use as a medicament in the treatment of chronic lymphocytic leukemia (CLL) of B-cell lineage (B-CLL). B-CLL results from an acquired mutation to the DNA of a single marrow cell that develops into a B lymphocyte. Once the marrow cell undergoes the leukemic change, it multiplies into many cells and overtime crowd out normal cells since CLL cells grow and survive better than normal cells. The result is the uncontrolled growth of CLL cells in the bone marrow, leading to an increase in the number CLL cells in the blood. CLL symptoms usually develop over time with some patients being asymptomatic with only abnormal blood test results (e.g. increase in white blood cells). CLL patients with symptoms experience fatigue, short of breath, anemia, weight loss, decrease in appetite, lymph nodes and spleen enlargement and recurrent infections due to low immunoglobulin levels and decreased neutrophil counts (Leukemia & Lymphoma Society, 2009). A further preferred embodiment of the invention is an antibody according to the invention or a pharmaceutical composition comprising an antibody according to the invention for use as a medicament in the treatment of Multiple Myeloma. A further embodiment of the invention is an antibody according to the invention or a pharmaceutical composition comprising an antibody according to the invention for use as a medicament the treatment of plasma cell disorders like Multiple Myeloma MM or other B-cell disorders expressing ROR1. MM is a B-cell malignancy characterized by a monoclonal expansion and accumulation of abnormal plasma cells in the bone marrow compartment. MM also involves circulating clonal B cells with same IgG gene rearrangement and somatic hypermutation. MM arises from an asymptomatic, premalignant condition called monoclonal gammopathy of unknown significance (MGUS), characterized by low levels of bone marrow plasma cells and a monoclonal protein. MM cells proliferate at low rate. MM results from a progressive occurrence of multiple structural chromosomal changes (e.g. unbalanced translocations). MM involves the mutual interaction of malignant plasma cells and bone marrow microenvironment (e.g. normal bone marrow stromal cells). Clinical signs of active MM include monoclonal antibody spike, plasma cells overcrowding the bone marrow, lytic bone lesions and bone destruction resulting from overstimulation of osteoclasts (Dimopulos & Terpos, Ann Oncol 2010; 21 suppl 7: vii143-150). A further embodiment of the invention is an antibody according to the invention or a pharmaceutical composition comprising an antibody according to the invention for use as a medicament in the treatment of ROR1-positive solid tumors such as human breast cancers (Zhang S, PLoS One 2012; 7(3): e31127) and lung cancers (Yamaguchi T, Cancer Cell 2012; 21(3):348).

A further embodiment of the invention is the use of an antibody according to the invention or the pharmaceutical composition according to the invention for such treatments.

A further embodiment of the invention is the use of an antibody according to the invention or the pharmaceutical composition according to the invention for the treatment of a disease selected from the group consisting of ovarian cancer, lung cancer, breast cancer, gastric cancer, and/or pancreatic cancer. A further embodiment of the invention is an antibody according to the invention or the pharmaceutical composition according to the invention for use in the treatment of ovarian cancer, lung cancer, breast cancer, gastric cancer, and/or pancreatic cancer.

A further embodiment of the invention is the use of an antibody according to the invention or the pharmaceutical composition according to the invention for the treatment of ovarian cancer. A further embodiment of the invention is an antibody according to the invention or the pharmaceutical composition according to the invention for use in the treatment of ovarian cancer. A further embodiment of the invention is a method of treatment comprising administering to a cancer patient a therapeutically effect dose of the antibody according to the invention. A further embodiment of the invention is such method wherein the cancer is a selected from the group consisting of ovarian cancer, lung cancer, breast cancer, gastric cancer, and/or pancreatic cancer and hematologic malignancy. A further embodiment of the invention is such a method wherein chemotherapy or radiation is administered before, after, or concurrently with the antibody. A further embodiment of the invention is a method of treatment comprising administering to a patient having such disease an antibody according to the invention. A further embodiment of the invention is a method of treatment comprising administering to a patient having ovarian cancer an antibody according to the invention. A further embodiment of the invention is the use of an antibody according to the invention as a medicament for treating a cancer, preferably ovarian cancer. A further embodiment of the invention is the use of an antibody according to the invention in the manufacture of a medicament for treating a cancer, preferably ovarian cancer.

Preferably the antibody according to the invention or the pharmaceutical composition is administered once or twice a week preferably via subcutaneous administration (e.g. preferably in the dose range of 0.1 to 10 mg/m$^2$ once or twice a week). Due to superior cytotoxicity activities of the antibody according to the invention, it can be administered at a lower magnitude of clinical dose range as compared to conventional monospecific antibodies or conventional bispecific antibodies that are not T cell bispecifics (i.e. do not bind to CD3 on one arm). It is envisaged that for an antibody according to the invention subcutaneous administration is preferred in the clinical settings (e.g. in the dose range of 0.1-10 mg/m$^2$ once or twice a week). An antibody according to the invention is eliminated with a half-life of about several days which allows at least once or twice/week administration. Another advantage of the antibody according to the invention is a molecular weight (i.e. approximately 150-200 kDa) higher than the kidney filtration size limit (50-70 kDa).

This molecular weight allows long elimination half-life and makes subcutaneous administrations once or twice a week possible.

Preferably an antibody according to the invention is characterized by showing tumor growth inhibition of more than 70%, preferably of more than 85%, preferably of close to 100% in a xenograft model with a ROR1 expressing tumor cell line (for example CLL, MM, MCL cell lines) at a dose of 1 mg/kg body weight (BW) administered intravenously (i.v.) or subcutaneously (s.c.) or intraperitoneal (i.p.) twice a week or once a week, preferably 0.5 mg/kg BW administered i.v. or i.p. or s.c. twice a week or once a week, preferably at 0.1 mg/kg BW administered i.v. or i.p. or s.c. twice a week or once a week, preferably at 0.05 mg/kg BW administered i.v. or i.p. or s.c. twice a week or once a week, preferably at 0.01 mg/kg BW administered i.v. or i.p. or s.c twice a week or once a week, preferably at 5 µg/kg BW administered i.v. or i.p. or s.c. twice a week or once a week.

Preferably an antibody according to the invention is characterized by an elimination half-life in mice, preferably cynomolgus monkeys of longer than 12 hours, preferably 3 days or longer.

Bispecific antibodies binding to a target on tumor cells and to CD3 and having the molecular format (scFv)$_2$ have very short elimination half-life of 1 to 4 hours. In the clinical trials with the (scFv)$_2$ bispecific CD19×CD3 antibody blinatumomab, this compound had to be administered via a pump carried by the patients over weeks and months (Topp et al. J Clin Oncol 2011; 29(18): 2493-8). Compared to a twice a week or once a week iv or sc administration, treatment administered via a pump is much less convenient for the patients and also much more risky (e.g. failure of pump, issues with the catheter).

Preferably an antibody according to the invention is characterized in showing an EC50 value for binding to ROR1-positive cell lines (e.g. RPMI8226 cells, Rec-1 cells, Jeko cells) of 30 nM or lower, preferably an EC50 value of 15 nM and lower.

Preferably an antibody according to the invention is characterized by its capability to induce redirected killing of ROR1 expressing tumor cells (e.g. RPMI8226 cells, Rec-1 cells, Jeko cells) in the presence of human T cells with an EC50 lower than 10 nM, preferably 1 nM, preferably 0.05 nM, preferably 0.02 nM, preferably 0.002 nM and lower.

Stability of bispecific antibodies can be affected in practical conditions and clinical applications. Despite recent antibody engineering improvements, some recombinant proteins and molecular formats (e.g. scFVs fragments) tend to denature and form aggregates more easily than other under stress conditions (Worn and Pluckthun. J Mol Biol 2001; 305, 989-1010). Preferably an antibody according to this invention is characterized in that said antibody stored in standard formulation buffer at 37° C. preferably at 40° C., for 10 days, preferably up to 2 weeks, preferably up to 4 weeks, does not result in more than 10% changes (Δ), preferably not more than 5% changes (Δ), in high molecular weight (HMW) species and/or low molecular weight (LMW) species and/or monomer content as compared to the said antibody stored in the same formulation buffer at −80° C. for the same period of storage.

DESCRIPTION OF THE FIGURES

Remark: If not mentioned that Mab2 was used as anti-ROR1 antibody and/or as anti-ROR1 Fab in an anti-ROR1/anti-CD3 TCB antibody in the following descriptions of the figures, then Mab1 was used as anti-ROR1 antibody and/or as anti-ROR1 Fab in an anti-ROR1/anti-CD3 TCB antibody.

FIG. 1A-K. Preferred bispecific antibodies comprising the Fab fragments (specific to CD3 and ROR1) as specified: (1A, 1B) Fab ROR1-Fc-Fab CD3; (1C, 1D) Fab ROR1-Fc-Fab CD3-Fab ROR1; (1F, 1G) Fab ROR1-Fc-Fab ROR1-Fab CD3; (1H, 1I) Fc-Fab CD3-Fab ROR1; (1J, 1K) Fc-Fab ROR1-Fab CD3. Preferably, the Fabs CD3 include a VH-VL crossover to reduce LC mispairing and side-products. Fab CD3 and Fab ROR1 are linked to each other with flexible linkers.

FIGS. 3C-3E. Production and purification of 83A10-TCB without charge variant vs. 83A10-TCBcv with charge variant. CE-SDS (non-reduced) graphs of the final protein preparations after different methods of purification for 83A10-TCB and 83A10-TCBcv antibodies. Protein A (PA) affinity chromatography and size exclusion chromatographic (SEC) purification steps applied to 83A10-TCB antibody (3C). (3D) Additional purification steps: cation exchange chromatography (cIEX) and a final size exclusion chromatographic (re-SEC) steps applied to the final protein preparations in (3C). (3E) 83A10-TCBcv antibody after PA+cIEX+SEC purification steps. 83A10-TCB and 83A10-TCBcv molecules are both of molecular format as described in FIG. 2a of PCT/EP2015/067841 incorporated by reference.

FIGS. 3F-3K. Head-to-head comparison study: Production of 83A10-TCB without charge vs. 83A10-TCBcv with charge variant. Properties (e.g. purity, yield, monomer content) of 83A10-TCB and 83A10-TCBcv antibodies were measured side-by-side and compared after each purification steps 1) PA affinity chromatography only (3F, 3G), 2) PA affinity chromatography then SEC (3F, 3I) and 3) PA affinity chromatography then SEC then cIEX and re-SEC (3J, 3K). CE-SDS (non-reduced) graphs of the final protein solutions after the respective methods of purification for 83A10-TCB and 83A10-TCBcv antibodies. (3F) PA affinity chromatography purification step applied to 83A10-TCB antibody. (3G) PA affinity chromatography purification step applied to 83A10-TCBcv antibody. (3H) PA affinity chromatography+SEC purification steps applied to 83A10-TCB antibody. (3I) PA affinity chromatography+SEC purification steps applied to 83A10-TCBcv antibody. (3J) PA affinity chromatography+/−SEC+cIEX+SEC purification steps applied to 83A10-TCB antibody. (3K) PA affinity chromatography+/−SEC+cIEX+SEC purification steps applied to 83A10-TCBcv antibody. Purity, yield, monomer content were measured. Percentage of correct molecule detected by liquid chromatography-mass spectrometry (LC-MS).

FIG. 6. Internalization rates of TCB2+1 antibodies and anti-ROR1 IgG antibody (1 nM) in RPMI8226 MM cells after an incubation of 2 hrs at 37° C., as measured in two independent experiments as shown in FIG. 6 A and FIG. 6 B. The results demonstrate that anti-ROR1/anti-CD3 TCB2+1 has an internalization rate of less than 15% in RPMI cells.

FIG. 7. Binding of anti-ROR1/anti-CD3 TCB antibodies on Jurkat T cells. Mean fluorescence intensity for anti-ROR1/anti-CD3 T cell bispecific antibodies plotted in function of antibody concentrations (from 3 to 500 nM); anti-ROR1/anti-CD3 TCB1+1 and anti-ROR1/anti-CD3 TCB2+1 antibodies on Jurkat cells. EC50 values and maximal binding of anti-ROR1/anti-CD3 TCB1+1 and anti-ROR1/anti-CD3 TCB2+1 antibodies to Jurkat cells were not reached. DP47 isotype control antibody or anti-ROR1 IgG antibody did not bind to Jurkat T cells.

FIGS. 9A-9B. Up-regulation of T-cell activation markers by anti-ROR1/anti-CD3 TCB antibodies in presence of ROR1-positive (9A) Rec-1 cells and (9B) RPMI8226 cells. Mean fluorescence intensity plotted in function of antibody concentrations (from 0.01 pM to 100 nM). (9A) A concentration dependent increase in the mean fluorescence intensity of the late activation marker CD25 gated on CD8 T cells was observed in Rec-1 cells. Significant concentration dependent activation of CD8 T cells by anti-ROR1/anti-CD3 TCB1+1 antibody in the presence of ROR1-positive Rec-1 cells. Maximum signal reached at 100 pM of antibody. Unspecific activation of CD8 T cells was minimal upon binding of CD3 on T cells but without binding on ROR1-positive target cells by using non-binder TCB constructs. Activation of CD8 T cells was weak with anti-ROR1/anti-CD3 TCB2+1 antibody as shown by a faint but noticeable increase in CD25 mean fluorescence intensity. However, unspecific T cell activation could not be ruled out. (9B) Concentration dependent upregulation of CD25 on CD8 T cells mediated by anti-ROR1/anti-CD3 TCB1+1 and anti-ROR1/anti-CD3 TCB2+1 antibodies in the presence of ROR1-positive RPMI8226 MM cells. At the highest concentration (100 pM) of TCB antibodies tested there was no unspecific activation of CD8 T cells as shown with non-binder TCB constructs.

DETAILED DESCRIPTION OF THE INVENTION

Figure 1A:
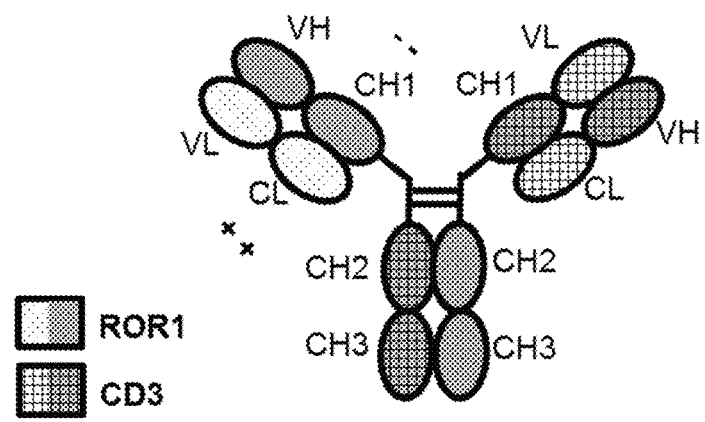
Figure 1B:
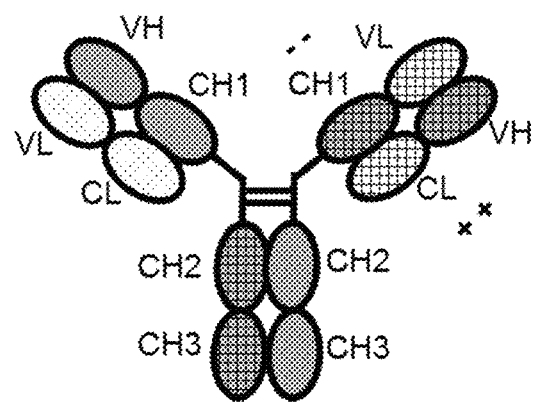

The inventors have found that bispecific antibodies against CD3ε and ROR1 with VH/VL exchange can be produced in high yield and easily purified if in the light chain CL of either the antibody portion against CD3ε or ROR1 the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat).

Preferably the VH/VL exchange is in the CD3 binding portion. Preferably the bispecific antibody is monovalent for CD3 binding. The amino acid substitutions described above can be either in the ROR1 binding portion or in the CD3 binding portion. Therefore in a certain embodiment of the invention the CD3 binding portion can comprise the VH/VL exchange and the amino acid substitutions. In this case the ROR1 binding portion does not comprise any VH/VL exchange or amino acid substitutions at amino acids 124, 147, 213, or 123. Preferably the bispecific antibody is monovalent for CD3 binding and bivalent for ROR1 binding. As described, the bispecific antibody can therefore comprise a second ROR1 binding portion, which is identical to the first one. Therefore if the first ROR1 binding portion comprises the amino acid substitutions, the second ROR1 binding portion comprises the same substitutions and if the first ROR1 binding portion does not comprise the amino acid substitutions, the second ROR1 binding portion does also not comprise the substitutions. Preferably amino acid 124 is K, amino acid 147 is E, amino acid 213 is E, and amino acid 123 is R. Preferably the CD3 binding portion and the ROR1 binding portion (or both ROR1 binding portions if so) are Fab fragments, whereby when two ROR1 binding portions are present one ROR1 portion is chemically linked to the CD3 binding portion via CH1/VL (C-terminus of ROR1 binding portion (CH1) to N-terminus of crossover CD3 binding portion (VL)) or CH1/VH (C-terminus of crossover CD3 binding portion (CH1) to N-terminus of ROR1 binding portion (VH)). The bispecific antibody can comprise or not comprise an Fc part.

The term "ROR1" as used herein relates to human ROR1 (synonyms: tyrosine-protein kinase transmembrane receptor ROR1, EC=2.7.10.1, neurotrophic tyrosine kinase, receptor-related 1, UniProtKB Q01973) which is a tyrosine-protein kinase receptor. The extracellular domain of ROR1 consists according to UniProt of amino acids 30-406. The term "antibody against ROR1, anti ROR1 antibody or ROR1 Mab" as used herein relates to an antibody specifically binding to human ROR1. The antibody binds specifically to the extracellular domain of ROR1 (amino acids M1-V406 of SEQ ID NO:1). The antibody binds specifically to fragments of the extracellular domain, which are the Ig-like C2-type domain (amino acids Q73-V139 of SEQ ID NO:1), the frizzled domain (amino acids E165-I299 of SEQ ID NO: 1), or the kringle domain (amino acids K312-C391 of SEQ ID NO:1). These fragments are mentioned in WO2005100605. It is further preferred that the antibody binds specifically to the extracellular domain fragment WNISSELNKDSYLTL (SEQ ID NO. 18) of ROR1. This fragment is mentioned in Daneshmanesh A H et al., Int. J. Cancer, 123 (2008) 1190-1195. Exemplary anti-ROR1 antibodies according to the invention are Mab2 (WO201209731, Mab 4A5) and Mab1, Mab3 and Mab4 (WO2012075158, Mabs R12, Y31 and R11). When not specified, ROR1 IgG or TCB antibodies referred to Mab1.

The term "CD3ε or CD3" as used herein relates to human CD3ε described under UniProt P07766 (CD3E_HUMAN).

```
                                              (SEQ ID NO: 63)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI
```

The term "antibody against CD3, anti CD3 antibody" relates to an antibody binding to CD3ε. Preferably the antibody comprises a variable domain VH comprising the heavy chain CDRs of SEQ ID NO: 12, 13 and 14 as respectively heavy chain CDR1, CDR2 and CDR3 and a variable domain VL comprising the light chain CDRs of SEQ ID NO: 15, 16 and 17 as respectively light chain CDR1, CDR2 and CDR3. Preferably the antibody comprises the variable domains of SEQ ID NO:10 (VH) and SEQ ID NO:11 (VL). Preferably the antibody comprises a variable domain VH comprising the heavy chain CDRs of SEQ ID NO: 23, 24 and 25 as respectively heavy chain CDR1, CDR2 and CDR3 and a variable domain VL comprising the light chain CDRs of SEQ ID NO: 26, 27 and 28 as respectively light chain CDR1, CDR2 and CDR3. Preferably the antibody comprises the variable domains of SEQ ID NO:21 (VH) and SEQ ID NO:22 (VL). The anti-CD3 antibodies shown in SEQ ID NO:10 and 11 and 21 and 22 are derived from SP34 and have similar sequences and the same properties in regard to epitope binding as antibody SP34.

"Specifically binding to CD3 or ROR1" refer to an antibody that is capable of binding CD3 or ROR1 (the targets) with sufficient affinity such that the antibody is useful as a therapeutic agent in targeting CD3 or ROR1. In some embodiments, the extent of binding of an anti-CD3 or ROR1 antibody to an unrelated, non-CD3 or non-ROR1 protein is about 10-fold preferably >100-fold less than the binding of the antibody to CD3 or ROR1 as measured, e.g., by surface plasmon resonance (SPR) e.g. Biacore®, enzyme-linked immunosorbent (ELISA) or flow cytometry (FACS). Preferably the antibody that binds to CD3 or ROR1 has a dissociation constant (Kd) of $10^{-8}$ M or less, preferably from $10^{-8}$ M to $10^{-13}$ M, preferably from $10^{-9}$ M to $10^{-13}$ M. Preferably the bispecific antibody according to the invention binds to an epitope of ROR1 that is conserved among ROR1 from different species and/or an epitope of CD3 that is conserved among CD3 from different species, preferably among human and cynomolgus. "Bispecific antibody specifically binding to CD3 and ROR1" or "antibody according to the invention" refers to a respective definition for binding to both targets. An antibody specifically binding to ROR1 (or CD3 or ROR1 and CD3) does not bind to other human antigens. Therefore in an ELISA, OD values for such unrelated targets will be equal or lower to that of the limit of detection of the specific assay, preferably equal or lower as 1.5 pM, or equal or lower to OD values of control samples without plate-bound-ROR1 or with untransfected HEK293 cells.

Antibodies according to the invention are analyzed by ELISA for binding to human ROR1 using plate-bound ROR1. For this assay, an amount of plate-bound ROR1 preferably or 1.5 nM and concentration(s) preferably ranging from 1 pM to 200 nM of anti-ROR1 antibody are used. An antibody according to the invention for which its ROR1 binding is at least 20% higher than the OD values of the control samples without plate-bound ROR1 or with untransfected HEK293 cells according to the invention is an antibody "binding to human ROR1 in an ELISA assay". An exemplary antibody according to the invention is characterized by the heavy and light chain set of polypeptides SEQ ID NO:37, 38, 39, and 40. Another exemplary antibody according to the invention is characterized by the heavy and light chain set of polypeptides SEQ ID NO:37, 38, 39, and 41.

The term "antibody according to the invention which does not internalize" as used herein means a bispecific antibody according to the invention with MFI reduction properties characterized in that in a cell based assay at 37° C. during 2 hrs., using ROR1-positive B-CLL cells, and used at an antibody concentration of 1 nM, whereby not internalize means, that the mean fluorescence intensity (MFI), as detected by flow cytometry, upon binding to ROR1-positive cells measured at time 0 is not reduced more than 50%, preferably not more than 30% by internalization when re-measured after a 2 hr-incubation at 37° C. The bispecific antibody according to the invention does not internalize in ROR1-positive B-CLL cells, therefore the binding of the said anti-ROR1 antibody to ROR1-positive B-CLL cells is not reduced more than 50%, preferably not more than 30%, when the said antibody is incubated at 37° C. for 2 h in such cell based assay as described herein.

It is also preferred, that a bispecific antibody according to the invention shows in a cell based assay at 37° C. during 2 hrs, using ROR1-positive B-CLL cells, and at an antibody concentration of 1 nM, a decrease in the mean fluorescence intensity by internalization from time 0 to 2 hrs at 37° C. ($\Delta$MFI), as measured by flow cytometry is between 120% to 0%, preferably from 100% to 0%, of the $\Delta$MFI of an anti-ROR1 bivalent antibody of human IgG1 kappa ($\kappa$) type comprising as light chain variable domain (VL) the sequence of SEQ ID NO:2 and as variable heavy chain domain (VH) the sequence of SEQ ID NO:6, in the same concentration and experimental conditions.

For a therapy using a T cell bispecific antibody comprising an anti-ROR1 antibody, it is preferred that the antibody does not internalize as defined above for facilitating a stable immune synapse between the tumor cell and the T cell and effective T cell-mediated redirected cytotoxicity.

The term "reduction of mean fluorescence intensity" ($\Delta$MFI) reflecting the internalization of the said anti-ROR1 antibody to ROR1-positive cells" or "MFI reduction" as used herein refers to the percentage of MFI reduction as calculated for each ROR1 antibodies relative to the unspecific human IgG control ($MFI_{background}$) and ROR1 antibodies maintained on ice ($MFI_{max}$) by using the formula $\Delta MFI = 100 - 100 \times [(MFI_{experimental} - MFI_{background})/(MFI_{max} - MFI_{background})]$. $MFI_{experimental}$ is the MFI measured with said ROR1 antibody after 2 h incubation at 37° C. An MFI reduction which is at least 75% blocked and reversed by 10 µM endocytosis inhibitor phenylarsine oxide is for example caused by antibody internalization while an MFI reduction which is not blocked by phenylarsine oxide is caused by antibody dissociation. Internalizing anti-ROR1 antibodies are known in the state of the art (Baskar et al., Clin. Cancer Res., 14(2): 396-404 (2008)).

Preferably the bispecific antibody according to the invention is characterized in that an increase in MFI value at time 2 hrs in the presence of 3 µM phenylarsine oxide (PAO) as compared to MFI value at time 2 hrs in the absence of PAO is not more than 30%, preferably not more than 20%, preferably not more that 10%, even not more than detection level of the MFI value at time 0.

The term "target" as used herein means either ROR1 or CD3. The term "first target and second target" means either CD3 as first target and ROR1 as second target or means ROR1 as first target and CD3 as second target.

The term "antibody" as used herein refers to a monoclonal antibody. An antibody consists of two pairs of a "light chain" (LC) and a "heavy chain" (HC) (such light chain (LC)/heavy chain pairs are abbreviated herein as LC/HC). The light chains and heavy chains of such antibodies are polypeptides consisting of several domains. Each heavy chain comprises a heavy chain variable region (abbreviated herein as HCVR or VH) and a heavy chain constant region. The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain VL and a light chain constant domain CL. The variable domains VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The "constant domains" of the heavy chain and of the light chain are not involved directly in binding of an antibody to a target, but exhibit various effector functions.

The "light chain of an antibody" as used herein is a polypeptide comprising in N-terminal to C-terminal direction a light chain variable domain (VL), and a light chain constant domain (CL), abbreviated as VL-CL. A "crossover light chain (VH-CL)" as used herein is a light chain wherein the VL domain is replaced by the respective VH domain. "The "heavy chain of an antibody" as used herein is a polypeptide comprising in N-terminal to C-terminal direction a heavy chain variable domain (VH) and a constant heavy chain domain 1 (CH1). A "crossover heavy chain (VL-CH1)" as used herein is a heavy chain wherein the VH domain is replaced by the respective VL domain.

There exist several approaches for CH3-modifications to enforce the heterodimerization, which are well described e.g. in WO96/27011, WO98/050431, EP1870459, WO2007/110205, WO2007/147901, WO2009/089004, WO2010/129304, WO2011/90754, WO2011/143545, WO2012058768, WO2013157954, WO2013096291. Typically in all such approaches the first CH3 domain and the second CH3 domains are both engineered in a complementary manner so that each CH3 domain (or the heavy chain comprising it) cannot longer homodimerize with itself but is forced to heterodimerize with the complementary engineered other CH3 domain (so that the first and second CH3 domain heterodimerize and no homodimers between the two first or the two second CH3 domains are formed). These different approaches for improved heavy chain heterodimerization are contemplated as different alternatives in combination with the heavy-light chain modifications (VH and VL exchange/replacement in one binding arm and the introduction of substitutions of charged amino acids with opposite charges in the CH1/CL interface) in the antibodies according to the invention which reduce light chain mispairing, e.g. Bence-Jones type side products.

In one preferred embodiment of the invention, aa substitution or charge variant is applied to the constant domain CL at positions 123 and 124 and/or to the constant domain CH1 at positions 147 and 213 in the antibodies according to the invention which reduce light chain mispairing.

In one preferred embodiment of the invention (in case the antibody according to the invention comprises CH3 domains in the heavy chains) the CH3 domains of said multispecific antibody according to the invention can be altered by the "knob-into-holes" technology which is described in detail with several examples in e.g. WO 96/027011, Ridgway, J. B., et al., Protein Eng. 9 (1996) 617-621; and Merchant, A. M. et al., Nat. Biotechnol. 16 (1998) 677-681; WO98/050431. In this method the interaction surfaces of the two CH3 domains are altered to increase the heterodimerisation of both heavy chains containing these two CH3 domains. Each of the two CH3 domains (of the two heavy chains) can be the "knob", while the other is the "hole".

Thus in one embodiment of the invention said antibody according to the invention (comprises a CH3 domain in each heavy chain and) is further characterized in that the first CH3 domain of the first heavy chain of the antibody under a) and the second CH3 domain of the second heavy chain of the antibody under b) each meet at an interface which comprises an original interface between the antibody CH3 domains, wherein said interface is altered to promote the formation of the antibody according to the invention, wherein the alteration is characterized in that:

i) the CH3 domain of one heavy chain is altered, so that within the original interface of the CH3 domain of one heavy chain that meets the original interface of the CH3 domain of the other heavy chain within the antibody according to the invention, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and ii) the CH3 domain of the other heavy chain is altered, so that within the original interface of the second CH3 domain that meets the original interface of the first CH3 domain within the antibody according to the invention an amino acid residue is replaced with an amino acid residue having a smaller side chain volume, thereby generating a cavity within the interface of the second CH3 domain within which a protuberance within the interface of the first CH3 domain is positionable.

Preferably said amino acid residue having a larger side chain volume is selected from the group consisting of arginine (R), phenylalanine (F), tyrosine (Y), tryptophan (W).

In one aspect of the invention both CH3 domains are further altered by the introduction of cysteine (C) as amino acid in the corresponding positions of each CH3 domain such that a disulfide bridge between both CH3 domains can be formed.

Other techniques for CH3-modifications to enforcing the heterodimerization are contemplated as alternatives of the invention and described e.g. in WO96/27011, WO98/050431, EP1870459, WO2007/110205, WO2007/147901, WO2009/089004, WO2010/129304, WO2011/90754, WO2011/143545, WO2012/058768, WO2013/157954, WO2013/157953, WO2013/096291.

In one embodiment the antibody according to the invention is of IgG2 isotype and the heterodimerization approach described in WO2010/129304 can be used alternatively.

The term "antibody" includes e.g. mouse antibodies, human antibodies, chimeric antibodies, humanized antibodies and genetically engineered antibodies (variant or mutant antibodies) as long as their characteristic properties are retained. Especially preferred are human or humanized antibodies, especially as recombinant human or humanized antibodies. The terms "monoclonal antibody" or "monoclonal antibody composition" as used herein refer to a preparation of antibody molecules of a single amino acid composition.

The term "comprising" in regard to the bispecific antibody as used herein means that the bispecific antibody comprises as CD3 and ROR1 binders only those binders mentioned. Therefore a bispecific antibody according the invention comprising a monovalent anti-ROR1 antibody specifically binding to ROR1, and a monovalent antibody specifically binding to CD3 has in regard to CD3 and ROR1 binding only one binding valence for CD3 and only one valence for ROR1 and is therefore bivalent. A bispecific antibody according the invention comprising a bivalent anti-ROR1 antibody specifically binding to ROR1, and a monovalent antibody specifically binding to CD3 has in regard to ROR1 binding two binding valences and in regard to CD3 binding one valence and is therefore trivalent. Preferably the monovalent antibody specifically binding to CD3 is covalently linked at its C-terminus to the N-terminus of one variable chain of the antibody specifically binding to ROR1.

A "Fab fragment of an antibody" as used herein is a fragment on an antibody that binds to antigens. A Fab fragment of an antibody consists of two pairs of domains. In a wild-type antibody it is composed of one constant and one variable domain of each of the heavy chain (CH1 and VH) and the light chain (CL and VL). According to the invention such domain pairs can be, due to a crossover, also VH-CL and VL-CH1. In a wild-type antibody and according to the invention the domain of the heavy and light chain domain pairs of a Fab fragment are not chemically linked together and are therefore not scFvs (single chain variable fragments). "Crossover" according to the invention means that preferably in one Fab the domains VL and VH are replaced by each other. The term "Fab fragment" also includes parts or all of the hinge region, like Fab' fragment. As used herein, "F(ab)₂ fragment" refers to a bivalent monospecific antibody fragment preferably with a Fc part.

The term "aa substitution or charge variant" as used herein means amino acid substitution according to the invention in that in a constant domain CL the amino acid at position 124 is substituted independently by lysine (K), arginine (R) or histidine (H) (numbering according to Kabat), and wherein in the respective constant domain CH1 the amino acid at position 147 and the amino acid at position 213 is substituted independently by glutamic acid (E), or aspartic acid (D), and preferably in addition in the constant domain CL in the amino acid at position 123 is substituted independently by lysine (K), arginine (R) or histidine (H) and preferably by arginine (R).

A preferred combination of aa substitution is Q124K, E123R, K147E and K213E (for example: E123R means that glutamic acid (E) at position 123 is replaced by arginine (R). Preferably a F(ab)₂ fragment is linked at the C-terminus by disulphide bond(s) in the hinge region and usually such a "F(ab)₂ fragment" is a F(ab')₂ fragment. A preferred combination of aa substitution is E124K, E123K, K147E and K213E (for example: E123K means that glutamic acid (E) at position 123 is replaced by lysine (K). Preferably a F(ab)₂ fragment is linked at the C-terminus by disulphide bond(s) in the hinge region and usually such a "F(ab)₂ fragment" is a F(ab')₂ fragment. Introduction of substitutions of charged amino acids with opposite charges in the constant domains CH1/CL of the antibodies according to the invention reduces light chain mispairing.

The term "ROR1 Fab" as used within the invention denotes a Fab fragment of the antibody specifically binding to ROR1. Due to the exchange of either the variable regions or the constant regions in the anti-ROR1 antibody Fab fragment (ROR1 Fab), such ROR1 Fab is referred to as "ROR1cross Fab" or "crossover ROR1 Fab fragment" According to the invention the ROR1 Fab is not a ROR1crossFab. By "connected" is meant that the Fab fragments are preferably linked by peptide bonds, either directly or via one or more peptide linker. The term "CD3 Fab" as used within the invention denotes a Fab fragment of the antibody specifically binding to CD3. The CD3 Fab is linked at its N-terminus the C-terminus of the ROR1 Fab. Due to the exchange of either the variable regions or the constant regions in the CD3 Fab, such CD3 Fab is referred to as "CD3 crossFab" or "crossover CD3 Fab fragment". According to the invention the CD3 Fab is preferably a crossFab.

The term "peptide linker" as used within the invention denotes a peptide with amino acid sequences, which is preferably of synthetic origin. These peptide linkers according to invention are used to connect one of the Fab fragments to the C- or N-terminus of the other Fab fragment to form a multispecific antibody according to the invention. Preferably said peptide linkers are peptides with an amino acid sequence with a length of at least 5 amino acids, preferably with a length of 5 to 100, more preferably of 10 to 50 amino acids. In one embodiment said peptide linker is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. Additionally, linkers may comprise (a portion of) an immunoglobulin hinge region. In one embodiment said peptide linker is (G₄S)₂ (SEQ ID: NO 19).

There are five types of mammalian antibody heavy chains denoted by the Greek letters: α, δ, ε, γ, and μ (Janeway C A, Jr et al (2001). Immunobiology. 5th ed., Garland Publishing). The type of heavy chain present defines the class of antibody; these chains are found in IgA, IgD, IgE, IgG, and IgM antibodies, respectively (Rhoades R A, Pflanzer R G (2002). Human Physiology, 4th ed., Thomson Learning). Distinct heavy chains differ in size and composition; α and γ contain approximately 450 amino acids, while and c have approximately 550 amino acids. Each heavy chain has two regions, the constant region and the variable region. The constant region is identical in all antibodies of the same isotype, but differs in antibodies of different isotype. Heavy chains γ, α and δ have a constant region composed of three constant domains CH1, CH2, and CH3 (in a line), and a hinge region for added flexibility (Woof J, Burton D Nat Rev Immunol 4 (2004) 89-99); heavy chains μ and ε0 have a constant region composed of four constant domains CH1, CH2, CH3, and CH4 (Janeway C A, Jr et al (2001). Immunobiology. 5th ed., Garland Publishing). The variable region of the heavy chain differs in antibodies produced by different B cells, but is the same for all antibodies produced by a single B cell or B cell clone. The variable region of each heavy chain is approximately 110 amino acids long and is composed of a single antibody domain. In mammals there are only two types of light chain, which are called lambda (λ) and kappa (κ). A light chain has two successive domains: one constant domain CL and one variable domain VL. The approximate length of a light chain is 211 to 217 amino acids.

A bispecific antibody according to the invention, which comprises a Fc part, can be of any class (e.g. IgA, IgD, IgE, IgG, and IgM, preferably IgG or IgE), or subclass (e.g., IgG1, IgG2, IgG3, IgG4, IgA1 and IgA2, preferably IgG1), whereby both antibodies, from which the bivalent bispecific antibody according to the invention is derived, have an Fc part of the same subclass (e.g. IgG1, IgG4 and the like, preferably IgG1), preferably of the same allotype (e.g. Caucasian).

A "Fc part of an antibody" is a term well known to the skilled artisan and defined on the basis of papain cleavage of antibodies. The antibodies according to the invention, which comprise an Fc part, contain as Fc part, preferably a Fc part derived from human origin and preferably all other parts of the human constant regions. The Fc part of an antibody is directly involved in complement activation, C1q binding, C3 activation and Fc receptor binding. While the influence of an antibody on the complement system is dependent on certain conditions, binding to C1q is caused by defined binding sites in the Fc part. Such binding sites are known in the state of the art and described e.g. by Lukas, T J., et al., J. Immunol. 127 (1981) 2555-2560; Brunhouse, R., and Cebra, J. J., MoI. Immunol. 16 (1979) 907-917; Burton, D. R., et al., Nature 288 (1980) 338-344; Thommesen, J. E., et al., MoI. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat, see below). Antibodies of subclass IgG1, IgG2 and IgG3 usually show complement activation, C1q binding and C3 activation, whereas IgG4 do not activate the complement system, do not bind C1q and do not activate C3. Preferably the Fc part is a human Fc part. Preferably the Fc part is a human IgG1Fc part. Preferably the antibody according to the invention comprises in the human IgG1 Fc part amino acid substitution of Pro329 with glycine or arginine and/or substitutions L234A and L235A, preferably Pro329 with glycine and substitutions L234A and L235A.

Preferably the bispecific antibody according to the invention comprising constant heavy regions CH2/CH3 of IgG1 subclass is characterized in comprising the mutations L234A, L235A and P329G (numbering according to EU index of Kabat) to avoid FcR and C1q binding and minimizing ADCC/CDC. The advantage is that such an antibody of the invention mediates its tumor cell killing efficacy purely by the powerful mechanism of T-cell redirection/activation. Additional mechanisms of action like effects on complement system and on effector cells expressing FcR are avoided and the risk of side-effects is decreased.

Preferably the antibody according to the invention comprises as Fc part an Fc variant of a wild-type human IgG Fc region, said Fc variant comprising an amino acid substitution at position Pro329 and at least one further amino acid substitution, wherein the residues are numbered according to the EU index of Kabat, and wherein said antibody exhibits a reduced affinity to the human FcγRIIIA and/or FcγRIIA and/or FcγRI compared to an antibody comprising the wildtype IgG Fc region, and wherein the ADCC induced by said antibody is reduced to at least 20% of the ADCC induced by the antibody comprising a wild-type human IgG Fc region. In a specific embodiment Pro329 of a wild-type human Fc region in the antibody according to the invention is substituted with glycine or arginine or an amino acid residue large enough to destroy the proline sandwich within the Fc/Fcγ receptor interface, that is formed between the proline329 of the Fc and tryptophane residues Trp 87 and Trp 110 of FcγRIII (Sondermann et al.: Nature 406, 267-273 (20 Jul. 2000)). In a further aspect of the invention the at least one further amino acid substitution in the Fc variant is S228P, E233P, L234A, L235A, L235E, N297A, N297D, or P331S and still in another embodiment said at least one further amino acid substitution is L234A (denotes that leucine 234 is substituted by alanine) and L235A of the human IgG1 Fc region or S228P and L235E of the human IgG4 Fc region. Such Fc variants are described in detail in WO2012130831.

The constant heavy chain of an antibody according to the invention is preferably of human IgG1 type and the constant light chain is preferably of human lambda (λ) or kappa (κ) type, preferably of human kappa (κ) type.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the targets noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon target challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole et al. and Boerner et al. are also available for the preparation of human monoclonal antibodies (Cole et al., Monoclonal Antibodies and Cancer Therapy, Alan R. Liss, p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The "variable domain" (variable domain of a light chain (VL), variable region of a heavy chain (VH)) as used herein denotes each of the pair of light and heavy chains which is involved directly in binding the antibody to the target. The domains of variable human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the target binding site. The antibody heavy and light chain CDR3 regions play a particularly important role in the binding specificity/affinity of the antibodies according to the invention and therefore provide a further object of the invention.

The terms "hypervariable region" or "target-binding portion of an antibody" when used herein refer to the amino acid residues of an antibody which are responsible for target-binding. The hypervariable region comprises amino acid residues from the "complementarity determining regions" or "CDRs". "Framework" or "FR" regions are those variable domain regions other than the hypervariable region residues as herein defined.

Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to target binding. CDR and FR regions are determined according to the standard definition of Kabat et al., Sequences of Proteins of Immunological Interest, 5th ed., Public Health Service, National Institutes of Health, Bethesda, MD (1991).

The term "target" or "target molecule" as used herein are used interchangeable and refer to human ROR1 and human CD3ε.

The term "epitope" includes any polypeptide determinant capable of specific binding to an antibody. In certain embodiments, epitope determinant include chemically active surface groupings of molecules such as amino acids, sugar side chains, phosphoryl, or sulfonyl, and, in certain embodiments, may have specific three dimensional structural characteristics, and or specific charge characteristics. An epitope is a region of a target that is bound by an antibody.

In general there are two vectors encoding the light chain and heavy chain of said antibody specifically binding to the first target, and further two vectors encoding the light chain and heavy chain of said antibody specifically binding to the second target. One of the two vectors is encoding the respective light chain and the other of the two vectors is encoding the respective heavy chain. However in an alternative method for the preparation of a bispecific antibody according to the invention, only one first vector encoding the light chain and heavy chain of the antibody specifically binding to the first target and only one second vector encoding the light chain and heavy chain of the antibody specifically binding to the second target can be used for transforming the host cell.

The term "nucleic acid or nucleic acid molecule", as used herein, is intended to include DNA molecules and RNA molecules. A nucleic acid molecule may be single-stranded or double-stranded, but preferably is double-stranded DNA.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham and Van der Eh, Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen S N, et al, PNAS 1972, 69 (8): 2110-2114.

Recombinant production of antibodies using transformation is well-known in the state of the art and described, for example, in the review articles of Makrides, S. C, Protein Expr. Purif. 17 (1999) 183-202; Geisse, S., et al., Protein Expr. Purif. 8 (1996) 271-282; Kaufman, R J., Mol. Biotechnol. 16 (2000) 151-161; Werner, R. G., et al., Arzneimittelforschung 48 (1998) 870-880 as well as in U.S. Pat. Nos. 6,331,415 and 4,816,567.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

The bispecific antibodies according to the invention are preferably produced by recombinant means. Such methods are widely known in the state of the art and comprise protein expression in prokaryotic and eukaryotic cells with subsequent isolation of the antibody polypeptide and usually purification to a pharmaceutically acceptable purity. For the protein expression, nucleic acids encoding light and heavy chains or fragments thereof are inserted into expression vectors by standard methods. Expression is performed in appropriate prokaryotic or eukaryotic host cells like CHO cells, NSO cells, SP2/0 cells, HEK293 cells, COS cells, yeast, or E. coli cells, and the antibody is recovered from the cells (supernatant or cells after lysis). The bispecific antibodies may be present in whole cells, in a cell lysate, or in a partially purified or substantially pure form. Purification is performed in order to eliminate other cellular components or other contaminants, e.g. other cellular nucleic acids or proteins, by standard techniques, including alkaline/SDS treatment, column chromatography and others well known in the art. See Ausubel, F., et al., ed., Current Protocols in Molecular Biology, Greene Publishing and Wiley Interscience, New York (1987).

Expression in NS0 cells is described by, e.g., Barnes, L. M., et al., Cytotechnology 32 (2000) 109-123; and Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous.

Linking is accomplished by ligation at convenient restriction sites. If such sites do not exist, the synthetic oligonucleotide adaptors or linkers are used in accordance with conventional practice.

The bispecific antibodies are suitably separated from the culture medium by conventional immunoglobulin purification procedures such as, for example, protein A-SEPHAROSE® (SEPHAROSE® is a registered mark of General Electric Corporation which designates high molecular weight substance for the separation by gel filtration of macromolecules that range in weight from about 100,000 to several million), hydroxylapatite chromatography, gel electrophoresis, dialysis, or affinity chromatography. DNA or RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and target binding, but may improve the yield of the recombinant production, protein stability or facilitate the purification.

T cell bispecific (TCB) binders have very high concentration/tumor-cell-receptor-occupancy dependent potency in cell killing (e.g. $EC_{50}$ in in vitro cell killing assays in the sub- or low picomolar range; Dreier et al. Int J Cancer 2002), T-cell bispecific binder (TCB) are given at much lower doses than conventional monospecific antibodies. For example, blinatumomab (CD19×CD3) is given at a continuous intravenous dose of 5 to 15 µg/m²/day (i.e. only 0.035 to 0.105 mg/m²/week) for treatment of acute lymphocytic leukemia or 60 µg/m²/day for treatment of Non Hodgkin Lymphoma, and the serum concentrations at these doses are in the range of 0.5 to 4 ng/ml (Klinger et al., Blood 2012; Topp et al., J Clin Oncol 2011; Goebeler et al. Ann Oncol 2011). Due to the very short elimination half life of blinatumomab clinical administration is via continuous infusion via pump carried at the patients body. Due to longer elimination half life of the antibodies of this invention it is envisaged that for an antibody according to the invention subcutaneous administration is possible and preferred in the clinical settings (preferably in the dose range of 0.1 to 10 mg/m² once or twice a week, preferably even lower doses). Even at these low concentrations/doses/receptor occupancies, TCB can cause considerable adverse events (Klinger et al., Blood 2012). Improved pharmacokinetics properties of the antibodies of the invention are one measure to potentially reduce adverse events.

In principle it is possible to produce bispecific antibodies against CD3 and ROR1 in all formats known in the state of the art. A wide variety of recombinant bispecific antibody formats have been developed in the recent past, e.g. by fusion of, e.g. an IgG antibody format and single chain domains (see e.g. Kontermann RE, mAbs 4:2, (2012) 1-16). Bispecific antibodies wherein the variable domains VL and VH or the constant domains CL and CH1 are replaced by each other are described in WO2009080251 and WO2009080252. Antibody formats and formats of bispecific and multispecific antibodies are also pepbodies (WO200244215), Novel Antigen Receptor ("NAR") (WO2003014161), diabody-diabody dimers "TandAbs" (WO2003048209), polyalkylene oxide-modified scFv (U.S. Pat. No. 7,150,872), humanized rabbit antibodies (WO2005016950), synthetic immunoglobulin domains (WO2006072620), covalent diabodies (WO2006113665), flexibodies (WO2003025018), domain antibodies, dAb (WO2004058822), vaccibody (WO2004076489), antibodies with new world primate framework (WO2007019620), antibody-drug conjugate with cleavable linkers (WO2009117531), IgG4 antibodies with hinge region removed (WO2010063785), bispecific antibodies with IgG4 like CH3 domains (WO2008119353), camelid Antibodies (U.S. Pat. No. 6,838,254), nanobodies (U.S. Pat. No. 7,655, 759), CAT diabodies (U.S. Pat. No. 5,837,242), bispecific scFv2 directed against target antigen and CD3 (U.S. Pat. No. 7,235,641)), sIgA plAntibodies (U.S. Pat. No. 6,303,341), minibodies (U.S. Pat. No. 5,837,821), IgNAR (US2009148438), antibodies with modified hinge and Fc regions (US2008227958, US20080181890), trifunctional antibodies (U.S. Pat. No. 5,273,743), triomabs (U.S. Pat. No. 6,551,592), troybodies (U.S. Pat. No. 6,294,654).

An antibody according to the invention can be administered once or twice a week s.c. administration.

A bispecific trivalent antibody according to the invention has advantages on the potency, predictability for efficacy and safety.

An antibody according to the invention with bivalency to ROR1 and monovalency to CD3 favors binding to the tumor target ROR1 on malignant cells over CD3ε on T cells in circulation and avoids CD3 sink, thus increasing drug exposure in the tumor.

The following examples, sequence listing and figures are provided to aid the understanding of the present invention, the true scope of which is set forth in the appended claims. It is understood that modifications can be made in the procedures set forth without departing from the spirit of the invention.

| SEQ NO: | Name | aa sequence |
|---|---|---|
| 1 | ROR1 extracellular domain | MHRPRRRGTRPPLLALLAALLLAARGAAAOETELS VSAELVPTSSWNISSELNKDSYLILDEPMNNITTSL GQTAELHCKVSGNPPPTIRWFKNDAPVVQEPRRLS FRSTIYGSRLRIRNLDTTDIGNTQCVAINGKEVVSS TGVLFVKFGPPPTASPGYSDEYEEDGFCQPYRGIAC ARFIGNRTVYMESLIIMQGEIENQITAAFTMIGTSSII LSDKCSOFAIPSLCHYAFPYCDETSSVPKPRDLCRD ECEILENVLCQTEYIFARSNPMILMRLKLPNCEDLP QPESPEAANCIRIGIPMADPINKNHKCYNSTGVDYR GTVSVTKSGRQCQPWNSQYPFMITFTALRFPELNG GHSYCRNPGNQKEAPWCFTLDENFKSDLCDIPACD SKDSKEKNKMEILYILVPSVAIPLAIALLFFFICVCR NNOKSSSAPVOROPKHVRGONVEMSMLNAYKPKS ICAKELPLSAVIUMEELGECAFGKIYKGHLYLPGMD PIAQILVAIKTLKDYNNPQQWTERWASLMAELHII PNIVCLLGAVTQEQPVCMLFEYINQGDLHEFLIMRS PHSDVGCSSDEDGPIKSSLDHGDFLHIAIQIAAGME YLSSHFPVHKDLAARNILIGEQLHVKISDLGLSREIY SADYYRVQSKSLLPIRWMPPEAIMYGKFSSDSDIW SFGVNILWEIFSFGLQPYYGPSNOEVIENIVRKRQLLP CSEDCPPRMYSLMTECWNEIPSRRPRFKDIFIVRLRS WEGLSSIITSSTTPSGGNATTQTTSLSASPVSNLSNP RYPNYMPPSQGITPQGQIAGFIGPPIPQNQRFIPINGY PIPPGYAAPPAAHYQPTGPPRVIQHCPPPKSRSPSSA SGSTSTGFIVISLPSSGSNQEANIPLLPHMSIPNHPGG MGFIVFGNKSQKPYKIDSKQASLLGDANIHGHTES MISAEL |
| 2 | Mab ROR1 VL | ELVLTQSPSVSAALGSPAKITCTLSSAFIKTDTIDWY QQLQGEAPRYLMOVQSDGSYTKRPGVPDRFSGSSS GADRYLIIPSVQADDEADYYCGADYIGGYVFGGGT QLTVTG |
| 3 | CDR1L | MSSAFIKTDTID |
| 4 | CDR2L | GSYTKRP |
| 5 | CDR3L | GADYIGGYV |
| 6 | Mab ROR1 VH | QEQLVESGGRLVTPGGSLTLSCKASGFDFSAYYMS WVRQAPGKGLEWIATIYPSSGKTYYATWVNGRFTI SSDNAQNTVDLQMNSLTAADRATYFCARDSYADD GALFNIWGPGTLVTISS |
| 7 | CDR1H | AYYMS |
| 8 | CDR2H | TIYPSSGKTYYATWVNG |
| 9 | CDR3H | DSYADDGALFNI |
| 10 | MaB CD3 VH (H2C) | EVQLVESGGGLVQPGGSLKLSCAASGFTFNKYAM NWVRQAPGKGLEWVARIRSKYNNYATYYADSVK DRFTISRDDSKNTAYLQMNNLKTEDTAVYYCVRH GNFGNSYISYWAYWGQGTLVTVSS |
| 11 | MaB CD3 VL (H2C) | QTVVTQEPSLTVSPGGTVTLTCGSSTGAVTSGYYP NWVQQKPGQAPRGLIGGTKFLAPGTPARFSGSLLG GKAALTLSGVQPEDEAEYYCALWYSNRWVFGGG TKLTVL |
| 12 | CDR1H (H2C) | GFTENKYAMN |
| 13 | CDR2H (H2C) | RIRSKYNNYATYYADSVKD |
| 14 | CDR3H (H2C) | FIGNFGNSYISYWAY |
| 15 | CDR1L (H2C) | GSSTGAVTSGYYPN |
| 16 | CDR2L (H2C) | GIKFLAP |
| 17 | CDR3L (H2C) | ALWYSNRWV |
| 18 | Extracellular fragment of ROR1 | WNISSELNKDSYLTL |
| 19 | Linker | GGGGSGGGGS |

-continued

| SEQ NO: | Name | aa sequence |
|---|---|---|
| 20 | Intracellular fragment of ROR1 | KSQKPYKDSKQAS |
| 21 | Mab CD3 VH (CH2527) | EVQLLESGGGLVQPGGSLRLSCAASGFTESTYAMN<br>WVRQAPGKGLEWVSRIRSKYNNYATYYADSVKG<br>RFFISRDDSKNTLYLQMNSLRAEDTAVYYCVRHG<br>NFGNSYVSWFAYWGQGTLVTVSS |
| 22 | Mab CD3 VL (CH2527) | QAVVTQEPSLTVSPGGTVTLTCGSSTGAVTTSNYA<br>NWVQEKPGQAFRGLIGGTNKRAPGTPARFSGSLLG<br>GKAALTLSGAQPEDEAEYYCALWYSNLWVFGGGT<br>KLIVL |
| 23 | CDR1H (CH2527) | TYAMN |
| 24 | CDR2H (CH2527) | RIRSKYNNYATTYADSVKG |
| 25 | CDR3H (CH25:27) | HGNFGNSYVSWFAY |
| 26 | CDRL1 (CH2527) | GSSTGAVTTSNYAN |
| 27 | CDRL2 (CH2527) | GTNKRAP |
| 28 | CDRL3 (CH2527) | ALWYSNLWV |
| 29 | ROR1 hum IgG1 HC LALA PG | QEQLVESGGRLVTPGGSLTLSCKASGFDFSAYYMS<br>WVRQAPGKGLEWIATIYPSSGKFYYATWVNGRFTI<br>SSDNAQNTVDLQMNSLTAADRATYFCARDSYADD<br>GALFNIWGPGTLVTISSASTKGPSVFPLAPSSKSTSG<br>GTAALGCLVKDYFPEPVTVSWNSGALTSGVHTFPA<br>VLQSSGLYSLSSVVTVPSSSLGTQTYICNVNHKPSN<br>TKVDKKVEPKSCDKTHTCPPCPAPEAAGGPSVFLF<br>PPKPKIYFLMISRTPEVTCVVVDVSHEDPEVKFNWY<br>VDGVEVHNAKTKPREEQYNSTYRVNISVLXVLHQD<br>WLNGKEYKCKVSNICALGAPIEKTISICkKGQPREPQ<br>VYTLPPSRDELTKNQVSLTCLVKGEYPSDIAVEWES<br>NGQPENNYKTTPPVLDSDGSFFLYSKLTVDKSRWQ<br>QGNVITSCSVMHEALEINHYTQKSLSLSPGK |
| 30 | ROR1 hum IgG1 LC | MGWSCIILFLVATATGVHSELVLTQSPSVSAALGSP<br>AKITCTLSSAHKIDTIDWYQQLQGEAPRYLMQVQS<br>DGSYTKRPGVPDRFSGSSSGADRYLLIPSVQADDEA<br>DYYCGADYIGGYVEGGGTQLTVLGQPKAAPSVTL<br>FPPSSEELQANKATLVCLISDFYPGAVTVAWKADS<br>SPVKAGVETFTPSKQSNNKYAASSYLSILIPEQWKS<br>HRSYSCQVTHEGSTVEKTVAPTECS |
| 31 | ROR1 x CD3 VH_CL HC knob LALA PG | QEQLVESGGRLVTPGGSLTLSCKASGFDFSAYYMS<br>WVRQAPGKGLEWIATIYPSSGKTYYATWVNGRFTI<br>SSDNAQNTVDLQMNSLTAADRATYFCARDSYADD<br>GALFNIWGPGTLVTISSNSTKGPSVFPLAPSSKSISG<br>GTAALGCLVKDYFPEPVTVSWNSGALTSGVHTFPA<br>VLQSSGLYSLSSVVIVPSSSLGTQTYICNVNHKPSN<br>TKVDKKVEPKSCDGGGSGGGGSEVQLLESGGGL<br>VQPGGSLRLSCAASGFTFSTYAMNWVRQAPGKGL<br>EWVSRIRSKYNNYAIYYADSVKGRFFISRDDSKNT<br>LYLQMNSLRAEDTAVYYCVRHGNFGNSYVSWFA<br>YWGQGTLVTVSSASVAAPSVFIFPPSDEQLKSGTAS<br>VVCLLNNEYPREAKVQWKVDNALQSGNSQESVIE<br>QDSKDSTYSLSSTUFLSKADYEKHKVYACEVIHQG<br>LSSPVTKSFNRGECDKLHTCPPCPAPEAAGGPSVFL<br>FPPKPKDTLMISRTPEVTCVVVDVSHEDPVFKFNW<br>YVDGVEVHNAKTKPREEQYNSTYRVVSVLTVLHQ<br>DWLNGKEYKCKVSNKALGAPIEKT1SKAKGQPREP<br>QVYTLPPCRDELTKNQVSLWCLVKGFYPSDIAVEW<br>ESNGQPENNYKTTPPVLDSDGSFFLYSKLTVDKSR<br>WQQGNVESCSVMHEALHNHYTQKSTSLSPGK |
| 32 | ROR1 HC hole LALA PG | QEQLVESGGRLVTPGGSLTLSCICASGEDFSAYYMS<br>WVRQAPGKGLEWIATIYPSSGKTYYATWVNGRFTI<br>SSDNAQNTVDLQMNSLTAADRATYFCARDSYADD<br>GALFNIWGPGTLVTISSASTKGPSVFPLAPSSKSTSG<br>GTAALGCLVKDYFPEPVTVSWNSGAILTSGVETEPA |

-continued

| SEQ NO: | Name | aa sequence |
|---|---|---|
| | | VLQSSGLYSLSSVVTVPSSSLGTQTYICNVNHKPSN TKVDKKATEPKSCDKTFITCPPCPAPEAAGGPSVELF PPIKPKDILMISRTPEVTCVVVDVSFIEDPEVKFNWY VDGVEVHNAKTKPREEQYNSTYRVVSVLTVLHQD WLNGKEYKCKVSNKALGAPIEKTISKAKGQPREPQ VCTLPPSRDELTKNQVSLSCAVKGFYPSDIAVEWES NGQPENNYKTTPPVLDSDGSFELVSKLTVDKSRWQ QGNVFSCSVMHEALHNHYTQKSLSLSPGK |
| 33 | CD3 VL_CH1 | QAVVTQEPSLTVSPGGTVTLTCGSSTGAVTTSNYA NWVQEKPGQAFRGLIGGTNKRAPGTPARFSGSLLG GKAALTLSGAQPEDEAEYYCALWYSNLWVFGGGT KLTVLSSASTKGPSVFPLAPSSKSTSGGTAALGCLV KDYFPEPVTVSWNSGALTSGVHTFPAVLQSSGLYS LSSVVTVPSSSLGTQTYICNVNFIKPSNTKVDKKVEP KSC |
| 34 | ROR1 x CD3 VH_CL | QEQUVESGGRINTPGGSLTLSCKASGEDFSAYYMS WVRQAPGKGLEWIATIYPSSGKTYYATWVNGRFTI SSDNAQNIVDLQMNSLTAADRATYFCARDSYADD GALFNIWGPGTLVTISSASTKGPSVFPLAPSSKSTSG GTAALGCLVKDYFPEPVTVSWNSGALTSGVHTFPA VLQSSGLYSLSSVVTVPSSSLGTQTYICNVNHKPSN TKVDKKVEPKSCDGGGSGGGGSEVQLLESGGGL VQPGGSLRLSCAASGFTESTYAMNWVRQAPGKGL EWVSRIRSKYNNYATYYADSVKGRFTISRDDSKNI LYLQIVINSLRAEDTAVYYCVRHGNEGNSYVSWFA YWGQGTLVTVSSASVAAPSVFIFPPSDEQLKSGTAS VVCLLNNFYPREAKVQWKVDNALQSGNSQESVTE QDSKDSTYSLSSTLTLSKADYEKHKVYACEVTHQG LSSPVTKSFNRGEC |
| 35 | (RORI)2 x CD3 VH_CL | QEQLVESGGRLVTPGGSLTLSCKASGEDFSAYYMS WVRQAPGKGLEWIATIYPSSGKTYYATWVNGRFTI SSDNAQNTVDLQMNSLTAADRATYECARDSYADD GALFNIWGPGILVTISSASTKGPSVFPLAPSSKSTSG GTAALGCLVKDYFPEPVTVSWNSGALTSGVITHIPA VLQSSGLYSLSSVVTVPSSSLGTQTYICNVNHKPSN TKVDKKVEPKSCDGGGSGGGGSQEQLVESGGRL VTPGGSLTLSCKASGEDFSAYYMSWVRQAPGKGL EWIATTYPSSGKTYYATWVNGRETISSDNAQNTVD LQMNSLTAADRATYFCARDSYADDGALFNIWGPG TLVTISSASTKGPSVFPLAPSSKSTSGGTAALGCLVK DYFPEPVTVSWNSGALTSGVHTFPAVLQSSGLYSL SSVVTVPSSSLGTQTYICNVNHKPSNTKVDKKVEP KSCDGGGSGGGGSEVQLLESGGGLVQPGGSLRLS CAASGFTFSTYAMNWVRQAPGKGIHWVSRIRSKY NNYATYYADSVKGRFTISRDDSKNTLYLQMNSLR AEDTAVYYCVRHGNFGNSYVSWFAYWGQGTLVT VSSASVAAPSVFEEPPSDEQLKSGTASVVCLLNNEY PREAKVQWKVDNALQSGNSQESVTEQDSKDSTYS LSSMILSKADYEKHKVYACEVFHQGLSSPVIKSF NRGEC |
| 36 | FC hole LALA PG | MGWSCIILFLVATATGVHSDKTHTCPPCPAPEAAG GPSVFLEPPKPKDTLMISRTPEVTCVVVDVSHEDPE VKFNWYVDGVEVHNAKTKPREEVYNSTYRVVSV LTVLHQDWLNGKEYKCKVSNKALGAPIEKTISKAK GQPREPQVCTLPPSRDELTKNQVSLSCAVKGEYPS DIAVEWESNGQPENNYKITPPVLDSDGSFELVSKL TVDKSRWQQGNVFSCSVMHEALHNHYTQKSLSLS PGK |
| 37 | ROR1 VH CH1cv x CD3 VL_CH1 Fc knob LALA PG | QEQUVESGGRLVIPGGSLTLSCKASGEDFSAYYMS WVRQAPGKGLEWIATIYPSSGKTYYATWVNGRFTI SSDNAQNTVDLQMNSLTAADRATYFCARDSYADD GALFNIWGPGTLNTISSASTKGPSVFPLAPSSKSTSG GTAALGCLVEDYFPEPVTVSWNSGALTSGVHTFPA VLQSSGLYSLSSVVTVPSSSLGTQTYICNVNHKPSN TKVDEKVEPKSCDGGGSGGGGSQAVVTQEPSLT vSPGGTVTUFCGSSIGAVTISNYANWVQEKPGQA FRGLIGGTNKRAPGTPARFSGSLLGGKAALTLSGA QPEDEAEYYCALWYSNLWVFGGGTKLTVLSSAST KGPSVFPLAPSSKSTSGGTAALGCLVKDYFPEPVTV |

Sequence listing

| SEQ NO: | Name | aa sequence |
|---|---|---|
| | | SWNSGAUYSGVHTFPAVILQSSGLYSLSSVVTVPSSS LGTQTYICNVNHKPSNTKVDKKVEPKSCDKTHTCP PCPAPEAAGGPSVFLFPPKPKDTLMISRIPEVTCVV VDVSHEDPEVKFNWYVDGVEVHNAKTKPREEQY NSTYRVVSVLTVLHQDWLNGKEYKCKVSNKALG APIEKTISKAKGQPREPQVYTLPPCRDELTKNQVSL WCLVKGFYPSDLKVEWESNGQPENNYKFTPPVLDS DGSFELYSKLTVDKSRWQQGNVFSCSVMHEALHN HYTQKSLSLSPGK |
| 38 | ROR1cv HC hole LALA PG | QEQLVESGGRLVTPGGSLTLSCKASGFDFSAYYMS WVRQAPGKGLEWIATIYPSSGKFYYATWVNGRFTI SSDNAQNTVDLQMNSLTAADRATYFCARDSYADD GALFNIWGPGTLVTISSASTKGPSVFPLAPSSKSTSG GTAALGCLVEDYFPEPVTVSWNSGALTSGVHTFPA VLQSSGLYSLSSVVTVPSSSLGTQTYICNNINFIKPSN TKVDEKVEPKSCDKTHTCPPCPAPEAAGGPSVELFP PKPKDILMISKIPEVICVVVDVSHEDPEVKFNWYV DGVEVHNAKTKPREEQYNSTYRVVSVULVLHQDW LNGKEYKCKVSNICKLGAPIEKTISKAKGQPREPQV CTLPPSRDELTKNQVSLSCAVKGFYPSDIAVEWESN GQPENNYKTTPPVLDSDGSFFLVSKLTVDKSRWQQ GNVESCSVMHEALEINHYTQKSUSLSPGK |
| 39 | CD3 VH_CL | EVQLLESGGGLVQPGGSLRLSCAASGFTFSTYAMN WVRQAPGKGLEWVSRIRSKYNNYATYYADSVKG RFTISRDDSKNTLYLQMNSLRAEDTAVYYCVRHG NFGNSYVSWFAYWGQGTINTVSSASVAAPSVFIFP PSDEQLKSGTASVVCLLNNFYPREAKVQWKVDNA LQSGNSQESVTEQDSKDSTYSLSSTLTLSKADYEKH KVYACEVTHQGLSSPVTKSTNRGEC |
| 40 | ROR1cv hum IgG1 LC lambda | ELNLTQSPSVSAALGSPAKITCTLSSAFIKTDTEDWY QQLQGEAPRYLMQVSDGSYTKRPGVPDRFSGSSS GADRYLIIPSVQADDEADYYCGADYIGGYVFGGGI QITVLGQPKAAPSVTLFPPSSIKKILQANKATINCLIS DFYPGAVTVAWKADSSPVKAGVETTTPSKQSNNK YAASSYLSLTPEQWKSFIRSYSCQVTHEGSTVEKTV APTECS |
| 41 | ROR1cv hum IgG1 LC kappa | ELVLTQSPSVSAALGSPAKITCTLSSAHKTDTIDWY QQLQGEAPRYLMQVSDGSYTKRPGVPDRFSGSSS GADRYLIIPSVQADDEADYYCGADYIGGYVFGGGT QLTVTRTVAAPSVFIFPPSDRKLKSGTASVVCLLNN FYPREAKVQWKVIDNALQSGNSQESVTEQDSKDST YSLSSTLTLSKADYEKHKVYACEVTHQGLSSPVTK SFNRGEC |
| 42 | Mab2 ROR1 VH | EVKLVESGGGLVKPGGSLKLSCAASGFTFSSYAMS WVRQIPEKRLEWVASISRGGTTYYPDSVKGRFTISR DNVRNILYLQMSSLRSEDTAMYYCGRYDYDGYYA MDYWGQGTSVTVSS |
| 43 | Mab3 ROR1 VH | QSLEESGGRLVTPGTPLTLTCTVSGIDLNSHWMSW VRQAPGKGLEWIGIIAASGSTYYANWAKGRFTISK TSTTVDLRIASPTTEDTATYFCARDYGDYRLVTFNI WGPGTLVTVSS |
| 44 | Mab4 ROR1 VH | QSVKESEGDLVTPAGNLTLICTASGSDINDYPISWV RQAPGKGLEWIGFINSGGSTWYASWVKGRFTISRE STTVDLKIVITSLYIDDTATYFCARGYSTYYCDFNM GPGTLVTISS |
| 45 | Mab2 ROR1 VL | DIKMTQSPSSMYASLGERVTITCKASPDINSYLSWF QQKPGKSPKLLLIYRANRLDVGVPSRFSGGGSGQDY SLTINSLEYEDMGIYYCLQYDEFPYTFGGGTKLEM K |
| 46 | Mab3 ROR1 VL | ELVMTQTPSSVSAAVGGTVTINCQASQSIGSYLAW YQQKPGQPPKLLIYYASNLASGVPSRFSGSGSGTEY TLTISGVQREDAATYYCLGSLSNSDNVFGGGTELEI L |

-continued

| SEQ NO: | Name | aa sequence |
|---|---|---|
| 47 | Mab4 ROR1 VL | ELVMTQTPSSTSGAVGGTVTINCQASQSIDSNLAW FQQKPGQPPTLIIYRASNLASGVPSRFSGSRSGTEY TLTISGVQREDAATYYCLGGVGNVSYRTSFGGGTE VVVK |
| 48 | Mab2 ROR1 CL | RTVAAPSVFIFPPSDRKLKSGTASVVCLLNNFYPRE AKVQWKVDNALQSGNSQESVTEQDSKDSTYSLSS TLTLSKADYEKHKVYACEVTHQGLSSPVTKSFNRG EC |
| 49 | Mab ROR1 CI | RTVAAPSVFIFPPSDRKLKSGTASVVCLLNNFYPRE AKVQWKVDNALQSGNSQESVTEQDSKDSTYSLSS TLTLSKADYEKHKVYACEVTHQGLSSPVTKSFNRG EC |
| 50 | Mab4 ROR1 CL | RTVAAPSVFIFPPSDRKLKSGTASVVCLLNNFYPRE AKVQWKVDNALQSGNSQESVTEQDSKDSTYSLSS TLTLSKADYEKHKVYACEVTHQGLSSPVTKSFNRG EC |
| 51 | Mab2 ROR1 CH1 | ASTKGPSVFPLAPSSKSTSGGIAALGCLVEDYTPEP VIVSWNSGALTSGVETFPAVLQSSGUYSLSSVVIV PSSSLGTQTYICNVNHKPSNTKVDEKVEPKSC |
| 52 | Mab3 ROR1 CH1 | ASTKGPSVFPLAPSSKSTSGGTAALGCLVEDYFPEP VTVSWNSGALTSGVHTFPAVLQSSGLYSLSSVVTV PSSSLGTQTYICNVNHKPSNTKVDEKVEPKSC |
| 53 | Mab4 ROR1 CH1 | ASTKGPSVFPLAPSSKSTSGGTAALGCLVEDYFPEP VTVSWNSGALTSGVHTFPAVLQSSGLYSLSSVVTV PSSSLGTQTYICNVNIIKPSNIKVDEKVEPKSC |
| 54 | Mab2 knob HC | EVKLVESGGGLVKPGGSLKLSCAASGETFSSYAMS WVRQIPEKRLEWVASISRGGRTYYPDSVKGRFTISR DNVRNILYLQMSSLRSEDIAMYYCGRYDYDGYYA MDYWGQGTSVTVSSASTKGPSVFPLAPSSKSTSGG TAALGCLVEDYFPEPVTVSWNSGALTSGVITITFPAV LQSSCANSSSVVTVPSSSLGTQTYICNVNHKPSNT KVDEKVEPKSCDGGGGSGGGGSQAVVTQEPSLTV SPGGTVTLTCGSSTGAVTTSNYANWVQEKPGQAF RGLIGGTNKRAPGTPARFSGSLLGGKAALTLSGAQ PEDEAEYYCALWYSNLWVFGGGTKLTVLSSASTK GPSVFPLAPSSKSTSGGTAALGCLVKDYFPEPVTVS WNSGALTSGVHTFPAVLQSSGLYSLSSVVTVPSSSL GIQTYICNVNHKPSNTKVDKKVEPKSCDKTHTCPP CPAPEAAGGPSVFLFPPKPKDTLMISRTPEVTCVVV DVSHEDPEVKFNWYVDGVEVHNAKTKPREEQYNS TYRVVSVLTVLFIQDWLNGKEYKCKVSNKALGAPI EKTISKAKGQPREPQYYTLPPCRDELTKNQVSLWC LVKGFYPSDIAVENVESNGQPENNYKTTPPVLDSDG SFFLYSKLTVDKSRWQQGNVFSCSVMHEALHNHY FQKSLSLSPGK |
| 55 | Mab2 hole HC | EVKLVESGGGLVKPGGSLKLSCAASGFTFSSYAMS VVVRQIPEKRLEWVASISRGGTTYYPDSVKGRFTISR DNVRNILYILQMSSLRSEDIANTYYCGRYDYDGYYA MDYWGQGTSVTVSSASTKGPSVFPLAPSSKSTSGG TAALGCLVEDYFPEPVTVSWNSGALTSGVHTFPAV LQSSGLYSLSSVVTVPSSSLGTQTYICNVNHKPSNT KVDEKVEPRSCDKTFITCPPCPAPEAAGGPSVFLFPP KPRDTLMISRTPEVTCVVVDVSHEDPEVKFNAVYV DGVEVHNAKTKPREEQYNSTYRVVSVLTVLHQDW LNGKEYKCKVSNKALGAPIEKTISICKKGQPREPQV CILPPSRDELTKNQVSLSCAVKGFYPSDIAVENVESN GQPENNYKTIPPVLDSOGSFFLVSKLTVDKSRWOO GNVFSCSVMHEALHNIIYTOKSLSLSPGK |
| 56 | Mab2 ROR1 LC | DIKMTQSPSSMYASLGERVTITCKASPDINSYLSWF QQKPGKSPKTLIYRANRLVDGVPSRFSGGGSGODY SLTINSLEYEDNIGIYYCLQYDEFPYTFGGGTKLEM KRTVAAPSVFIFPPSDRKLKSGTASVVCLLNNFYPR |

-continued

Sequence listing

| SEQ NO: | Name | aa sequence |
|---|---|---|
|  |  | EAKVQWKVQNALQSGNSQESVTEQDSKDSTYSLS STLTLSKADYEKHKVYACEVTHQGLSSPVTKSFNR GEC |
| 57 | Mab3 ROR1 knob HC | QSLEESGGRLVTPGTPLTLTCTVSGIDLNSHWMSW VRQAPGKGLEWIGIIAASGSTYYANWAKGRFTISK TSTTVDLRIASPTTEDTATYFCARDYGDYRLVITNI WGPGTLVTVSSASTKGPSVFPLAPSSKSTSGGTAAL GCIVEDYFPEPVTVSWNSGALTSGVHTFPAVLQSS GLYSLSSVVTVPSSSLGTQTYICNVNHKPSNTKVDE KVEPKSCDGGGSGGGGSQAVVTQEPSLTVSPGGT VTUFCGSSTGAVTTSNYANWVQEKPGQAFRGLIGG TNKRAPGTPARFSGSLLGGKAALTLSGAQPEDEAE YYCALWYSNLWVFGGGTKLFVLSSASTKGPSVFPL APSSKSTSGGTAALGCLVKDYFPEPATINSWNSGAL TSGVHTFPAVLQSSGLYSLSSVVTVPSSSLGTQTYIC NVNIIKPSNTKVDKKVEPKSCDRIFITCPPCPAPEAA GGPSVFLFPPKPKDTLMISRTPEVTCVVVDVSHEDP EVKINWYVQGVEVEINAKTKPREEQYNSTYRANS VLTVLHQDWLNGKEYKCKVSNKALGAPTEKTTSKA KGQPREPQVYTLPPCRDELTKNQVSLWCLVKGFYP SDIAVEWESNGQPENNYKTTPPVLDSDGSFFLYSKL TVDKSRWQQGNVESCSVMHEALFINHYTQKSLSLS PGK |
| 58 | Mab3 ROR1 hole HC | QSLEESGGRLVTPGTPLTLTCTVSGIDLNSHWMSW-VRQAPGKGLEWIGHAASGSTYYANWAKGRFTISK TSTTVDLRIASPTTEDTATYFCARDYGDYRLVTFNI WGPGTINTVSSASTKGPSVFPLAPSSKSTSGGTAAL GCLVEDYFPEPVTVSWNSGALTSGVHTFPAVLQSS GLYSISSVVIVPSSSLGIQTYICNVNHKPSNTKVDE KVEPKSCDKFHTCPPCPAPEAAGGPSVFLFPPKPKD LMISRTPEVTCVVVDVSHEDPEVKFNWYVDGVE VHNAKTKPREEQYNSTYRVVSVLTVLHQDWLNGK EYKCKVSNKALGAPIIEKTISKAKGQPREPQVCTLPP SRDELTKNQVSLSCAVKGFYPSDIAVEWESNGQPE NNYKTrPPVLDSDGSFFLVSKLTVDKSRWQQGNVF SCSVMHEALHNHYTQKSLSLSPGK |
| 59 | Mab3 ROR1 LC | ELVMTQTPSSVSAAVGGTVTINCQASQSIGSYLAW YQQKPGQPPKLLIYYASNLASGVPSRFSGSGSGTEY TLTISGVQREDAATYYCLGSLSNSDNVFGGGTELEI LRTVAAPSVFIFPPSDRKLKSGTASVVCLLNNFYPR EAKVQWKVDNALQSGNSQESVTEQDSKDSTYSLS STLTLSKADYEKHKVYACEVTHQGLSSPVIKSFNR GEC |
| 60 | Mab4 RORI knob HC | QSVKESEGDLVTPAGNLTLTCTASGSDINDYPISIATV RQAPGKGLEWIGFINSGGSTWYASWVKGRFFISRT STIVDLKMTSILTIDDTATYFCARGYSTYYCDFNIW GPGTLVTISSASTKGPSVFPLAPSSKSTSGGTAALGC LVEDYFPEPVTVSWNSGALTSGVHTFPAVLQSSGL YSLSSVVTVPSSSLGTQTYICNVNHKRSNTKVDEKV EPKSCDGGGSGGGGSQAVVTQEPSLTVSPGGTVT LTCGSSTGAVTfSNYANWVQEKPGQAFRGLIGGIN KRAPGTPARFSGSLLGGICAALTLSGAQPEDEAEYY CALWYSNILWVFGGGTKLTVLSSASTKGPSVFPLAP SSKSTSGGTAALGCLNKDYFPEPVTVSWNSGALTS GVHTFPAVLQSSGLYSLSSVVTVPSSSLGTQTYICN VNHKPSNTKVDKKVEPKSCDKTHTCPPCPAPEAAG GPSVFLFPPKPKDTLMISRTPEVTCVVVDVSHEDPE VKFNWYVDGVEVHNAKTKPREEQYNSTYRVVSV LTVLFIQDWLNGKEYKCKVSNKALGAPIEKTISKAK GQPREPQVYTLPPCRDELTKNQVSLWCLVKGFYPS DIAVEWESNGQPENNYKTIPPVLDSDGSFFLYSKL TVDKSRWQQGNVFSCSVMHEAILHNHYTQKSILSLS PGK |
| 61 | Mab4 RORI hole HC | QSVKESEGDLVTPAGNLTLTCTASGSDINDYPISWV RQAPGKGLEWIGFINSGGSTWYASWVKGRFTISRT STIVDLKATISLTIDDITIYFCARGYSTYYCDFNIW-GPOTLVFISSNSTKCIPSVFPLAPSSKSTSGGTAALGC LVEDYFPEPVTVSWNSGALTSGVHTFPAVLQSSGL YSLSSVVTVPSSSLGTQTYICNVNHKPSNTKVDEKV |

-continued

Sequence listing

| SEQ NO: | Name | aa sequence |
|---|---|---|
| | | EPKSCDKIETCPPCPAPEAAGGPSVFLFPPKPKDTL MISRTPEVTCVVVDVSHEDPEVKFINWYVDGVEVH NAKTKPREEWNSTYRVVSVLTVILHQDWLNGKEY KCKVSNICUGAPIEKTISKAKGQPREPQVCILPPSR DELIKNQVSLSCAVKGFYPSDIAVEWESNGQPENN YKTTPPVLDSDGSFFLVSKLTVDKSRWQQGNVFSC SVMHEALFINHYTQKSLSLSPGK |
| 62 | Mab4 ROR1 LC | ELVMTQFPSSTSGAVGGIVIENCQSQSIDSNILAW FIMPGQPPTLUYIZASNLASGVPSRFSGSRSGTEY TLTLSGVQREDAATYYCLGGVGNVSYRTSFGGGTE VVVKRTVAARSVFIFPRSDRKLKSGTASVVCLINNF YPREAKVQWKVDNALQSGNSQESVTEQPSKDSTY SLSSTLTSKADYEKHKVYACEVTHQGILSSPVTKS FNRGEC |

To make the following Fc-containing anti-ROR1/anti-CD3 TCBs according to the invention, the respective constructs/sequence IDs as mentioned in the table above are needed:

ROR1-TCB (2+1): 37, 38, 39, 40 x2 or 37, 38, 39, 41 x2
ROR1-TCB (1+1): 36, 37, 39, 40 or 36, 37, 39, 41
Mab2 ROR1-TCB (2+1): 39, 54, 55, 56 x2
Mab3 ROR1-TCB (2+1): 39, 57, 58, 59 x2
Mab4 ROR1-TCB (2+1): 39, 60, 61, 62 x2

In the following specific embodiments of the invention are listed:

1. A bispecific bi- or trivalent antibody specifically binding to the two targets which are human CD3ε (further named also as "CD3") and the extracellular domain of human ROR1 (further named also as "ROR1"), wherein the variable domains VL and VH in a light chain and the respective heavy chain are replaced by each other, characterized in comprising a constant domain CL wherein the amino acid at position 124 is substituted independently by lysine (K), arginine (R) or histidine (H) (numbering according to Kabat), and in the respective constant domain CH1 the amino acid at position 147 and the amino acid at position 213 is substituted independently by glutamic acid (E), or aspartic acid (D) (numbering according to EU index of Kabat).

2. The bispecific antibody specifically binding to the two targets which are human CD3ε and the extracellular domain of human ROR1, characterized in comprising
   a) the first light chain and the first heavy chain of a first antibody which specifically binds to ROR1; and
   b) the second light chain and the second heavy chain of a second antibody which specifically binds to CD3, and wherein the variable domains VL and VH in the second light chain and second heavy chain of the second antibody are replaced by each other; and wherein
   c) in the constant domain CL of the first light chain under a) the amino acid at position 124 is substituted independently by lysine (K), arginine (R) or histidine (H) (numbering according to Kabat), and wherein in the constant domain CH1 of the first heavy chain under a) the amino acid at position 147 and the amino acid at position 213 is substituted independently by glutamic acid (E), or aspartic acid (D) (numbering according to EU index of Kabat).

3. The bispecific antibody specifically binding to the two targets which are human CD3ε and the extracellular domain of human ROR1, characterized in comprising
   a) the first light chain and the first heavy chain of a first antibody which specifically binds to ROR1; and
   b) the second light chain and the second heavy chain of a second antibody which specifically binds to CD3, and wherein the variable domains VL and VH in the second light chain and second heavy chain of the second antibody are replaced by each other; and wherein
   c) in the constant domain CL of the second light chain under b) the amino acid at position 124 is substituted independently by lysine (K), arginine (R) or histidine (H) (numbering according to Kabat), and wherein in the constant domain CH1 of the second heavy chain under b) the amino acid at positions 147 and the amino acid at position 213 is substituted independently by glutamic acid (E), or aspartic acid (D) (numbering according to EU index of Kabat).

4. The bispecific antibody according to embodiment 2, characterized in that said bispecific antibody comprises in addition a Fab fragment of said first antibody (further named also as "ROR1-Fab") and in the constant domain CL said ROR1-Fab the amino acid at position 124 is substituted independently by lysine (K), arginine (R) or histidine (H) (numbering according to Kabat), and wherein in the constant domain CH1 of said ROR1-Fab the amino acid at positions 147 and the amino acid at position 213 is substituted independently by glutamic acid (E), or aspartic acid (D) (numbering according to EU index of Kabat).

5. The bispecific antibody according to embodiment 3, characterized in that said bispecific antibody comprises in addition a second Fab fragment of said first antibody ("ROR1-Fab").

6. The bispecific antibody according to any one of embodiment 1, characterized in consisting of one Fab fragment of an antibody specifically binding to CD3 ε (further named also as "CD3-Fab"), and one Fab fragment of an antibody specifically binding to ROR1 (further named also as "ROR1-Fab(s)") and a Fc part, wherein the CD3-Fab and the ROR1-Fab are linked via their C-termini to the hinge region of said Fc part and wherein either the CD3-Fab or the ROR1-Fab comprises aa substitution and the CD3-Fab comprises crossover.

Figure 1C:
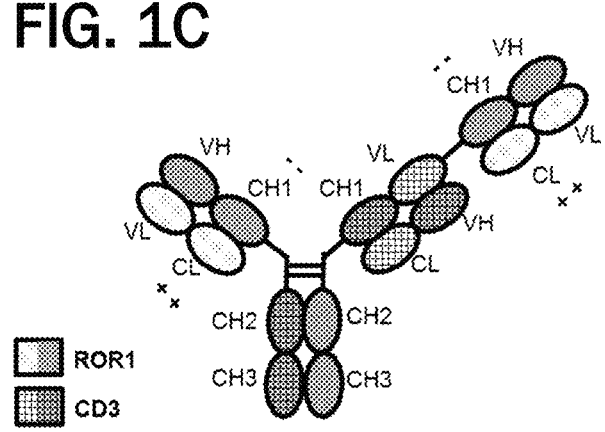
Figure 1D:
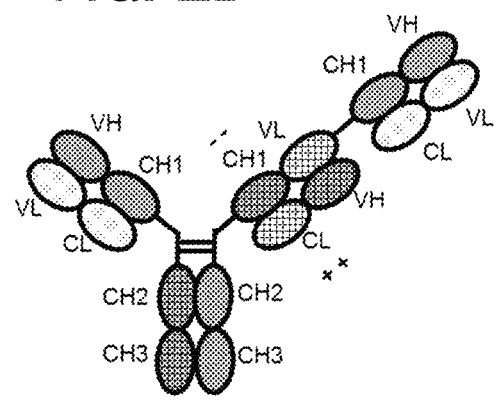
Figure 1E:
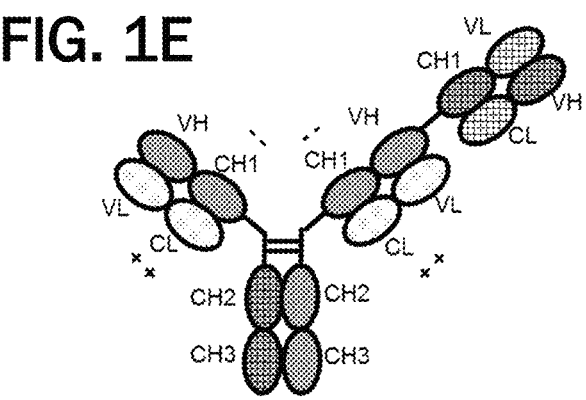

7. The bispecific antibody according to embodiment 6, characterized in consisting of one CD3-Fab, and one ROR1-Fab and a Fc part, wherein the CD3-Fab and the ROR1-Fab are linked via their C-termini to the hinge region of said Fc part and a second ROR1-Fab, which is linked with its C-terminus to the N-terminus of the CD3-Fab and wherein the CD3-Fab comprises crossover and either the CD3-Fab or both ROR1-Fabs comprise aa substitution (FIGS. 1C and 1D).

8. The bispecific antibody according to embodiment 7, characterized in consisting of ROR1-Fab-Fc-CD3-Fab-ROR1-Fab, wherein both ROR1-Fabs comprise aa substitution and the CD3-Fab comprises VL/VH crossover.

Figure 1F:
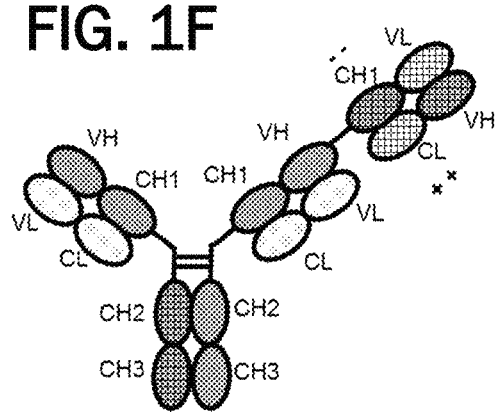
Figure 1G:
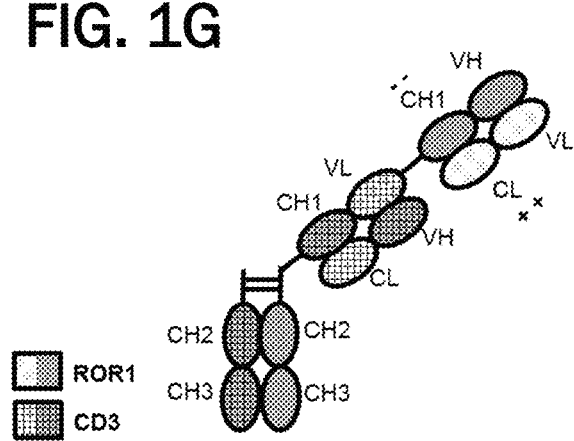

9. The bispecific antibody according to embodiment 1, characterized in consisting of two ROR1-Fabs and a Fc part, wherein the ROR1-Fabs are linked via their C-termini to the hinge region of said Fc part and a CD3-Fab, which is linked with its C-terminus to the N-terminus of one ROR1-Fab and the CD3-Fab comprises crossover and either the CD3-Fab or both ROR1-Fabs comprise aa substitution (FIGS. 1F and 1G).

Figure 1H:
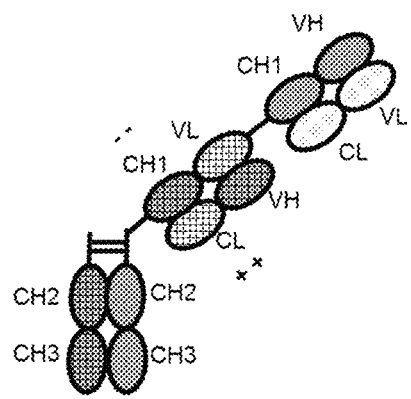
Figure 1I:
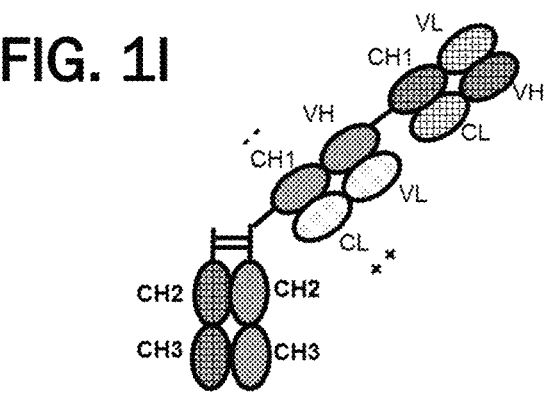

10. The bispecific antibody according to any one of embodiments 1 to 5, characterized in consisting of one CD3-Fab, which is linked via its C-terminus to the hinge region of said Fc part and a ROR1-Fab, which is linked with its C-terminus to the N-terminus of the CD3-Fab and either the CD3-Fab or the ROR1-Fab comprise aa substitution (FIGS. 1H and 1I).

Figure 1J:
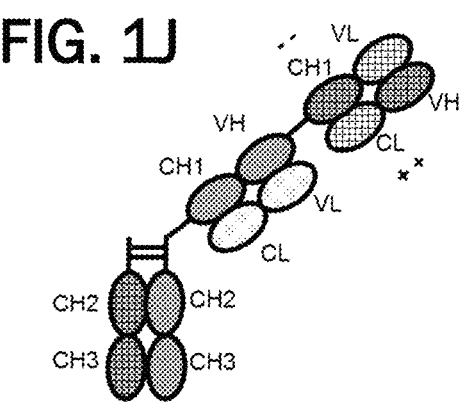

11. The bispecific antibody according to any one of embodiments 1 to 6, characterized in consisting of one ROR1-Fab, which is linked via its C-terminus to the hinge region of said Fc part and a CD3-Fab, which is linked with its C-terminus to the N-terminus of the ROR1-Fab and either the CD3-Fab or the ROR1-Fab comprise aa substitution (FIGS. 1J and 1K).

12. The bispecific antibody according to any one of embodiments 1 to 11, characterized in comprising the CDR sequences of anti-ROR1 antibody MAB1.

13. The bispecific antibody according to any one of embodiments 1 to 12, characterized in comprising the VH and VL sequences of anti-ROR1 antibody MAB1, or an antibody comprising the VH, VL, CH1, and CL sequences of anti-ROR1 antibody MAB1.

14. The bispecific antibody according to any one of embodiments 1 to 13, characterized in that the antibody portion specifically binding to human CD3ε, preferably the Fab fragment, is characterized in comprising
  a) a variable domain VH comprising the heavy chain CDRs of SEQ ID NO: 12, 13 and 14 as respectively heavy chain CDR1, CDR2 and CDR3 and a variable domain VL comprising the light chain CDRs of SEQ ID NO: 15, 16 and 17 as respectively light chain CDR1, CDR2 and CDR3 of the anti CD3ε antibody (CDR MAB CD3 H2C), or
  b) a variable domain VH comprising the heavy chain CDRs of SEQ ID NO: 23, 24 and 25 as respectively heavy chain CDR1, CDR2 and CDR3 and a variable domain VL comprising the light chain CDRs of SEQ ID NO: 26, 27 and 28 as respectively light chain CDR1, CDR2 and CDR3 of the anti CD3ε antibody (CDR MAB CD3 CH2527).

15. The bispecific antibody according to any one of embodiments 1 to 14, characterized in that the antibody portion specifically binding to human CD3ε is characterized in that the variable domains are of
  a) SEQ ID NO:10 and 11 (VHVL MAB CD3 H2C), or
  b) SEQ ID NO:21 and 22 (VHVL MAB CD3 CH2527).

16. The bispecific antibody according to any one of embodiments 1 to 15, characterized in that the Fab fragment, specifically binding to human ROR1 is characterized in comprising a variable domain VH comprising the heavy chain CDRs CDR1H of SEQ ID NO:7, a CDR2H of SEQ ID NO:8, a CDR3H of SEQ ID NO: 9 and comprising a variable domain VL comprising the light chain CDRs CDR1L of SEQ ID NO:3, a CDR2L of SEQ ID NO:4, a CDR3L of SEQ ID NO: 5 (CDR MAB1).

17. The bispecific antibody according to any one of embodiments 1 to 16, characterized in that the Fab fragment, specifically binding to human ROR1 is characterized in comprising a VH of SEQ ID NO: 10 and a VL of SEQ ID NO: 11 (VHVL MAB1).

18. The bispecific antibody according to any one of embodiments 1 to 17, characterized in that in addition to the amino acid replacement at position 124 in the constant domain CL the amino acid at position 123 is substituted independently by lysine (K), arginine (R) or histidine (H).

19. The bispecific antibody according to any one of embodiments 1 to 18, characterized in that amino acid 124 is K, amino acid 147 is E, amino acid 213 is E, and amino acid 123 is R or amino acid 124 is K, amino acid 147 is E, amino acid 213 is K, and amino acid 123 is K Preferably amino acid 123 is R for a kappa light chain and K for a lambda light chain.

20. A bispecific antibody specifically binding to the extracellular domain of human ROR1 and to human CD3ε, characterized in comprising a heavy and light chain set selected from the group consisting of polypeptides SEQ ID NO:37, SEQ ID NO:38, SEQ ID NO:39, and SEQ ID NO:40 or from the group consisting of polypeptides SEQ ID NO:37, SEQ ID NO:38, SEQ ID NO:39, and SEQ ID NO:41.

21. The antibody according to embodiment 20, characterized in that in the antibody portion specifically binding to human CD3ε
  a) the variable domain VH is replaced by a variable domain VH comprising the heavy chain CDRs of SEQ ID NO: 12, 13 and 14 as respectively heavy chain CDR1, CDR2 and CDR3 and the variable domain VL is replaced by a variable domain VL comprising the light chain CDRs of SEQ ID NO: 15, 16 and 17 as respectively light chain CDR1, CDR2 and CDR3 of the anti CD3ε antibody, or
  b) the variable domain VH is replaced by a variable domain VH comprising the heavy chain CDRs of SEQ ID NO: 23, 24 and 25 as respectively heavy chain CDR1, CDR2 and CDR3 and the variable domain VL is replaced by a variable domain VL comprising the light chain CDRs of SEQ ID NO: 26, 27 and 28 as respectively light chain CDR1, CDR2 and CDR3 of the anti CD3ε antibody.

22. The antibody according to any one of embodiments 1 to 21, characterized in that the CH3 domain of one heavy chain and the CH3 domain of the other heavy chain each meet at an interface which comprises an original interface between the antibody CH3 domains; wherein said interface is altered to promote the formation of the bispecific antibody, wherein the alteration is characterized in that:
  a) the CH3 domain of one heavy chain is altered, so that within the original interface the CH3 domain of one heavy chain that meets the original interface of the CH3 domain of the other heavy chain within the bispecific antibody, an amino acid residue is replaced with an amino acid residue having a larger side chain volume, thereby generating a protuberance within the interface of the CH3 domain of one heavy chain which is positionable in a cavity within the interface of the CH3 domain of the other heavy chain and
  b) the CH3 domain of the other heavy chain is altered, so that within the original interface of the second CH3 domain that meets the original interface of the first CH3 domain within the bispecific antibody an amino acid residue is replaced with an amino acid residue having a smaller side chain volume, thereby generating a cavity within the interface of the second CH3 domain within which a protuberance within the interface of the first CH3 domain is positionable.

23. The antibody according to any one of embodiments 1 to 22, characterized in comprising in the human IgG1 Fc part amino acid substitution of Pro329 with glycine or arginine and/or substitutions L234A and L235A.

24. The antibody according to embodiment 23, characterized in being of construct ROR1 Fab-Fc-CD3 Fab-ROR1 Fab and comprising VL/VH crossover within the Fab fragment of the anti-CD3ε antibody and in comprising in the human IgG1 Fc part amino acid substitutions of Pro329 with glycine, Leu234 with alanine and Leu235 with alanine.

25. The antibody according to any one of embodiments 1 to 22, characterized in
   a) being of construct ROR1 Fab-Fc-CD3 Fab-ROR1 Fab,
   b) comprising VL/VH crossover within the Fab fragment of the anti-CD3 antibody,
   c) comprising a human IgG1Fc part,
   d) comprising within the Fc part substitution of Pro329 with glycine and substitutions of Leu234 by alanine and Leu235 by alanine, and
   e) that in the constant domain CL of both ROR1 Fabs the amino acid at position 124 is substituted by lysine (K) and at position 123 by arginine (R) for a kappa light and lysine (K) for a lambda light chain, in the constant domain CH1 the amino acid at position 147 and the amino acid at position 213 are substituted by glutamic acid (E).

26. The antibody according to any one of embodiments 1 to 25, characterized in specifically binding to the two targets human CD3ε and the extracellular domain of human ROR1, characterized in not internalizing in a concentration of 1 nM in primary B-CLL cells at 37° C. during two hours.

27. The antibody according to any one of embodiments 1 to 26, characterized in specifically binding to the two targets human CD3ε and the extracellular domain of human ROR1, characterized in that the bispecific antibody does not internalize in a cell based assay at 37° C. during 2 hrs, using ROR1-positive primary B-CLL cells and used at an antibody concentration of 1 nM, whereby not internalize means, that the mean fluorescence intensity (MFI), as detected by flow cytometry, of said bispecific antibody upon binding to ROR1-positive primary B-CLL cells measured at time 0 is not reduced more than 50%, preferably not more than 30% when re-measured after a 2 hr-incubation at 37° C.

28. The antibody according to embodiments 1 to 27, characterized by an elimination half-life in mice, preferably cynomolgus monkeys of longer than 12 hours, preferably 3 days or longer.

29. The antibody according to embodiments 1 to 28, characterized in showing an EC50 value for binding to ROR1-positive cell lines (e.g. RPMI8226 cells, Rec-1 cells, Jeko cells) of 30 nM or lower, preferably an EC50 value of 15 nM and lower.

30. The antibody according to embodiments 1 to 29, characterized by its capability to induce redirected killing of ROR1 expressing tumor cells (e.g. RPMI8226 cells, Rec-1 cells, Jeko cells, ovarian cancer cell lines like PA-1, COLO-704, OVCAR-5, SK-OV-3)) in the presence of human T cells with an EC50 lower than 10 nM, preferably 1 nM, preferably 0.05 nM, preferably 0.02 nM, preferably 0.002 nM and lower.

31. The antibody according to embodiments 1 to 30, characterized in that said antibody stored in standard formulation buffer at 37° C. preferably at 40° C., for 10 days, preferably up to 2 weeks, preferably up to 4 weeks, does not result in more than 10% changes (Δ), preferably not more than 5% changes (Δ), in high molecular weight (HMW) species and/or low molecular weight (LMW) species and/or monomer content as compared to the said antibody stored in the same formulation buffer at −80° C. for the same period of storage.

32. A method for the preparation of an a bispecific antibody according to any one of embodiments 1 to 31 comprising the steps of
   a) transforming a host cell with vectors comprising nucleic acid molecules encoding the light chain and heavy chain of an antibody according to any one of embodiments 1 to 31,
   b) culturing the host cell under conditions that allow synthesis of said antibody molecule; and
   c) recovering said antibody molecule from said culture.

33. A host cell comprising vectors comprising nucleic acid molecules encoding the light chain and heavy chains of an antibody according to any one of embodiments 1 to 31.

34. A pharmaceutical composition comprising an antibody according to any one of embodiments 1 to 30 and a pharmaceutically acceptable excipient.

35. The antibody according to any one of embodiments 1 to 31 or the pharmaceutical composition of embodiment 34 for use as a medicament.

36. An antibody according to any one of embodiments 1 to 31 or the pharmaceutical composition of embodiment 34 for use as a medicament in the treatment of ROR1-positive hematological malignancies comprising chronic lymphocytic leukemia (CLL), hairy cell leukemia (HCL), acute lymphoblastic leukemia (ALL), acute myeloid leukemia (AML), chronic myeloid leukemia (CML), mantle cell lymphoma (MCL), marginal zone lymphoma (MZL), diffuse large B cell lymphoma (DLBCL), multiple myeloma (MM), follicular lymphoma (FL), and for the treatment of ROR1-positive solid tumors such as ovarian cancer, breast cancer and lung cancer.

37. An antibody according to any one of embodiments 1 to 31 or the pharmaceutical composition of embodiment 34 for use as a medicament in the treatment of multiple myeloma.

38. An antibody according to any one of embodiments 1 to 31 or the pharmaceutical composition of embodiment 34 for the treatment of of chronic lymphocytic leukemia (CLL) of B-cell lineage (B-CLL) and for use as a medicament in the treatment of plasma cell disorders like Multiple Myeloma MM or other B-cell disorders expressing ROR1.

39. The antibody according to any one of claims 1 to 31 or the pharmaceutical composition of claim 34 for use as a medicament in the treatment of a disease selected from the group consisting of ovarian cancer, lung cancer, breast cancer, gastric cancer, and pancreatic cancer.

40. The antibody according to any one of claims 1 to 31 or the pharmaceutical composition of claim 34 for use as a medicament in the treatment of ovarian cancer.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, MD (1991). Amino acids of antibody chains are numbered and referred to according to EU numbering (Edelman, G. M., et al., Proc. Natl. Acad. Sci.

USA 63 (1969) 78-85; Kabat, E. A., et al., Sequences of Proteins of Immunological Interest, 5th ed., Public Health Service, National Institutes of Health, Bethesda, MD, (1991)).

Recombinant DNA Techniques

Standard methods were used to manipulate DNA as described in Sambrook, J. et al., Molecular cloning: A laboratory manual; Cold Spring Harbor Laboratory Press, Cold Spring Harbor, New York, 1989. The molecular biological reagents were used according to the manufacturer's instructions. General information regarding the nucleotide sequences of human immunoglobulins light and heavy chains is given in: Kabat, E. A. et al., (1991) Sequences of Proteins of Immunological Interest, 5th ed., NIH Publication No. 91-3242. Amino acids of antibody chains were numbered and referred to according to Kabat, E. A., et al., Sequences of Proteins of Immunological Interest, 5th ed., Public Health Service, National Institutes of Health, Bethesda, MD, (1991).

Gene Synthesis a) Desired gene segments were prepared from oligonucleotides made by chemical synthesis. The 600-1800 bp long gene segments, which were flanked by singular restriction endonuclease cleavage sites, were assembled by annealing and ligation of oligonucleotides including PCR amplification and subsequently cloned via the indicated restriction sites e.g. Kpn1/Sad or Asc1/Pac1 into a pPCRScript (STRATAGENE) based pGA4 cloning vector. The DNA sequences of the subcloned gene fragments were confirmed by DNA sequencing. Gene synthesis fragments were ordered according to given specifications at GENEART (Regensburg, Germany). b) Desired gene segments where required were either generated by PCR using appropriate templates or were synthesized by GENEART AG (Regensburg, Germany) from synthetic oligonucleotides and PCR products by automated gene synthesis. The gene segments flanked by singular restriction endonuclease cleavage sites were cloned into standard expression vectors or into sequencing vectors for further analysis. The plasmid DNA was purified from transformed bacteria using commercially available plasmid purification kits. Plasmid concentration was determined by UV spectroscopy. The DNA sequence of the subcloned gene fragments was confirmed by DNA sequencing. Gene segments were designed with suitable restriction sites to allow sub-cloning into the respective expression vectors. If required, protein coding genes were designed with a 5'-end DNA sequence coding for a leader peptide which targets proteins for secretion in eukaryotic cells.

DNA Sequence Determination

DNA sequences are determined by double strand sequencing.

DNA and Protein Sequence Analysis and Sequence Data Management

The CLONE MANAGER (Scientific & Educational Software) software package version 9.2 was used for sequence mapping, analysis, annotation and illustration.

Expression Vectors a) The fusion genes comprising the described antibody chains as described below were generated by PCR and/or gene synthesis and assembled with known recombinant methods and techniques by connection of the according nucleic acid segments e.g. using unique restriction sites in the respective vectors. The subcloned nucleic acid sequences were verified by DNA sequencing. For transient transfections larger quantities of the plasmids are prepared by plasmid preparation from transformed E. coli cultures (NUCLEOBOND AX, MACHEREY-NAGEL).

b) For the generation of anti-ROR1 antibody expression vectors, the variable regions of heavy and light chain DNA sequences were subcloned in frame with either the human IgG1 constant heavy chain or the hum IgG1 constant light chain pre-inserted into the respective generic recipient expression vector optimized for expression in mammalian cell lines. The antibody expression is driven by a chimeric MPSV promoter comprising a CMV enhancer and a MPSV promoter followed by a 5' UTR, an intron and a Ig kappa MAR element. The transcription is terminated by a synthetic polyA signal sequence at the 3' end of the CDS. All vectors carry a 5'-end DNA sequence coding for a leader peptide which targets proteins for secretion in eukaryotic cells. In addition each vector contains an EBV OriP sequence for episomal plasmid replication in EBV EBNA expressing cells.

c) For the generation of ROR1×CD3 bispecific antibody vectors, the IgG1 derived bispecific molecules consist at least of two antigen binding moieties capable of binding specifically to two distinct antigenic determinants CD3 and ROR1. The antigen binding moieties are Fab fragments composed of a heavy and a light chain, each comprising a variable and a constant region. At least one of the Fab fragments was a "Crossfab" fragment, wherein VH and VL were exchanged. The exchange of VH and VL within the Fab fragment assures that Fab fragments of different specificity do not have identical domain arrangements. The bispecific molecule design was monovalent for CD3 and bivalent for ROR1 where one Fab fragment was fused to the N-terminus of the inner CrossFab (2+1). The bispecific molecule contained an Fc part in order for the molecule to have a long half-life. A schematic representation of the constructs is given in FIG. 1; the preferred sequences of the constructs are shown in SEQ ID NOs 39 to 52. The molecules were produced by polymer-based co-transfecting HEK293 EBNA cells growing in suspension with the mammalian expression vectors. For preparation of 2+1 CrossFab-IgG constructs, cells were transfected with the corresponding expression vectors in a 1:2:1:1 ratio ("vector Fc (knob)":"vector light chain":"vector light chain CrossFab":"vector heavy chain-CrossFab").

Cell Culture Techniques

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Expression in HEK293 Cells (HEK293-EBNA System)

Bispecific antibodies were expressed by transient co-transfection of the respective mammalian expression vectors in HEK293-EBNA cells, which were cultivated in suspension, using a polymer. One day prior to transfection the HEK293-EBNA cells were seeded at 1.5 Mio viable cells/mL in EX-CELL medium, supplemented with 6 mM of L-Glutamine. For every mL of final production volume 2.0 Mio viable cells were centrifuged (5 minutes at 210×g). The supernatant was aspirated and the cells resuspended in 100 µL of CD CHO medium. The DNA for every mL of final production volume was prepared by mixing 1 µg of DNA (Ratio heavy chain:modified heavy chain:light chain:modified light chain=1:1:2:1) in 100 µL of CD CHO medium. After addition of 0.27 µL of polymer solution (1 mg/mL) the mixture was vortexed for 15 seconds and left at room temperature for 10 minutes. After 10 minutes, the resuspended cells and DNA/polymer mixture were put together and then transferred into an appropriate container which was placed in a shaking device (37° C., 5% CO2). After a 3 hours incubation time 800 µL of EX-CELL Medium, supplemented with 6 mM L-Glutamine, 1.25 mM valproic acid and 12.5% Pepsoy (50 g/L), was added for every mL of final Production volume. After 24 hours, 70 µL of Feed solution was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used. The recombinant anti-BCMA human antibody and bispecific antibodies were produced in suspension by polymer-based co-transfecting HEK293-EBNA cells with the mammalian expression vectors. The cells were transfected with two or four vectors, depending in the format. For the human IgG1 one plasmid encoded the heavy chain and the other plasmid the light chain. For the bispecific antibodies four plasmids were co-transfected. Two of them encoded the two different heavy chains and the other two encoded the two different light chains. One day prior to transfection the HEK293-EBNA cells were seeded at 1.5 Mio viable cells/mL in F17 Medium, supplemented with 6 mM of L-Glutamine.

Protein Determination

Determination of the antibody concentration was done by measurement of the absorbance at 280 nm, using the theoretical value of the absorbance of a 0.1% solution of the antibody. This value was based on the amino acid sequence and calculated by GPMAW software (Lighthouse data).

SDS-PAGE

The NUPAGE Pre-Cast gel system (INVITROGEN) is used according to the manufacturer's instruction. In particular, 10% or 4-12% NUPAGE NOVEX® Bis-TRIS Pre-Cast gels (pH 6.4) and a NUPAGE MES (reduced gels, with NUPAGE Antioxidant running buffer additive) or MOPS (non-reduced gels) running buffer is used.

Protein Purification

By Protein A Affinity Chromatography

For the affinity step the supernatant was loaded on a protein A column (HITRAP Protein A FF, 5 mL, GE Healthcare) equilibrated with 6 CV 20 mM sodium phosphate, 20 mM sodium citrate, pH 7.5. After a washing step with the same buffer the antibody was eluted from the column by step elution with 20 mM sodium phosphate, 100 mM sodium chloride, 100 mM Glycine, pH 3.0. The fractions with the desired antibody were immediately neutralized by 0.5 M Sodium Phosphate, pH 8.0 (1:10), pooled and concentrated by centrifugation. The concentrate was sterile filtered and processed further by cation exchange chromatography and/or size exclusion chromatography.

By Cation Exchange Chromatography

For the cation exchange chromatography step the concentrated protein was diluted 1:10 with the elution buffer used for the affinity step and loaded onto a cation exchange colume (POROS 50 HS, APPLIED BIOSYSTEMS). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein was eluted with a gradient using 20 mM sodium phosphate, 20 mM sodium citrate, 20 mM TRIS, 100 mM sodium chloride pH 8.5. The fractions containing the desired antibody were pooled, concentrated by centrifugation, sterile filtered and processed further a size exclusion step.

By Analytical Size Exclusion Chromatography

For the size exclusion step the concentrated protein was injected in a XK16/60 HILOAD SUPERDEX 200 column (GE HEALTHCARE), and 20 mM Histidine, 140 mM Sodium Chloride, pH 6.0 with or without TWEEN20 as formulation buffer. The fractions containing the monomers were pooled, concentrated by centrifugation and sterile filtered into a sterile vial.

Measurement of Purity and Monomer Content

Purity and monomer content of the final protein preparation was determined by CE-SDS (Caliper LABCHIP GXII system (Caliper Life Sciences)) resp. HPLC (TSKGEL G3000 SW XL analytical size exclusion column (TOSOH)) in a 25 mM potassium phosphate, 125 mM Sodium chloride, 200 mM L-arginine monohydrochloride, 0.02% (w/v) Sodium azide, pH 6.7 buffer.

Molecular Weight Confirmation by LC-MS Analyses

Deglycosylation

To confirm homogeneous preparation of the molecules final protein solution of was analyzed by LC-MS analyses. To remove heterogeneity introduced by carbohydrates the constructs are treated with PNGaseF (PROZYME). Therefore the pH of the protein solution was adjusted to pH7.0 by adding 2 µl 2 M Tris to 20 µg protein with a concentration of 0.5 mg/ml. 0.8 µg PNGaseF was added and incubated for 12 h at 37° C.

LC-MS Analysis—On Line Detection

The LC-MS method was performed on an AGILENT HPLC 1200 coupled to a TOF 6441 mass spectrometer (AGILENT). The chromatographic separation was performed on a MACHEREY-NAGEL Polysterene column; RP1000-8 (8 µm particle size, 4.6×250 mm; cat. No. 719510). Eluent A was 5% acetonitrile and 0.05% (v/v) formic acid in water, eluent B was 95% acetonitrile, 5% water and 0.05% formic acid. The flow rate was 1 ml/min, the separation was performed at 40° C. and 6 µg (15 µl) of a protein sample obtained with a treatment as described before (table 7).

TABLE 7

| Time (min.) | % B |
|---|---|
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes the eluate was directed into the waste to protect the mass spectrometer from salt contamination. The ESI-source was running with a drying gas flow of 12 l/min, a temperature of 350° C. and a nebulizer pressure of 60 psi. The MS spectra were acquired using a fragmentor voltage of 380 V and amass range 700 to 3200 m/z in positive ion mode using. MS data were acquired by the instrument software from 4 to 17 minutes.

Isolation of Primary Human Pan T Cells from PBMCs

Peripheral blood mononuclear cells (PBMCs) were prepared by HISTOPAQUE™ density centrifugation from enriched lymphocyte preparations (buffy coats) obtained from local blood banks or from fresh blood from healthy human donors. Briefly, blood was diluted with sterile PBS and carefully layered over a HISTOPAQUE™ gradient (Sigma, H8889). After centrifugation for 30 minutes at 450×g at room temperature (brake switched off), part of the plasma above the PBMC containing interphase was discarded. The PBMCs were transferred into new 50 ml Falcon tubes and tubes were filled up with PBS to a total volume of 50 ml. The mixture was centrifuged at room temperature for 10 minutes at 400×g (brake switched on). The supernatant was discarded and the PBMC pellet washed twice with sterile PBS (centrifugation steps at 4° C. for 10 minutes at 350×g). The resulting PBMC population was counted automatically (VI-CELL) and stored in RPMI1640 medium, containing 10% FCS and 1% L-alanyl-L-glutamine (BIOCHROM, K0302) at 37° C., 5% $CO_2$ in the incubator until assay start.

T cell enrichment from PBMCs was performed using the Pan T Cell Isolation Kit II (MILTENYI BIOTEC #130-091-156), according to the manufacturer's instructions. Briefly, the cell pellets were diluted in 40 µL cold buffer per 10 million cells (PBS with 0.5% BSA, 2 mM EDTA, sterile filtered) and incubated with 10 µL Biotin-Antibody Cocktail per 10 million cells for 10 min at 4° C. 30 µL cold buffer and 20 µL Anti-Biotin magnetic beads per 10 million cells were added, and the mixture incubated for another 15 min at 4° C. Cells were washed by adding 10-20× the current volume and a subsequent centrifugation step at 300×g for 10 min. Up to 100 million cells were resuspended in 500 µL buffer. Magnetic separation of unlabeled human pan T cells was performed using LS columns (MILTENYI BIOTEC #130-042-401) according to the manufacturer's instructions. The resulting T cell population was counted automatically (VI-CELL) and stored in AIM-V medium at 37° C., 5% $CO_2$ in the incubator until assay start (not longer than 24 h).

Isolation of Primary Human Naive T Cells from PBMCs

Peripheral blood mononuclear cells (PBMCs) were prepared by HISTOPAQUE™ density centrifugation from enriched lymphocyte preparations (buffy coats) obtained from local blood banks or from fresh blood from healthy human donors. T-cell enrichment from PBMCs was performed using the Naive $CD8^+$ T cell isolation Kit from MILTENYI BIOTEC (#130-093-244), according to the manufacturer's instructions, but skipping the last isolation step of $CD8^+$ T cells (also see description for the isolation of primary human pan T cells).

Remark: all experiments showing the properties of the bispecific antibodies were performed with the non CV bispecific antibodies. However according to the inventors' knowledge the results for the CV bispecific antibodies according to the invention are the same or substantially similar.

EXAMPLES

Remark: If not mentioned that Mab2 was used as anti-ROR1 antibody and/or as anti-ROR1 Fab in an anti-ROR1/anti-CD3 TCB antibody in the following descriptions of the examples, then Mab1 was used as anti-ROR1 antibody and/or as anti-ROR1 Fab in an anti-ROR1/anti-CD3 TCB antibody.

Example 1—Generation of Anti-ROR1 Antibodies

The protein sequences of the VH and VL regions for an ROR1 antibody of SEQ ID NOs: 2-9 (MAB1) are described in WO2012/075158. Briefly, oligonucleotides encoding the above sequences are joined together via PCR to synthesize cDNAs encoding the VH are VL sequences, respectively, of the anti-ROR1 antibody.

For the generation of anti-ROR1 antibody expression vectors, the variable regions of heavy and light chain DNA sequences were subcloned in frame with either the human IgG1 constant heavy chain or the hum IgG1 constant light chain pre-inserted into the respective generic recipient expression vector optimized for expression in mammalian cell lines. The antibody expression was driven by a chimeric MPSV promoter comprising a CMV enhancer and a MPSV promoter followed by a 5' UTR, an intron and a Ig kappa MAR element. The transcription was terminated by a synthetic polyA signal sequence at the 3' end of the CDS. All vectors carry a 5'-end DNA sequence coding for a leader peptide which targets proteins for secretion in eukaryotic cells. In addition each vector contained an EBV OriP sequence for episomal plasmid replication in EBV EBNA expressing cells.

ROR1 antibodies were expressed by transient polymer-based co-transfection of the respective mammalian expression vectors in HEK293-EBNA cells, which were cultivated in suspension. One day prior to transfection the HEK293-EBNA cells were seeded at 1.5 Mio viable cells/mL in EX-CELL medium, supplemented with 6 mM of L-Glutamine. For every mL of final production volume 2.0 Mio viable cells were centrifuged (5 minutes at 210×g). The supernatant was aspirated and the cells resuspended in 100 µL of CD CHO medium. The DNA for every mL of final production volume was prepared by mixing 1 µg of DNA (Ratio heavy chain:light chain=1:1) in 100 µL of CD CHO medium. After addition of 0.27 µL of polymer solution (1 mg/mL) the mixture was vortexed for 15 seconds and left at room temperature for 10 minutes. After 10 minutes, the resuspended cells and DNA/polymer mixture were put together and then transferred into an appropriate container which was placed in a shaking device (37° C., 5% CO2). After a 3 hours incubation time 800 µL of EX-CELL Medium, supplemented with 6 mM L-Glutamine, 1.25 mM valproic acid and 12.5% Pepsoy (50 g/L), was added for every mL of final Production volume. After 24 hours, 70 µL of Feed solution was added for every mL of final production volume. After 7 days or when the cell viability was equal or lower than 70%, the cells were separated from the supernatant by centrifugation and sterile filtration. The antibodies were purified by an affinity step and one or two polishing steps, being cation exchange chromatography and size exclusion chromatography. When required, an additional polishing step was used. The recombinant anti-ROR1 human antibodies were produced in suspension by polymer-based co-transfecting HEK293-EBNA cells with the mammalian expression vectors. The cells were transfected with two vectors. For the human IgG1 one plasmid encoded the heavy chain and the other plasmid the light chain. One day prior to transfection the HEK293-EBNA cells were seeded at 1.5 Mio viable cells/mL in F17 Medium, supplemented with 6 mM of L-Glutamine.

Example 2—Human B-CLL Cell Line or Primary B-CLL Cells, Multiple Myeloma Cell Line or Mantle Cell Lymphoma Cell Line Expressing ROR1 on their Surface a) Fresh human primary B-CLL cells ($CD19^+$ $CD5^+$) were isolated from blood of CLL patients. Blood is collected from CLL patients after informed consent is given, in accordance with local ethical committee guidelines and the Declaration of Helsinki. Cryopreserved human primary B-CLL cells ($CD19^+$ $CD5^+$) was acquired from ALLCELLS (Alameda, CA, USA). The primary B-CLL cells from patients were lawfully obtained and comply with ethical requirements: (i) obtaining samples from patients diagnosed with CLL is approved by an Institute Reviewing Board (IRB) or Human Subject Committee; (ii) a signed and witnessed informed consent form is obtained from the patient before taking part in the ALLCELLS Diseased Cells Program; (iii) all of the patients diagnosed with the above mentioned diseases are reasonably compensated for their commitment to the program and the compensation is approved by the IRB or Human Subject Committee; (iv) all of the patients are aware that the donated samples may be used for any research applications and waived any rights generated from the research applications. Primary B-CLL cells were grown in RPMI supplemented with 10% fetal bovine serum. ROR1 expression on primary $CD19^+$ $CD5^+$ B-CLL cells was confirmed by flow cytometry using fluorochrome-conjugated anti-human ROR1 antibodies (see Example 3).

b) Human B lymphocyte multiple myeloma cell line RPMI8226 was acquired from ATCC (ATCC CCL-155). RPMI8226 myeloma cells were cultured in DMEM, 10% FCS, 1% Glutamine. ROR1 expression on RPMI8226 cell lines was confirmed by flow cytometry using fluorochrome-conjugated anti-human ROR1 antibodies (see Example 3).

c) Human Mantle cell lymphoma (B cell non-Hodgkin's lymphoma) Rec-Icell line was acquired from ATCC (ATCC CRL-3004). Rec-1 cells were cultured in DMEM, 10% FCS, 1% Glutamine. ROR1 expression on Rec-1 cell lines was confirmed by flow cytometry using fluorochrome-conjugated anti-human ROR1 antibodies (see Example 3).

Example 2.1—Human Ovarian Cancer Cell Lines with Different Levels of Expression of ROR1 on the Cell Surface a) Human ovarian cancer cell line PA-1 derived from ovarian teratocarcinoma was acquired from American Type Culture Collection (ATCC; Cat. No. CRL-1572). PA-1 cell lines were cultured in Eagle's Minimum Essential Medium (MEM) (ATCC, Cat. No. 30-2003) supplemented with 10% fetal bovine serum (heat-inactivated), 2 mM L-glutamine, 1 mM sodium pyruvate, and 1500 mg/L sodium bicarbonate. ROR1 expression was confirmed to be high on PA-1 cell lines as measured by flow cytometry (see Example 3.1).

b) Human ovarian cancer cell line COLO-704 derived from ovarian adenocarcinoma was obtained from Leibniz Institute DSMZ—German Collection of Microorganisms and Cell Cultures (DSMZ; Cat. No. ACC 198). COLO-704 cell lines were cultured in 90% RPMI 1640 and 10% heat inactivated fetal bovine serum. ROR1 expression was confirmed to be medium on COLO-704 cell lines as measured by flow cytometry (see Example 3.1).

c) Human ovarian cancer cell line ES-2 derived from ovarian clear cell carcinoma was acquired from American Type Culture Collection (ATCC; Cat. No. CRL-1978). ES-2 cell lines were cultured in ATCC-formulated McCoy's 5a Medium Modified (Cat. No. 30-2007) and 10% fetal bovine serum. ROR1 expression was confirmed to be negative on ES-1 cell lines as measured by flow cytometry (see Example 3.1).

d) Human ovarian cancer cell line SK-OV-3 derived from ovarian carcinoma was acquired from American Type Culture Collection (ATCC; Cat. No. HTB-77). SK-OV-3 cell lines were cultured in ATCC-formulated McCoy's 5a Medium Modified (Cat. No. 30-2007) and 10% fetal bovine serum. ROR1 expression was confirmed to be low on SK-OV-3 cell lines as measured by flow cytometry (see Example 3.1).

e) Human ovarian cancer cell line OVCAR-5 derived from ovarian adenocarcinoma was obtained from US National Cancer Institute NCI-60 human cancer cell line panel. OVCAR-5 cell lines were cultured in 90% RPMI 1640 and 10% heat inactivated fetal bovine serum. ROR1 expression was confirmed to be medium on OVCAR-5 cell lines as measured by flow cytometry (see Example 3.1).

Figure 2A:
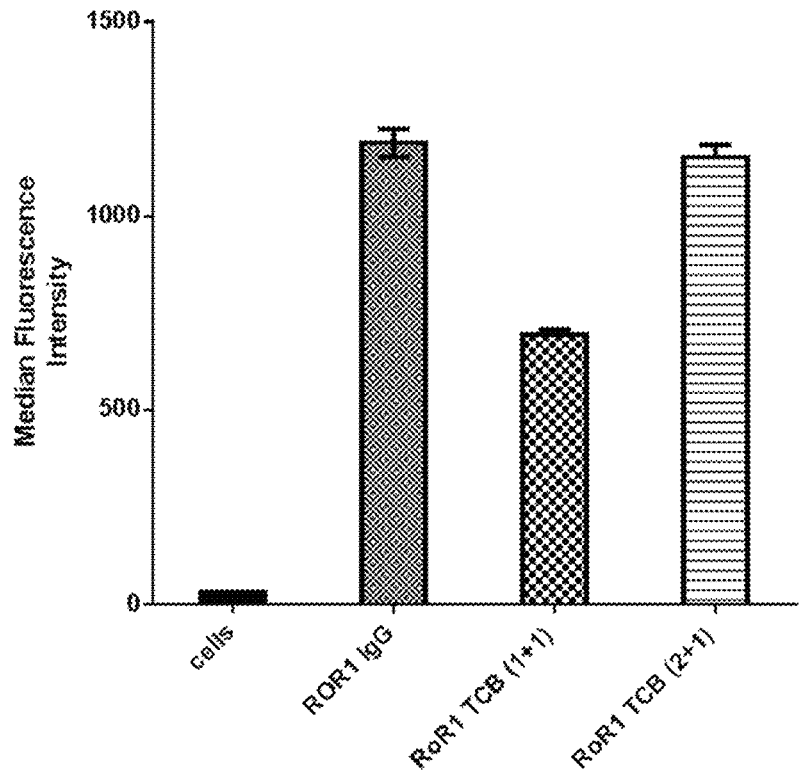
FIG. 2. Detection of ROR1 on the cell surface of (A) primary CLL cells and (B) RPMI8226 MM cells and Rec-1 MCL cells using Alexa488-labelled anti-ROR1IgG antibody or Alexa647-labelled anti-human Fc antibody. Graphs showing increase in MFI signal as compared to baseline.

Example 3—Binding to ROR1 Expressed on Primary B-CLL Cells, RPMI8226 Myeloma Cells or Rec-1 MCL Cells (Flow Cytometry)

a) ROR1 expression was assessed on primary $CD19^+$ $CD5^+$ CLL cells by flow cytometry. Briefly, cells were harvested, washed, counted for viability, resuspended at 50 000 cells/well of a 96-well round bottom plate and incubated with Alexa488-labeled anti human ROR1 antibody at 10 µg/ml for 30 min at 4° C. (to prevent internalization). At the end of incubation time, cells were centrifuged (5 min at 350×g), washed twice with FACS buffer, resuspended in 100 ul FACS buffer and analyzed on a CANTO II device running FACSDIVA software. FIG. 2A shows an increase of median fluorescence intensity upon binding of the anti-ROR1 antibody to primary B-CLL cells, indicating that ROR1 is expressed on primary CLL cells.

b) ROR1 expression was then assessed on B lymphocyte myeloma RPMI8226 cell lines by flow cytometry, using the methods described above. FIG. 3 shows increase of median fluorescence intensity upon binding of increasing concentrations of the anti-ROR1 antibody to RPMI8226 cells (A), but not to ROR1-negative MKN45 cells (human gastric adenocarcinoma cell line, DSMZ ACC 409) (B). Table 1 shows the binding EC50 of anti-ROR1 antibody to ROR1-positive RPMI8226 cell lines.

TABLE 1

Figure 2B:
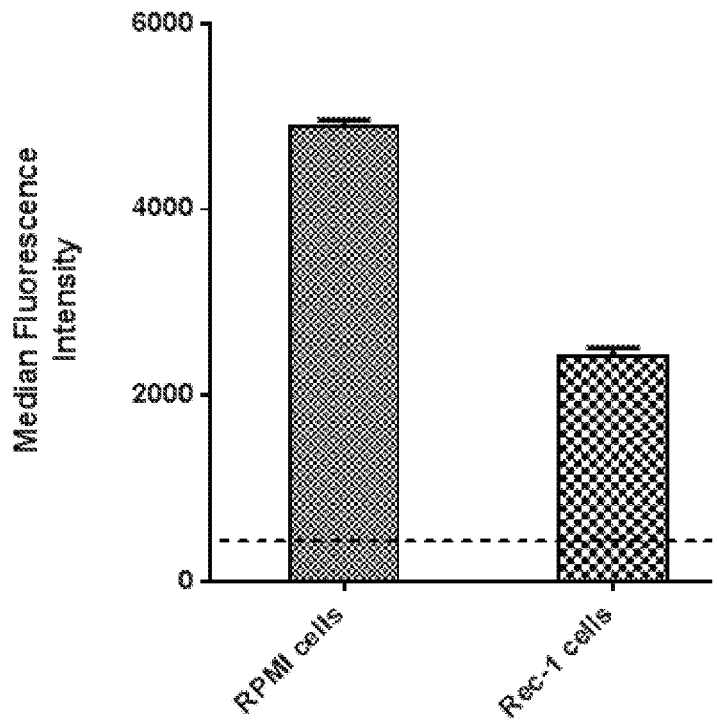
Figure 3A:
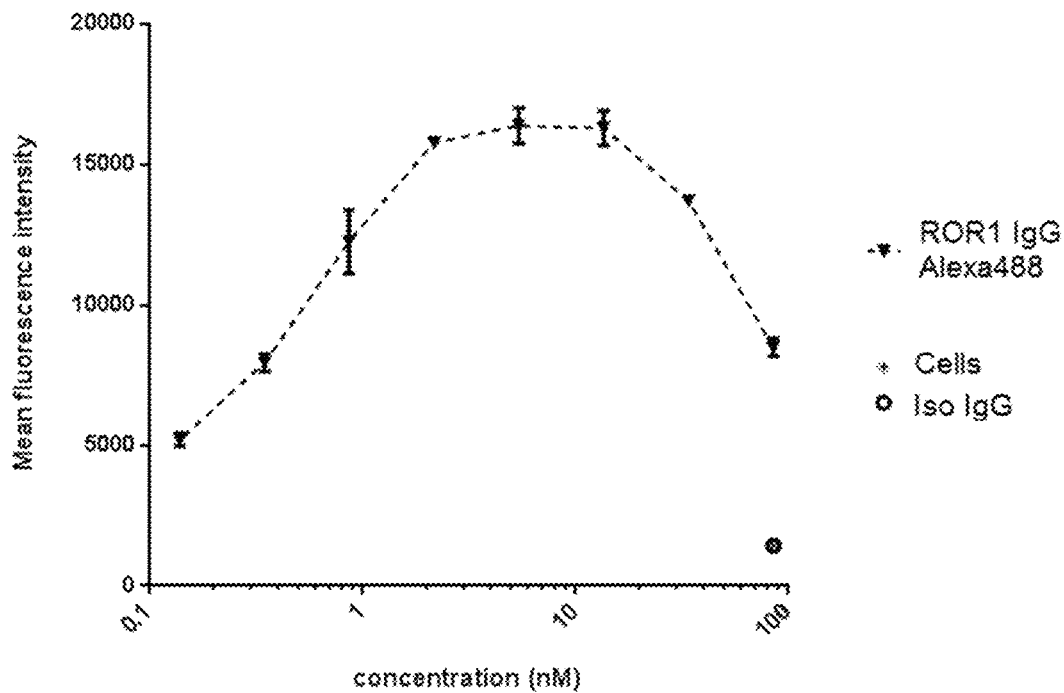
FIGS. 3A-3B. Binding of anti-ROR1 IgG1 antibody on ROR1-positive RPMI8226 cells (3A) and non-binding to ROR1-negative MKN45 cells (3B). Mean fluorescence intensity for anti-ROR1 IgG plotted in function of anti-ROR1 antibody concentrations (from 0.14 to 100 nM).
Figure 3B:
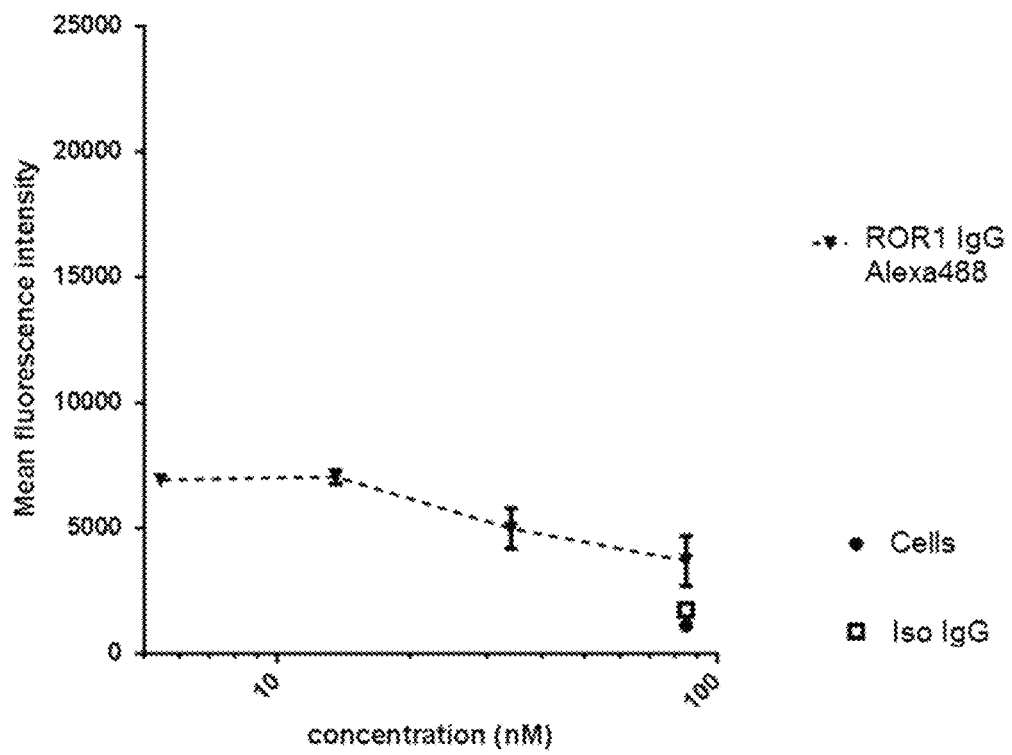
Figure 3F:
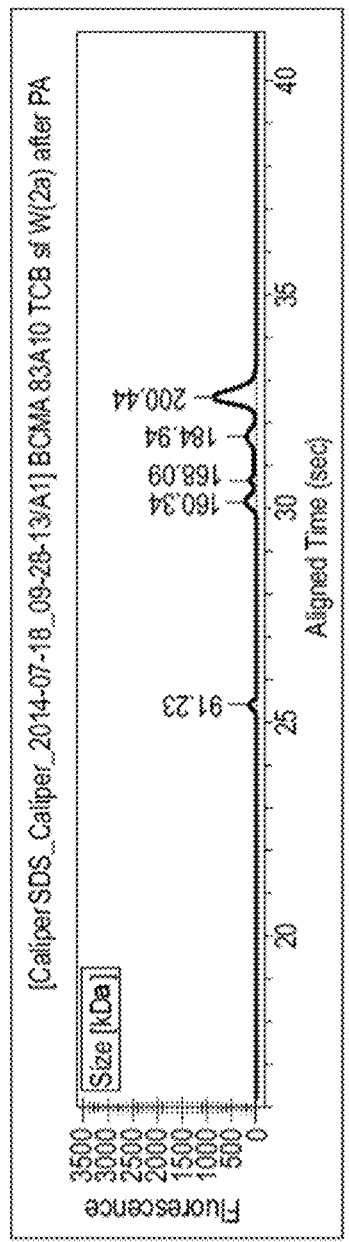
Figure 3G:
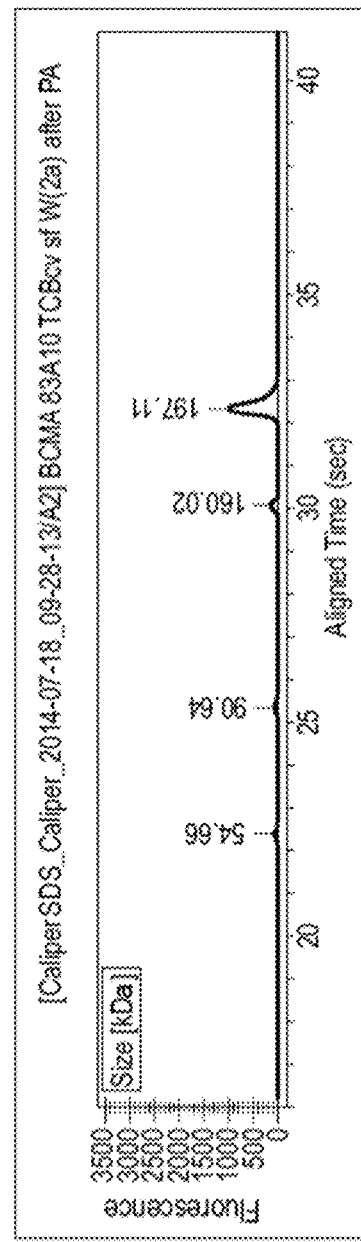
Figure 3L:
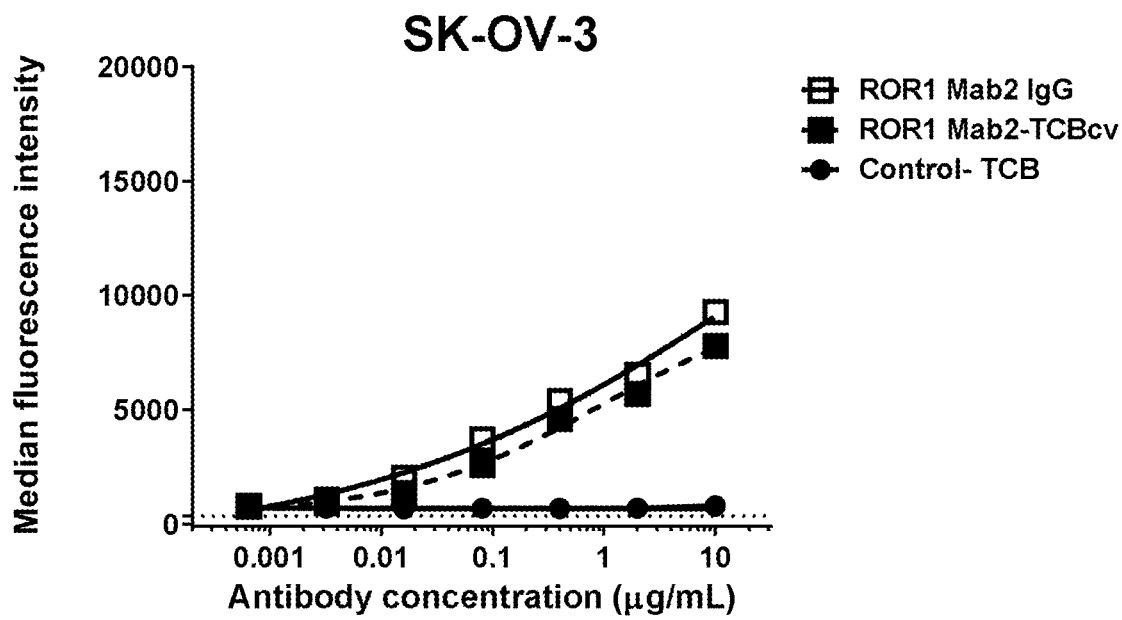
FIGS. 3L-3M. Binding of ROR1 IgG (ROR1 Mab2, open symbols) and anti-ROR1/anti-CD3 TCB antibodies (ROR1 Mab2-TCBcv, closed symbols) to ovarian cancer cell lines SK-OV-3 (3L) and PA-1 (3M) as measured by an increase in the median fluorescence intensity signal in function of antibody concentrations. No signal was observed with the control-TCB binding to CD3 only and not to ROR1 tested on both SK-OV-3 and PA-1 ovarian cancer cell lines (A and B; closed circles).
Figure 3M:
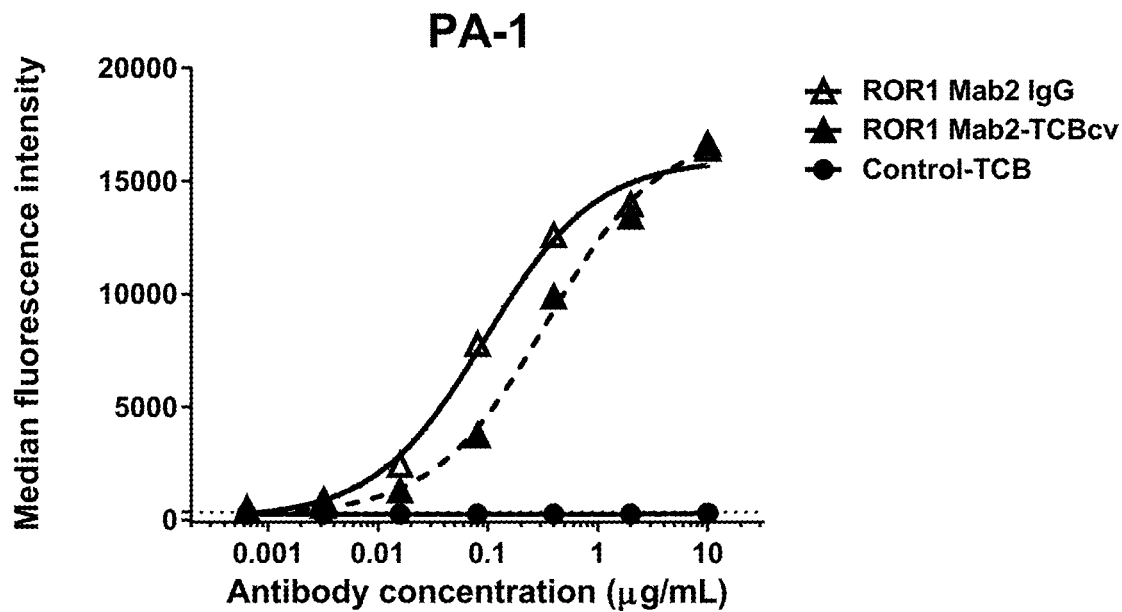
Figure 3N:
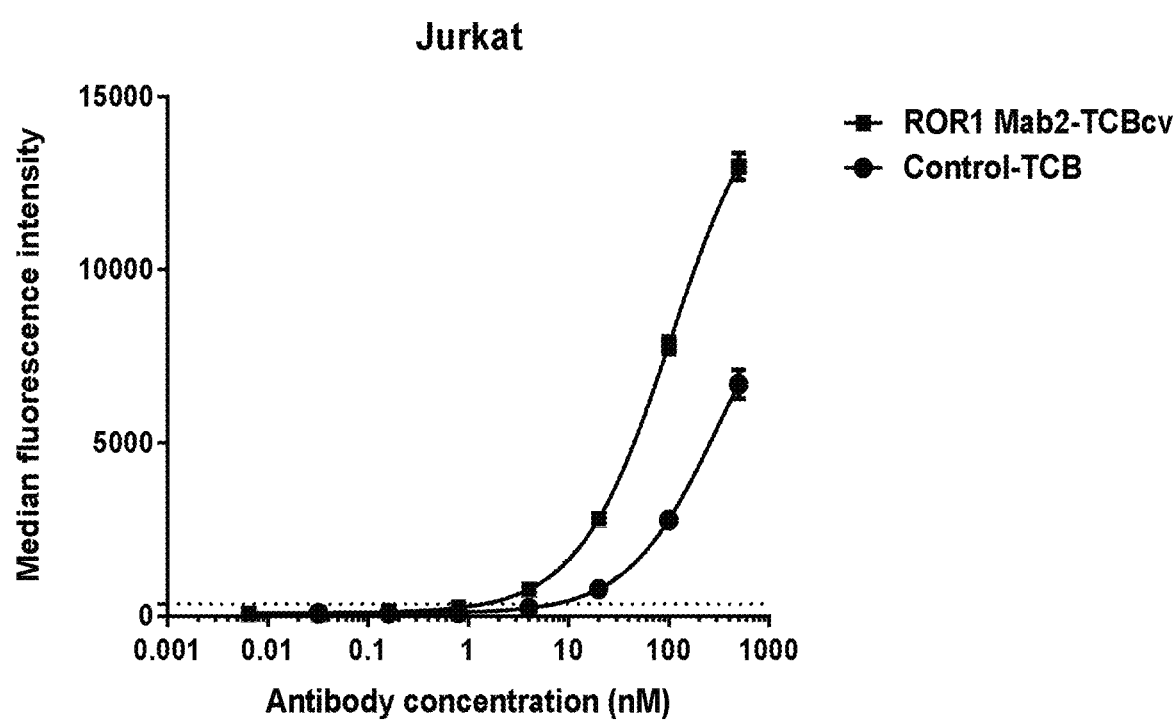
FIG. 3N. Binding of anti-ROR1/anti-CD3 TCB antibodies to Jurkat T cells. A concentration-dependent binding of ROR1 Mab2-TCBcv (squares) and control-TCB (circles) was observed on Jurkat T cells confirming that both TCB antibodies bind to CD3 on T cells.

| EC50 values for binding of anti-ROR1 antibody to RPMI8226 cells | |
|---|---|
| | Anti-ROR1 antibody |
| EC50 (nM) | 0.087 |
| EC50 (µg/ml) | 0.013 | c) ROR1 expression was also tested on MCL Rec-1 cell lines by flow cytometry, using the methods describe above. FIG. 2B shows increase of median fluorescence intensity upon binding of the anti-ROR1 antibody to Rec-1 MCL cells.

Example 3.1—Binding of ROR1 IgG Antibodies to ROR1-Positive Human Ovarian Cancer Cell Lines (as Detected by Flow Cytometry)

a) The level of expression of ROR1 was measured on human ovarian cancer cell lines by flow cytometry including PA-1, COLO-704, ES-2, SK-OV-3, and OVCAR-5. Briefly, cells were harvested, washed, counted for viability, resuspended at 50,000 cells/well of a 96-well round bottom plate and incubated with Alexa488-labeled anti human ROR1 antibody for 30 min at 4° C. All ROR1 and isotype control antibodies were titrated and analyzed in final concentration range between 0.01-100 nM (0.0015-15 µg/mL). For samples using non-labelled antibodies, cells were centrifuged (5 min, 350×g), washed with 120 pl/well FACS Stain Buffer (BD Biosciences), resuspended and incubated for an additional 30 min at 4° C. with fluorochrome-conjugated AlexaFluor™ 647-conjugated AffiniPure™ F(ab')2 Fragment goat anti-human IgG Fc Fragment Specific (Jackson Immuno Research Lab; #109-606-008). At the end of incubation time, cells were centrifuged (5 min at 350×g), washed twice with FACS buffer, resuspended in 100 ul FACS buffer and analyzed on a CANTO II device running FACSDIVA software. Expression of ROR1 was then quantified as the median fluorescence intensity (MFI) and graphs showing the MFI in function of ROR1 antibody concentrations were plotted. EC50 values were then measured using PRISM software (GRAPHPAD). Table 2 shows the binding EC50 of Mab1 and Mab2 anti-RORI antibodies to ROR 1-positive SK-OV-3 and PA-1 ovarian cancer cell lines. Both Mab1 and Mab?2 anti-RORI1 antibodies bind with more potency to PA-1 cell lines (later found to express high level of ROR1) than SK-OV-3 (later found to express low level of ROR1). The calculated EC50s for binding of ROR1 Mab1 and ROR1 Mab2 to SK-OV-3 are extrapolated values and may be over- or underestimated. FIG. 3-3 shows an increase of MFI on SK-OV-3 cells (A, open squares) and PA-1 cells (B, open triangles) in function of the concentrations of ROR1 Mab2 IgG. Maximum intensity could be reached approximately 3 times more in PA-1 cells vs. SK-OV-3 cells with an antibody concentration of 10 μg/mL.

TABLE 2

EC50 values for binding of anti-ROR1 antibodies to ovarian cancer cell lines

| Ovarian cancer cell lines | Binding EC50 | |
|---|---|---|
| | ROR1 Mab1 | ROR1 Mab2 |
| SK-OV-3 | ~4.62 nM/0.69 μg/ml | ~357.6 nM/53.37 μg/ml |
| PA-1 | 0.87 nM/0.13 μg/ml | 0.64 nM/0.095 μg/ml | b) To determine ROR1 antigen copy number on the cell surface of human ovarian cancer cell PA-1, COLO-704, ES-2, SK-OV-3, and OVCAR-5, the QIFIKIT (DAKO #K0078) method was used. Ovarian tumor cells were once washed with FACS buffer (100 μl/well; 350×g for 5 min) and adjusted to 1 Mio cells/ml. 50 μl (=0.5 Mio cells) of the cell suspension were transferred into each well of a 96 round bottom well plate, as indicated.

Then, 50 μl of mouse anti-human ROR1 IgG antibody (BIOLEGEND #357802) or a mouse IgG2a isotype control antibody (BIOLEGEND #401501) diluted in FACS buffer (PBS, 0.1% BSA) to a final concentration of 25 μg/ml (or at saturation concentrations) were added and staining was performed for 30 min at 4° C. in the dark. Next, 100 μl of the Set-up or Calibration Beads were added in separate wells and the cells, as well as the beads were washed twice with FACS buffer. Cells and beads were resuspended in 25 μl FACS buffer, containing fluorescein conjugated anti-mouse secondary antibody (at saturation concentrations), provided with the QIFIKIT. Cells and beads were stained for 45 min at 4° C. in the dark. The cells were washed once and all samples were resuspended in 100 μl FACS buffer. Samples were analyzed on a multicolor flow cytometer and installed software (e.g. CANTO II device running FACSDIVA software).

As shown in Table 2.1, ROR1 antigen copy number/binding sites were measured on five human ovarian cancer cell lines (ES-2, SK-OV-3, OVCAR-5, COLO-704 and PA-1) and expressed at different levels. ES-2 cells did not express any antigen copy of human ROR1 while S-KOV-3 cells expressed low level of human ROR1, OVCAR-5 and COLO-704 cells expressed medium level of human ROR1 and PA-1 cells expressed high level of human ROR1. In light of these ROR1 expression results, human ovarian cancer cell lines with high, medium and/or low expression level of ROR1 will be selected and used in the redirected T-cell cytotoxicity assay as tumor target cells in Example 10.

TABLE 2.1

ROR1 antigen copy number/binding sites on human ovarian cancer cell lines as measured by quantitative flow cytometry

| Human ovarian cancer cell lines | ROR1 antigen copy number/ binding sites | ROR1 level of expression |
|---|---|---|
| ES-2 | 0 | Negative |
| SK-OV-3 | 3210 | Low |
| OVCAR-5 | 5034 | Medium |
| Colo704 | 6409 | Medium |
| PA-1 | 14106 | High |

Example 4—Internalization of Anti-ROR1 Antibody on Primary PBMC from CLL Patients or RPMI8226 MM Cells (Flow Cytometry)

Anti-ROR1 antibodies were further tested in the internalization assay. Briefly, human ROR1-expressing primary B-CLL target cells were harvested with Cell Dissociation Buffer, washed and resuspended in RPMI supplemented with 10% FCS at a concentration of $1 \times 10^6$ ($1 \times 10^6$/mL) of PBMC from untreated CLL patients or $1 \times 10^6$ cells/mL RPMI8226 cells after determination of cell viability using VI-CELL. The cell suspension was transferred in a 15 ml Falcon tube for each tested IgG/TCB and each concentration. 0.5 ml of diluted anti-ROR1 IgG or anti-ROR1/anti-CD3 TCBs conjugated with Alexa488 (diluted to 1 nM in RPMI+10% FCS) were added to the tubes and incubated for 30 min in the cold room on a shaker. After incubation and washing the cells three times with cold PBS to remove unbound antibody, the cells were either left on ice or transferred ($0.1 \times 10^6$ cells) in 96-well FACS plate in pre-warmed medium and incubated at 37° C. for 15 min, 30 min, 1 h, 2 h, and 24 h to facilitate internalization. In addition, sample of cells were also incubated at 37° C. for 2 h and/or 24 h in the presence of 3 μM phenylarsine oxide (SIGMA-ALDRICH) to inhibit internalization. Subsequently, the cells were washed once with cold PBS and incubated with Alexa647-labeled anti-human Fc secondary antibody $(F(ab)^2)$ for 30 min at 4° C. After three final washes with PBS, the cells were centrifuged 4 min at 400×g and resuspended in FACS buffer with or without propidium iodide (1:4000) (Sigma). The mean fluorescence intensity (MFI) of the cells for anti-ROR1 IgG and anti-ROR1/anti-CD3 TCBs was measured using a FACSCANTO II flow cytometer (BD Biosciences) and FLOWJO analytical software.

MFI reduction can represent antibody internalization, antibody dissociation or a combination of both. The percentage of MFI reduction is calculated for each ROR1 antibodies relative to the unspecific human IgG control ($MFI_{background}$) and ROR1 antibodies maintained on ice ($MFI_{max}$) by using the formula $\Delta MFI = 100 - 100 \times [(MFI_{experimental} - MFI_{background})/(MFI_{max} - MFI_{background})]$. An MFI reduction which is blocked by endocytosis inhibitor phenylarsine oxide indicates antibody internalization while an MFI reduction which is not blocked by phenylarsine oxide reflects antibody dissociation. Internalizing anti-ROR1 antibodies are known in the state of the art (Baskar et al., Clin. Cancer Res., 14(2): 396-404 (2008)).

For antibody-based therapies such as T cell bispecifics, it is important that the antibody or antibody fragment specific to the tumor target do not internalize, or slowly internalize, or slightly internalize for facilitating a stable immune synapse between the tumor cell and the T cell and effective T cell-mediated redirected cytotoxicity. Thus, anti-ROR1 antibodies which does not internalize or slowly internalize or slightly internalize are selected for the next step (Example 5) below, namely the production of anti-ROR1/anti-CD3 T cell bispecific antibodies.

The internalization values of anti-ROR1 IgG antibody in primary CLL cells and RPMI8226 cells are further summarized in FIGS. 4 and 6 and Tables 4 and 6.

Example 5—Generation of Anti-ROR1/Anti-CD3 T Cell Bispecific Antibodies

Example 5.1. Generation of Anti-CD3 Antibodies

The following protein sequences of the VH and VL regions were used to generate human and cynomolgus monkey cross reactive CD3ε antibodies.

```
CH2527_VH (SEQ ID NO: 21):
EVQLLESGGGLVQPGGSLRLSCAASGFTFSTYAMNWVRQAPGKGLEWVSR
IRSKYNNYATYYADSVKGRFTISRDDSKNTLYLQMNSLRAEDTAVYYCVR
HGNFGNSYVSWFAYWGQGTLVTVSS

CH2527_VL (SEQ ID NO: 22)
QAVVTQEPSLTVSPGGTVTLTCGSSTGAVTTSNYANWVQEKPGQAFRGLI
GGTNKRAPGTPARKSGSLLGGKAALTLSGAQPEDEAEYYCALWYSNLWVF
GGGTKLTVL
```

Briefly, oligonucleotides encoding the above sequences were joined together via PCR to synthesize cDNAs encoding the VH and VL sequences, respectively, of the anti-CD3 antibody.

Anti-CD3 antibody CH2527 (SEQ ID NO:21-28) was used to generate the T cell bispecific antibodies which were used in the following examples.

Example 5.2. Generation of Anti-ROR1/Anti-CD3 T Cell Bispecific 1+1 Format (i.e. One-Arm Bispecific (Fab)×(Fab) Antibody Monovalent for ROR1 and Monovalent for CD3)

a) An anti-ROR1/anti-CD3 T cell bispecific antibody according to the invention would have the advantage of an elimination half-life of about 1 to 12 days which allows at least once or twice/week administration.

Anti-ROR1/anti-CD3 T cell bispecific of the 1+1 one-arm format (i.e. bispecific (Fab)×(Fab) antibody monovalent for ROR1 and monovalent for CD3) are produced with the anti-ROR1 antibodies generated from Example 1. cDNAs encoding the full Fabs (heavy chain VH and CH1 domains plus light chain VL and CL domains) of the corresponding anti-ROR1 IgG1 antibodies, as described in Example 1, as well as the anti-CD3 VH and VL cDNAs described in Example 5.1, are used as the starting materials. For each bispecific antibody, four protein chains are involved comprising the heavy and light chains of the corresponding anti-ROR1 antibody and the heavy and light chains of the anti-CD3 antibody described above.

b) For the generation of ROR1×CD3 bispecific antibody vectors, the IgG1 derived bispecific molecules consist at least of two antigen binding moieties capable of binding specifically to two distinct antigenic determinants CD3 and ROR1. The antigen binding moieties are Fab fragments composed of a heavy and a light chain, each comprising a variable and a constant region. At least one of the Fab fragments is a "Crossfab" fragment, wherein the constant domains of the Fab heavy and light chain are exchanged. The exchange of heavy and light chain constant domains within the Fab fragment assures that Fab fragments of different specificity do not have identical domain arrangements and consequently do not interchange light chains. The bispecific molecule design can be monovalent for both antigenic determinants (1+1) or monovalent for CD3 and bivalent for ROR1 where one Fab fragment is fused to the N-terminus of the inner CrossFab (2+1). A schematic representation of the constructs is given in FIG. 1. Sequences of the constructs are shown in SEQ ID NOs 2 to 36. The molecules are produced by polymer-based co-transfecting HEK293 EBNA cells growing in suspension with the mammalian expression. For preparation of 1+1 CrossFab-IgG constructs, cells are transfected with the corresponding expression vectors in a 1:1:1:1 ratio ("vector Fc(knob)": "vector light chain":"vector light chain CrossFab":"vector heavy chain-CrossFab").

Example 5.3. Generation of Anti-ROR1/Anti-CD3 T Cell Bispecific 2+1 Format (i.e. Bispecific (Fab)$_2$×(Fab) Antibody Bivalent for ROR1 and Monovalent for CD3)

a) An anti-ROR1/anti-CD3 T cell bispecific antibody with a 2+1 format i.e. bispecific (Fab)$_2$×(Fab) antibody that is bivalent for ROR1 and monovalent for CD3 would have advantages on potency, predictability for efficacy and safety because it would preferentially bind to the tumor target ROR1 and avoid CD3 antibody sink, thus higher probability for drug exposure focused to the tumor.

Anti-ROR1/anti-CD3 T cell bispecific of the 2+1 format (i.e. bispecific (Fab)$_2$×(Fab) antibody bivalent for ROR1 and monovalent for CD3 are produced with the anti-ROR1 antibodies generated in Example 1. cDNAs encoding the full Fabs (heavy chain VH and CH1 domains plus light chain VL and CL domains) of the corresponding anti-ROR1 IgG1 antibodies, as described in Example 1, as well as the anti-CD3 VH and VL cDNAs described in Example 5.1, are used as the starting materials. For each bispecific antibody, four protein chains are involved comprising the heavy and light chains of the corresponding anti-ROR1 antibody and the heavy and light chains of the anti-CD3 antibody described above.

b) For the generation of ROR1×CD3 bispecific antibody vectors, the IgG1 derived bispecific molecules consist at least of two antigen binding moieties capable of binding specifically to two distinct antigenic determinants CD3 and ROR1. The antigen binding moieties are Fab fragments composed of a heavy and a light chain, each comprising a variable and a constant region. At least one of the Fab fragments is a "Crossfab" fragment, wherein the constant domains of the Fab heavy and light chain are exchanged. The exchange of heavy and light chain constant domains within the Fab fragment assures that Fab fragments of different specificity do not have identical domain arrangements and consequently do not interchange light chains. The bispecific molecule design can be monovalent for both antigenic determinants (1+1) or monovalent for CD3 and bivalent for ROR1 where one Fab fragment is fused to the N-terminus of the inner CrossFab (2+1). A schematic representation of the constructs is given in FIG. 1; Sequences of the constructs are shown in SEQ ID NOs 1 to 62. The molecules are produced by polymer-based co-transfecting HEK293 EBNA cells growing in suspension with the mammalian expression. For preparation of 2+1 CrossFab-IgG constructs, cells are transfected with the corresponding expression vectors in a 1:2:1:1 ratio ("vector Fc(knob)": "vector light chain":"vector light chain CrossFab":"vector heavy chain-CrossFab").

Example 5.4. Production and Purification of Anti-ROR1/Anti-CD3 T Cell Bispecific Antibodies with or without Charge Variants For the production of the bispecific antibodies, bispecific antibodies are expressed by transient polymer-based co-transfection of the respective mammalian expression vectors in HEK293-EBNA cells, which are cultivated in suspension. One day prior to transfection the HEK293-EBNA cells are seeded at 1.5 Mio viable cells/mL in EX-CELL medium, supplemented with 6 mM of L-Glutamine. For every mL of final production volume 2.0 Mio viable cells are centrifuged (5 minutes at 210×g). The supernatant is aspirated and the cells resuspended in 100 µL of CD CHO medium. The DNA for every mL of final production volume is prepared by mixing 1 µg of DNA (Ratio heavy chain:modified heavy chain:light chain:modified light chain=1:1:2:1) in 100 µL of CD CHO medium. After addition of 0.27 µL of polymer solution (1 mg/mL) the mixture is vortexed for 15 seconds and left at room temperature for 10 minutes. After 10 minutes, the resuspended cells and DNA/polymer mixture are put together and then transferred into an appropriate container which is placed in a shaking device (37° C., 5% $CO_2$). After a 3 hours incubation time 800 µL of EX-CELL Medium, supplemented with 6 mM L-Glutamine, 1.25 mM valproic acid and 12.5% Pepsoy (50 g/L), is added for every mL of final Production volume. After 24 hours, 70 µL of Feed solution is added for every mL of final production volume. After 7 days or when the cell viability is equal or lower than 70%, the cells are separated from the supernatant by centrifugation and sterile filtration. The antibodies are purified by an affinity step and one or two polishing steps, being cation exchange chromatography and size exclusion chromatography. When required, an additional polishing step is used.

For the affinity step the supernatant is loaded on a protein A column (HITRAP Protein A FF, 5 mL, GE HEALTHCARE) equilibrated with 6 CV 20 mM sodium phosphate, 20 mM sodium citrate, pH 7.5. After a washing step with the same buffer the antibody is eluted from the column by step elution with 20 mM sodium phosphate, 100 mM sodium chloride, 100 mM Glycine, pH 3.0. The fractions with the desired antibody are immediately neutralized by 0.5 M Sodium Phosphate, pH 8.0 (1:10), pooled and concentrated by centrifugation. The concentrate is sterile filtered and processed further by cation exchange chromatography and/or size exclusion chromatography.

For the cation exchange chromatography step the concentrated protein is diluted 1:10 with the elution buffer used for the affinity step and loaded onto a cation exchange colume (POROS 50 HS, Applied Biosystems). After two washing steps with the equilibration buffer and a washing buffer resp. 20 mM sodium phosphate, 20 mM sodium citrate, 20 mM TRIS, pH 5.0 and 20 mM sodium phosphate, 20 mM sodium citrate, 20 mM TRIS, 100 mM sodium chloride pH 5.0 the protein is eluted with a gradient using 20 mM sodium phosphate, 20 mM sodium citrate, 20 mM TRIS, 100 mM sodium chloride pH 8.5. The fractions containing the desired antibody are pooled, concentrated by centrifugation, sterile filtered and processed further a size exclusion step.

For the size exclusion step the concentrated protein is injected in a XK16/60 HILOAD SUPERDEX 200 column (GE HEALTHCARE), and 20 mM Histidine, 140 mM Sodium Chloride, pH 6.0 with or without TWEEN20) as formulation buffer. The fractions containing the monomers are pooled, concentrated by centrifugation and sterile filtered into a sterile vial.

Determination of the antibody concentration is done by measurement of the absorbance at 280 nm, using the theoretical value of the absorbance of a 0.10% solution of the antibody. This value is based on the amino acid sequence and calculated by GPMAW software (Lighthouse data).

Purity and monomer content of the final protein preparation is determined by CE-SDS (Caliper LABCHIP GXII system (Caliper Life Sciences)) resp. HPLC (TSKGEL G3000 SW XL analytical size exclusion column (Tosoh)) in a 25 mM potassium phosphate, 125 mM Sodium chloride, 200 mM L-arginine monohydrochloride, 0.02% (w/v) Sodium azide, pH 6.7 buffer.

To verify the molecular weight of the final protein preparations and confirm the homogeneous preparation of the molecules final protein solution, liquid chromatography-mass spectometry (LC-MS) is used. A deglycosylation step is first performed. To remove heterogeneity introduced by carbohydrates, the constructs are treated with PNGaseF (PROZYME). Therefore, the pH of the protein solution is adjusted to pH7.0 by adding 2 µl 2 M Tris to 20 µg protein with a concentration of 0.5 mg/ml. 0.8 µg PNGaseF is added and incubated for 12 h at 37° C. The LC-MS online detection is then performed. LC-MS method is performed on an AGILENT HPLC 1200 coupled to a TOF 6441 mass spectrometer (AGILENT). The chromatographic separation is performed on a MACHEREY-NAGEL Polysterene column; RP1000-8 (8 µm particle size, 4.6×250 mm; cat. No. 719510). Eluent A is 5% acetonitrile and 0.05% (v/v) formic acid in water, eluent B was 95% acetonitrile, 5% water and 0.05% formic acid. The flow rate was 1 ml/min, the separation is performed at 40° C. and 6 µg (15 µl) of a protein sample obtained with a treatment as described before (table 8).

TABLE 8

| Time (min.) | % B |
| --- | --- |
| 0.5 | 15 |
| 10 | 60 |
| 12.5 | 100 |
| 14.5 | 100 |
| 14.6 | 15 |
| 16 | 15 |
| 16.1 | 100 |

During the first 4 minutes, the eluate is directed into the waste to protect the mass spectrometer from salt contamination. The ESI-source was running with a drying gas flow of 12 l/min, a temperature of 350° C. and a nebulizer pressure of 60 psi. The MS spectra are acquired using a fragmentor voltage of 380 V and a mass range 700 to 3200 m/z in positive ion mode using. MS data are acquired by the instrument software from 4 to 17 minutes.

A head-to-head production run to compare the production/purification profile of ROR1×CD3-TCB without charge variant vs. ROR1×CD3-TCBcv (with charge variants) antibodies is then conducted to further evaluate the advantages of the CL-CH1 charge modifications applied to the T cell bispecific antibodies.

Table 8-1 shows the favorable production/purification profile of three molecules of ROR1×CD3-TCB with charge variants following standard, non-optimized purification methods including Protein A (PA) affinity chromatography and size exclusion chromatographic (SEC) purification.

TABLE 8-1

Production/purification profile of anti-ROR1/anti-CD3 T cell bispecific antibodies with charge variants following standard, non-optimized purification methods

| | Titer (mg/L) | Monomer content (%) | Purity (%) |
|---|---|---|---|
| Mab2 ROR1-TCBcv | 40.71 | 100 | 98.66 |
| Mab3 ROR1-TCBcv | 104.12 | 100 | 93.78 |
| Mab4 ROR1-TCBcv | 25.36 | 99.03 | 97.69 |

FIG. 3-1 depicts the CE-SDS (non-reduced) graphs of the final protein preparations after different methods of purification for another TCB molecule without or with charge variants namely 83A10-TCB and 83A10-TCBcv antibodies. Protein A (PA) affinity chromatography and size exclusion chromatographic (SEC) purification steps applied to 83A10-TCB antibody resulted in a purity of <30% and 82.8% of monomer content (A). When additional purifications steps including cation exchange chromatography (cIEX) and a final size exclusion chromatographic (re-SEC) steps were applied to the final protein preparations in (A), the purity was increased to 93.4% but the monomer content remained the same and the yield was significantly reduced to 0.42 mg/L. However, when specific charge modifications were applied to 83A10 anti-BCMA Fab CL-CH1, namely 83A10-TCBcv antibody, a superior production/purification profile of the TCB molecule, as demonstrated by a purity of 95.3%, monomer content of 100% and yield of up to 3.3 mg/L, could already be observed even when PA+cIEX+SEC purification steps were applied (C) in comparison to (B) with a production/purification profile showing a 7.9-fold lower yield and 17.2% lower monomer content despite including an additional re-SEC purification step.

A head-to-head production run to compare the production/purification profile of 83A10-TCB vs. 83A10-TCBcv antibodies was then conducted to further evaluate the advantages of the CL-CH1 charge modifications applied to the antibodies. 83A10-TCB and 83A10-TCBcv molecules are both of molecular format as described in FIG. 2a of PCT/EP2015/067841. As depicted in FIG. 3-2, properties of 83A10-TCB and 83A10-TCBcv antibodies were measured side-by-side and compared after each purification steps 1) PA affinity chromatography only (A, B), 2) PA affinity chromatography then SEC (C, D) and 3) PA affinity chromatography then SEC then cIEX and re-SEC (E, F). The CE-SDS (non-reduced) graphs of the final protein solutions after the respective methods of purification for 83A10-TCB and 83A10-TCBcv antibodies are demonstrated in FIG. 3-2. As shown in FIGS. 3-2A and 3-2B, improvements with applying the charge variants to the TCB antibody were already observed after purification by PA affinity chromatography only. In this head-to-head study, PA affinity chromatography purification step applied to 83A10-TCB antibody resulted in a purity of 61.3%, a yield of 26.2 mg/L and 63.7% of monomer content (3-2A). In comparison, when 83A10-TCBcv antibody was purified by PA affinity chromatography all the properties were improved with a better purity of 81.0%, a better yield of 51.5 mg/L and 68.2% of monomer content (3-2B). When an additional SEC purification step was applied to the final protein preparations as seen in FIGS. 3-2A and 3-2B, 83A10-TCB gained a purity of 69.5%, a yield of 14.1 mg/L and 74.7% of monomer content (3-2C) as compared to 83A10-TCBcv with improved purity and monomer content of up to 91.0% and 83.9% respectively, and a yield of 10.3 mg/L (3-2D). Even though the yield was slightly less (i.e. 27% less) for 83A10-TCBcv than for 83A10-TCB in this particular experiment, the percentage of correct molecule was much better for 83A10-TCBcv than for 83A10-TCB, respectively 90% vs. 40-60%, as measured by LC-MS. In the third head-to-head comparison, 83A10-TCB and 83A10-TCBcv final protein preparations from FIGS. 3-2C and 3-2D were pooled with approximately 1 L (equivolume) of respective final protein preparations from another purification batch (same production) following PA affinity chromatography purification step only. The pooled protein preparations were then being further purified by cIEX and SEC purification methods. As depicted in FIGS. 3-2E and 3-2F, improvement of the production/purification profile of the TCB antibody with the charge variants was consistently observed when compared to TCB antibody without charge variant. After several steps of purification methods (i.e. PA+/−SEC+cIEX+SEC) were used to purify 83A10-TCB antibody, only 43.1% purity was reached and 98.3% of monomer content could be achieved but to the detriment of the yield which was reduced to 0.43 mg/L. The percentage of correct molecule as measured by LC-MS was still poor with 60-70%. At the end, the quality of the final protein preparation was not acceptable for in vitro use. In stark contrast, when the same multiple purification steps with the same chronology were applied to 83A10-TCBcv antibody, 96.2% purity and 98.9% of monomer content were reached as well as 95% of correct molecule as measured by LC-MS. The yield however was also greatly reduced to 0.64 mg/L after cIEX purification step. The results show that better purity, higher monomer content, higher percentage of correct molecule and better yield can be achieved with 83A10-TCBcv antibody only after two standard purification steps i.e. PA affinity chromatography and SEC (FIG. 3-2D) while such properties could not be achieved with 83A10-TCB even when additional purification steps were applied (FIG. 3-2E).

Table 8-2 summarizes the properties of 83A10-TCB as compared to 83A10-TCBcv following PA purification step. Table 8-3 summarizes the properties of 83A10-TCB as compared to 83A10-TCBcv following PA and SEC purification steps. Table 8-4 summarizes the properties of 83A10-TCB as compared to 83A10-TCBcv following PA and SEC plus PA alone then cIEX and re-SEC purification steps. For Tables 8-2 to 8-4, the values in bold highlight the superior property as compared between 83A10-TCB vs. 83A10-TCBcv. With one exception (i.e. yield respectively amount, see Table 8-3) which may not be representative, all the production/purification parameters and values resulting from the 3 head-to-head comparison experiments were superior for 83A10-TCBcv as compared to 83A10-TCB. The overall results clearly demonstrate that advantages in production/purification features could be achieved with applying CL-CH1 charge modifications to TCB antibodies and that only two purification steps (i.e PA affinity chromatography and SEC) were required to achieve already high quality protein preparations with very good developability properties.

TABLE 8-2

Production/purification profile of anti-BCMA/anti-CD3 T cell bispecific antibodies following protein A affinity chromatography purification step

|  | 83A10-TCB | 83A10-TCBcv |
|---|---|---|
| Purity (%) | 61.3 | 81.0 |
| Yield (mg/L) | 26.2 | 51.5 |
| Amount (mg) | 24.3 | 50.2 |
| Monomer (%) | 63.7 | 68.2 |
| Correct molecule by LC-MS (%) | n.d. | n.d |

TABLE 8-3

Production/purification profile of anti-BCMA/anti-CD3 T cell bispecific antibodies following protein A affinity chromatography and size exclusion chromatography purification steps

|  | 83A10-TCB | 83A10-TCBcv |
|---|---|---|
| Purity (%) | 69.5 | 91.0 |
| Yield (mg/L) | 14.1 | 10.3 |
| Amount (mg) | 13.1 | 10.0 |
| Monomer (%) | 74.7 | 83.9 |
| Correct molecule by LC-MS (%) | 40-60 | 90 |

TABLE 8-4

Production/purification profile of anti-BCMA/anti-CD3 T cell bispecific antibodies following 1.a) protein A affinity chromatography and size exclusion chromatography and 1.b) protein A affinity chromatography only pooled together then 2) cation exchange chromatography and 3) final size exclusion chromatography purification steps

|  | 83A10-TCB | 83A10-TCBcv |
|---|---|---|
| Purity (%) | 43.1 | 96.2 |
| Yield (mg/L) | 0.43 | 0.64 |
| Amount (mg) | 0.73 | 1.27 |
| Monomer (%) | 98.3 | 98.9 |
| Correct molecule by LC-MS (%) | 60-70% | >95% |

Figure 8:
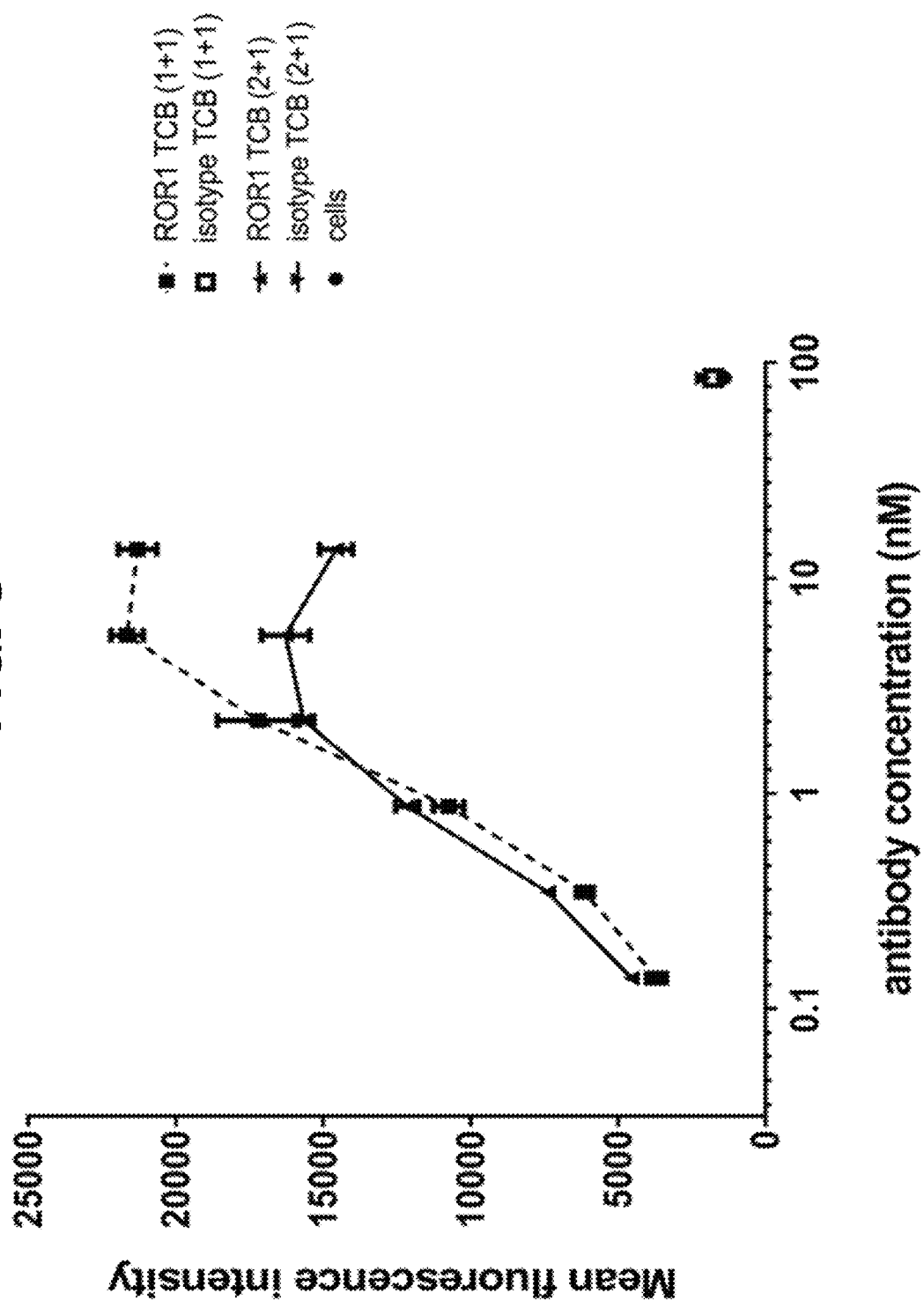
FIG. 8. Binding of anti-ROR1/anti-CD3 TCB antibodies on ROR1-positive RPMI8226 cells. Mean fluorescence intensity plotted in function of antibody concentrations (from 0.136 to 13.6 nM).

Example 6—Binding of Anti-ROR1/Anti-CD3 T Cell Bispecific Antibodies to ROR1-Positive B-CLL Cells or Myeloma Cells or CD3 on T Cells (Flow Cytometry)

a) Anti-ROR1/anti-CD3 T cell bispecific antibodies generated in Example 5 were also analyzed by flow cytometry for their binding properties to human ROR1 expressed on primary B-CLL cells or human CD3 expressed on human leukemic T cells Jurkat (ATCC TIB-152). Jurkat T cells were cultured in RPMI supplemented with 10% fetal calf serum. Briefly, cultured cells were harvested, counted and cell viability was evaluated using VI-CELL. Viable cells were then adjusted to $2 \times 10^6$ cells per ml in FACS Stain Buffer (BD Biosciences) containing 0.10% BSA. 100 µl of this cell suspension were further aliquoted per well into a round-bottom 96-well plate. 30 µl of the Alexa488-labelled anti-ROR1/anti-CD3 T cell bispecific antibodies or corresponding IgG control were added to the cell-containing wells to obtain final concentrations of 3 nM to 500 nM or 0.1 pM to 200 nM. Anti-ROR1/anti-CD3 T cell bispecific antibodies and control IgG were used at the same molarity. After incubation for 30 min at 4° C., cells were centrifuged (5 min, 350×g), washed twice with 150 µl/well BSA-containing FACS Stain Buffer (BD Biosciences), then cells were fixed using 100 ul BD Fixation buffer per well (#BD Biosciences, 554655) at 4° C. for 20 min, resuspended in 120 µl FACS buffer and analyzed using BD FACSCANTO II. Binding of the anti-ROR1/anti-CD3 T cell bispecific antibodies to B-CLL cells and T cells were evaluated and the mean fluorescence intensity was determined gated on either ROR1-expressing B-CLL cells or CD3-expressing Jurkat T cells and plotted in histograms or dot plots. FIG. 7 shows the mean fluorescence intensity for anti-ROR1/anti-CD3 T cell bispecific antibodies binding to Jurkat T cells and plotted in function of antibody concentration. EC50 values and maximal binding of anti-ROR1/anti-CD3 TCB1+1 and anti-ROR1/anti-CD3 TCB2+1 antibodies to Jurkat cells were not reached. Interestingly, ROR1/anti-CD3 TCB1+1 antibody binds more efficiently to Jurkat T cells than ROR1/anti-CD3 TCB2+1 antibody does. DP47 isotype control antibody or anti-ROR1 IgG antibody did not bind to Jurkat T cells.

b) Anti-RORI1/anti-CD3 T cell bispecific antibodies were analyzed by flow cytometry for binding to human RORI on ROR 1-expressing myeloma RPMI&226 cells. Briefly, cultured cells were harvested, counted and cell viability was evaluated using VI-CELL. Viable cells were then adjusted to $2 \times 10^6$ cells per ml in BSA-containing FACS Stain Buffer (BD Biosciences). 100 pl of this cell suspension was further aliquoted per well into a round-bottom 96-well plate and incubated with 30 pl of the Alexa488-labelled anti-ROR1/anti-CD3 T cell bispecific antibodies or corresponding IgG control for 30 min at 4° C. All anti-ROR1/anti-CD3 T cell bispecific antibodies (and isotype control) were titrated and analyzed in final concentration range between 0.136-13.6 nM. For samples using non-labelled antibodies, cells were centrifuged (5 min, 350×g), washed with 120 ul/well FACS Stain Buffer (BD Biosciences), resuspended and incubated for an additional 30 min at 4° C. with fluorochrome-conjugated AlexaFluor™ 647-conjugated AffiniPure™ F(ab')2 Fragment goat anti-human IgG Fc Fragment Specific (Jackson Immuno Research Lab; 109-606-008). Cells were then washed twice with Stain Buffer (BD Biosciences), fixed using 100 ul BD Fixation buffer per well (#BD Biosciences, 554655) at 4° C. for 20 min, resuspended in 120 ul FACS buffer and analyzed using BD FACSCANTO II. FIG. 8 shows the mean fluorescence intensity for anti-ROR1/anti-CD3 T cell bispecific antibodies plotted in function of antibody concentration:anti-ROR1/anti-CD3 TCBI1+1 and anti-ROR1/anti-CD3 TCB2+1 antibodies on RPMI8226 cells EC50 values (denoting the antibody concentration required to reach 50% of the maximal binding) for the binding of anti-ROR1/anti-CD3 TCBI1+1 and anti-ROR1/anti-CD3 TCB2+1 antibodies to RPMI8226 cells are summarized in Table 3. Anti-ROR 1/anti-CD3 TCB2+1 antibody bivalent for ROR1 seems to bind to RORI1-positive RPMI8226 myeloma cells slightly better than anti-ROR1/anti-CD3 TCBI1+1 antibody which is monovalent to RORI1, as detected by FACS (FIG. 8). Anti-ROR1/anti-CD3 TCB antibodies were also shown to bind to primary B-CLL cells as detected by flow cytometry using a fluorochrome-conjugated secondary anti-human Fc antibody (FIG. 2A).

TABLE 3

EC50 values for binding of anti-ROR1/anti-CD3
T cell bispecific antibodies to RPMI8226 cells

|  | Anti-ROR1/anti-CD3 TCB1 + 1 antibody | Anti-ROR1/anti-CD3 TCB2 + 1 antibody |
|---|---|---|
| EC50 (nM) | 1.1 | 0.56 |
| EC50 (µg/ml) | 0.16 | 0.11 |

Example 6.1—Binding of Anti-ROR1/Anti-CD3 T Cell Bispecific Antibodies to Ovarian Cancer Cells and T Cells (as Measured by Flow Cytometry)

Anti-ROR 1/anti-CD3 T cell bispecific antibodies generated in Example 5 were analyzed by flow cytometry for their binding to human ovarian cancer cell lines PA-1 and SK-OV-3 and human CD3 expressed on human leukemic T cells Jurkat (ATCC TIB-152). Jurkat T cells were cultured in RPMI1640 medium supplemented with 10% fetal calf serum. Briefly, cultured cells were harvested, counted and cell viability is evaluated using VI-CELL. Viable cells were then adjusted to $2 \times 10^6$ cells per ml in FACS Stain Buffer (BD Biosciences) containing 0.1% BSA. 100 ul of this cell suspension were further aliquoted per well into a round-bottom 96-well plate. 30 pl of the Alexa488-labelled anti-ROR1/anti-CD3 T cell bispecific antibodies or corresponding IgG control were added to the cell-containing wells to obtain final concentrations of 1 nM to 500 nM (Jurkat T cells) or 0.1 nM to 100 nM (human ovarian cancer cells). Anti-ROR1/anti-CD3 T cell bispecific antibodies and control IgG were used at the same molarity. After incubation for 30 min at 4° C., cells are centrifuged (5 min, 350×g), washed twice with 150 pl/well BSA-containing FACS Stain Buffer (BD Biosciences), then cells are fixed using 100 ul BD Fixation buffer per well (#BD Biosciences, 554655) at 4° C. for 20 min, resuspended in 120 pl FACS buffer and analyzed using BD FACSCANTO II. Binding of the anti-ROR1/anti-CD3 T cell bispecific antibodies to human ovarian cancer cells and T cells were evaluated and the median fluorescence intensity was determined gated on either human ovarian cancer cells or CD3-expressing Jurkat T cells and plotted in histograms and dot plots. For samples using non-labelled antibodies, cells were centrifuged (5 min, 350×g), washed with 120 ul/well FACS Stain Buffer (BD Biosciences), resuspended and incubated for an additional 30 min at 4° C. with fluorochrome-conjugated AlexaFluor™ 647-conjugated AffiniPure™ F(ab')2 Fragment goat anti-human IgG Fc Fragment Specific (Jackson Immuno Research Lab; 109-606-008). Cells were then washed twice with Stain Buffer (BD Biosciences), fixed using 100 µl BD Fixation buffer per well (#BD Biosciences, 554655) at 4° C. for 20 min, resuspended in 120 µl FACS buffer and analyzed using BD FACSCANTO II. Median fluorescence intensity for anti-ROR1/anti-CD3 T cell bispecific antibodies in function of antibody concentrations were plotted. EC50 values (denoting the antibody concentration required to reach 50% of the maximal binding) for the binding of anti-ROR1/anti-CD3 antibodies to human ovarian cancer cells were measured using PRISM (GRAPHPAD). As depicted in FIG. 3-3, there was a concentration-dependent binding of ROR1 Mab2 IgG and ROR1 Mab2-TCBcv on SK-OV-3 (A) and on PA-1 human (B) ovarian cancer cell lines as measured by an increase in the median fluorescence intensity signal in function of antibody concentrations. Such positive signals were not observed when the control-TCB binding to CD3 only and not to ROR was tested on both SK-OV-3 and PA-1 ovarian cancer cell lines (A and B; closed circles). As shown in FIG. 3-4, there was a concentration-dependent binding of ROR1 Mab2-TCBcv and control-TCB on Jurkat T cells confirming that both TCB antibodies bind to CD3 on T cells.

Example 7—Internalization of Anti-ROR1/Anti-CD3 T Cell Bispecific Antibodies on EHEB B-CLL Cell Line or Primary PBMC from CLL Patients or RPMI8226 MM Cells (Flow Cytometry)

Anti-ROR1/anti-CD3 T cell bispecific antibodies selected in step (Example 5) above were further tested in the internalization assay. Briefly, cryopreserved human ROR1-expressing primary B-CLL target cells were thawed, harvested with Cell Dissociation Buffer, washed and resuspended in RPMI supplemented with 10% FCS at a concentration of $1 \times 10^6$ ($1 \times 10^6$/mL) of cryopreserved PBMC from untreated CLL patients or $2 \times 10^6$ cells/mL of EHEB B-CLL cell line or $1 \times 10^6$ cells/mL RPMI8226 cells after determination of cell viability using VI-CELL. The cell suspension was transferred in a 15 ml Falcon tube for each tested IgG/TCB and each concentration. 0.5 ml of diluted anti-ROR1 IgG or anti-ROR1/anti-CD3 TCBs conjugated with Alexa488 (diluted to 1 nM in RPMI+10% FCS) were added to the tubes and incubated for 30 min in the cold room on a shaker. After incubation and washing the cells three times with cold PBS to remove unbound antibody, the cells were either left on ice or transferred ($0.1 \times 10^6$ cells) in 96-well FACS plate in pre-warmed medium and incubated at 37° C. for 15 min, 30 min, 1 h, 2 h, and 24 h to facilitate internalization. In addition, cell samples were incubated at 37° C. for 2 h and/or 24 h in the presence of 3 µM phenylarsine oxide (SIGMA-ALDRICH) to inhibit internalization. Subsequently, the cells were washed once with cold PBS and incubated with Alexa647-labeled anti-human Fc secondary antibody ($F(ab)^2$) for 30 min at 4° C. After three final washes with PBS, the cells were centrifuged 4 min at 400×g and resuspended in FACS buffer with or without propidium iodide (1:4000) (Sigma). The mean fluorescence intensity (MFI) of the cells for anti-ROR1 IgG and anti-ROR1/anti-CD3 TCBs was measured using a FACSCANTO II flow cytometer (BD Biosciences) and FLOWJO analytical software.

The term "reduction of mean fluorescence intensity" (ΔMFI) reflecting the internalization of the said anti-ROR1 antibody into ROR1-positive cells" or "MFI reduction" as used herein refers to the percentage of MFI reduction as calculated for each ROR1 antibodies relative to the unspecific human IgG control ($MFI_{background}$) and ROR1 antibodies maintained on ice ($MFI_{max}$) by using the formula $\Delta MFI = 100 - 100 \times [(MFI_{experimental} - MFI_{background})/(MFI_{max} - MFI_{background})]$. $MFI_{experimental}$ is the MFI measured with said ROR1 antibody after 2 h incubation at 37° C. MFI reduction can represent antibody internalization, antibody dissociation or a combination of both. An MFI reduction which is blocked by endocytosis inhibitor phenylarsine oxide indicates antibody internalization while an MFI reduction which is not blocked by phenylarsine oxide reflects antibody dissociation. Internalizing anti-ROR1 antibodies are known in the state of the art (Baskar et al., Clin. Cancer Res., 14(2): 396-404 (2008)).

In some studies, the internalization rate of anti-ROR1/anti-CD3 T cell antibodies was then compared to that of anti-ROR1 bivalent IgG antibody.

For antibody-based therapies such as T cell bispecifics, it is important that the antibody or antibody fragment specific to the tumor target does not internalize, or slowly internalizes, or slightly internalizes for facilitating a stable immune synapse between the tumor cell and the T cell and effective T cell-mediated redirected cytotoxicity and T cell activation.

Figure 4B:
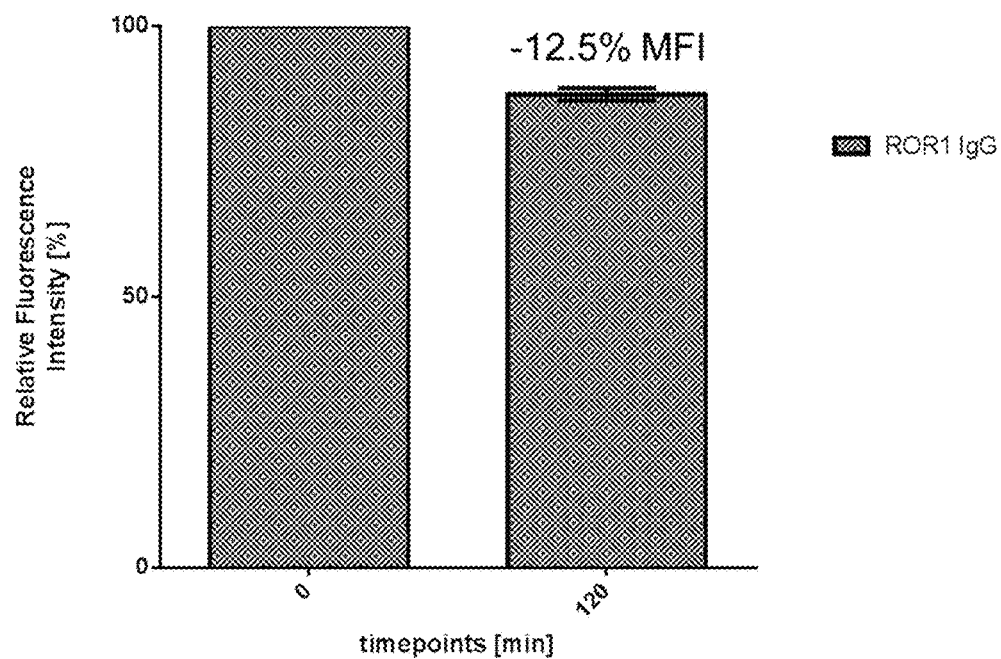
FIG. 4. Internalization rate (%) of (A, B) anti-ROR1 IgG1 antibody at a concentration of 1 nM and (A, C) anti-ROR1/anti-CD3 TCB2+1 antibody on ROR1-positive primary B-CLL cells after 2 h incubation at 37° C., as detected by FACS using secondary labelled anti-human Fc antibody (indirect detection). (A, B) Anti-ROR1 IgG antibody (1 nM) internalized about 12.5% in primary B-CLL cells. (A, C) Anti-ROR1/anti-CD3 TCB2+1 antibody (1 nM) showed an internalization rate of 27.1% in primary B-CLL cells at the same experimental conditions as measured by FACS (indirect detection). Internalization was calculated based on the MFI value at time 0, baseline, and calculated using the previously described formula.
Figure 4C:
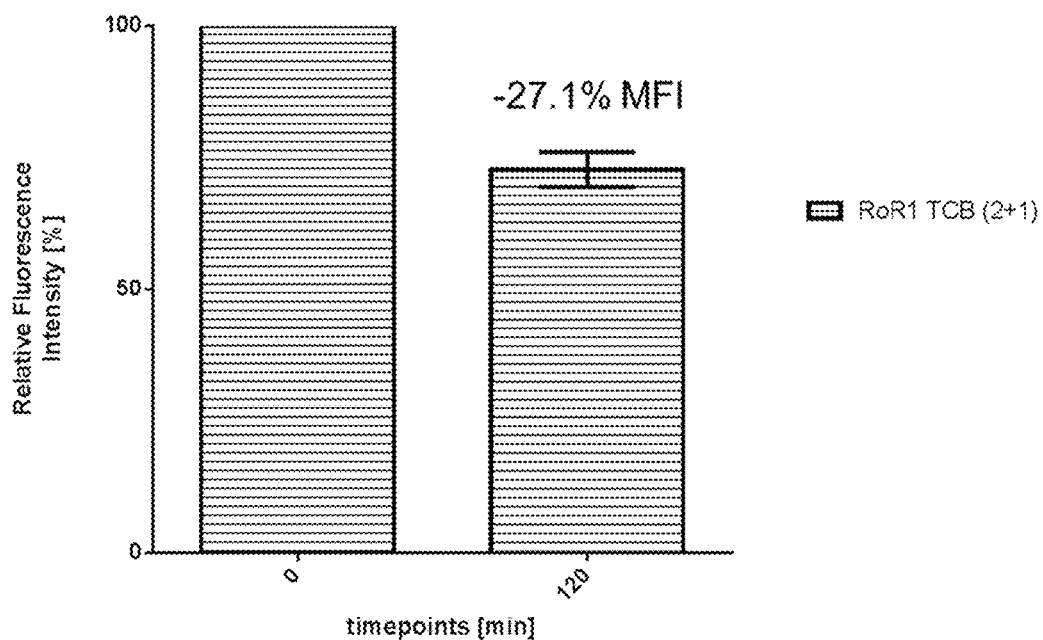

As shown in FIGS. 4A and 4B and summarized in Table 4, anti-ROR1 IgG antibody (1 nM) internalized about 12.5% in primary B-CLL cells after an incubation of 2 hrs at 37° C. while anti-ROR1/anti-CD3 TCB2+1 antibody (1 nM) showed an internalization rate of 27.1% in primary B-CLL cells at the same experimental conditions (FIGS. 4A and 4C) as measured by FACS (indirect detection of secondary fluorochrome-conjugated antibody). Internalization was calculated based on the MFI value at time 0, baseline, and calculated using the previously described formula. The results show that anti-ROR1/anti-CD3 TCB2+1 has an internalization rate of less than 30% in B-CLL cells.

Figure 5:
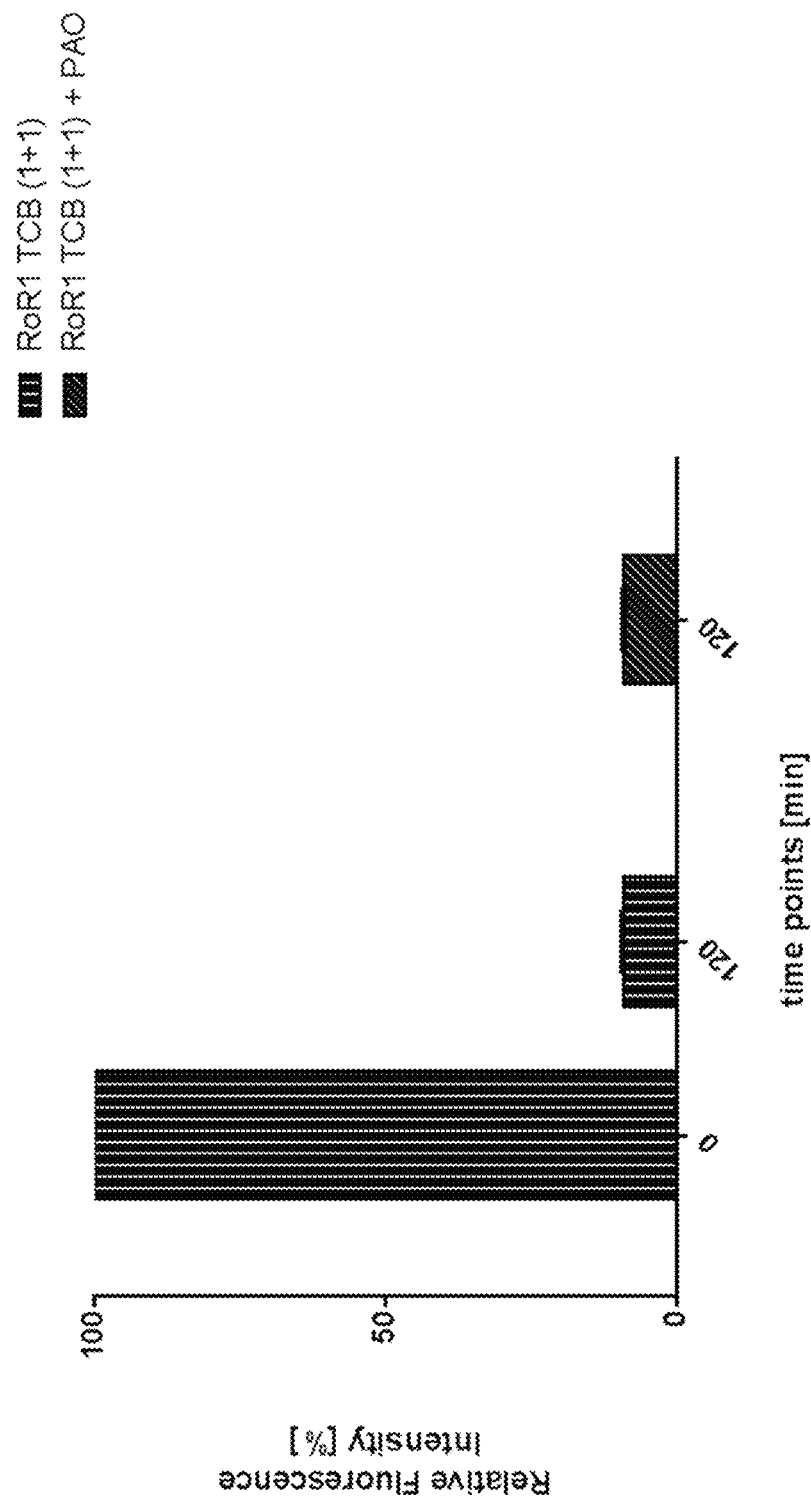
FIG. 5. Internalization rate (%) of anti-ROR1/anti-CD3 TCB1+1 antibody (1 nM) in primary B-CLL cells after an incubation of 2 hrs at 37° C. in the presence or absence of phenylarsine oxide (PAO) as detected by FACS using secondary labelled anti-human Fc antibody (indirect detection). A decrease of 91% in the MFI signal was observed in primary B-CLL cells after an incubation of 2 hrs at 37° C. without PAO. However, when the B-CLL cells were incubated in the presence of PAO (3 μM), 90% decrease in MFI signal was still observed indicating that the loss in MFI signal was not due to internalization of the antibody but rather probably dissociation.

FIG. 5 shows the internalization rate of anti-ROR1/anti-CD3 TCB1+1 antibody (1 nM) in primary B-CLL cells after an incubation of 2 hrs at 37° C. in the presence or absence of phenylarsine oxide (PAO). Because reduction of MFI signal can be due to internalization and/or dissociation of the antibody, it is important to verify if a reduction of MFI signal is caused by internalization or not by using an endocytosis inhibitor to block internalization. This is particularly important for monovalent antibodies that have lower binding avidity to cells than bivalent antibodies. As shown in FIG. 5, there was a decrease of 91% in the MFI signal in primary B-CLL cells after an incubation of 2 hrs at 37° C. without PAO. However, when the B-CLL cells were incubated in the presence of PAO (3 μM), 90% decrease in MFI signal was still observed indicating that the loss in MFI signal was not due to internalization of the antibody but rather probably dissociation (Table 5). Internalization rate could then be calculated to 0%. The results demonstrate that anti-ROR1/anti-CD3 TCB1+1 does not internalize in B-CLL cells, which is a preferred feature for a TCB antibody.

FIG. 6 and Table 6 summarize the internalization rates of TCB2+1 antibodies and anti-ROR1 IgG antibody (1 nM) in RPMI8226 MM cells after an incubation of 2 hrs at 37° C., as measured in two independent experiments. The results demonstrate that anti-ROR1/anti-CD3 TCB2+1 has an internalization rate of less than 15% in RPMI cells.

TABLE 4

Internalization values for anti-ROR1/anti-CD3 2 + 1
T cell bispecific antibody and ROR1 IgG in primary B-CLL cells

|  | Internalization of anti-ROR1 antibody (%) | Internalization of anti-ROM1/anti-CD3 TCB2 + 1 antibody (%) |
| --- | --- | --- |
| Time 0 | 0 (baseline) | 0 (baseline) |
| Time 2 hrs | 12.5 | 27.1 |

TABLE 5

Internalization values for anti-ROR1/anti-CD3 1 + 1
T cell bispecific antibody and ROR1 IgG in primary B-CLL cells

|  | Internalization of anti-ROR1/anti-CD3 TCB1 + 1 antibody (%) |
| --- | --- |
| Time 0 | 0 (baseline) |
| Time 2 hrs | 0 |

TABLE 6

Internalization values for anti-ROR1/anti-CD3 T cell bispecific antibodies and ROR1 IgG in RPMI8226 MM cells

|  | Internalization of anti-ROR1 antibody (%) | Internalization of anti-ROR1/anti-CD3 TCB1 + 1 antibody (%) |
| --- | --- | --- |
| Experiment 1 |  |  |
| Time 0 | 0 (baseline) | 0 (baseline) |
| Time 2 hrs | 0.7 | 8.6 |
| Experiment 2 |  |  |
| Time 0 | 0 (baseline) | 0 (baseline) |
| Time 2 hrs | 0 | 11.8 |

Example 8—Activation of T Cells Upon Engagement of Anti-ROR1/Anti-CD3 T Cell Bispecific Antibodies (Flow Cytometry)

a) Anti-ROR1/anti-CD3 T cell bispecific antibodies generated in Example 5 were also analyzed by flow cytometry for their potential to induce T cell activation by evaluating the surface expression of the early activation marker CD69, or the late activation marker CD25 on CD4$^+$ and CD8$^+$ T cells in the presence or absence of human ROR1-positive cells. Briefly, ROR1-positive cells were harvested with Cell Dissociation buffer, counted and cell viability is verified using VI-CELL. Viable B-CLL cells were adjusted to 0.2× 10$^6$ cells/mL in RPMI supplemented with 10% FCS, 100 μl of this cell suspension per well was pipetted into a round-bottom 96-well plate. 50 μl of the T cell bispecific constructs were added to the ROR1-positive cells-containing wells to obtain a final concentration of 0.01 fM to 100 pM or 0.01 pM to 100 nM. The 96-well plate was set aside and kept at 37° C., 5% CO$_2$ until further manipulations.

PBMC were isolated from fresh blood using density gradient centrifugation using Cell Preparation Tubes with Sodium citrate (VACUTAINER CPT tubes, BD Biosciences). Total human T cells were then isolated using the Pan T Cell Isolation Kit II (MILTENYI BIOTEC), according to the manufacturer's instructions. In some studies, CD8 T cell clones were used as effectors. CD8 T cells specific to NLV (a CMV specific peptide recognized by HLA-A2) were purified from HLA-A2+ healthy donor PBMCs using aCD8 antibodies and tetramers specific to HLA-A2 complexed with NLV peptide and sorted with a cell sorter. The purified cells were expanded on irradiated feeder preparations obtained from healthy donor PBMC and HLA-A2+LCLs (lymphoblastoid cells) pulsed with NLV peptide in media (RPMI1640+10% FBS+1% L-glutamine) with 400IU IL2. The NLV specific CD8 T cell clones were maintained in the same media with 400IU IL2 and regularly reactivated on feeder preparations. Human total T cells or CD8 T cell clones (effectors) were then adjusted to 2×10$^6$ cells per ml in RPMI supplemented with 10% FCS. 50 μl of this cell suspension was added per well in the assay plate containing already ROR1-positive target cells to obtain a final E:T ratio of 3:1 (CD8 T cells as effectors) or 10:1 (PBMC as effectors). To test whether the T cell bispecific constructs were able to activate T cells in the presence of only ROR1-positive tumor target cells, wells containing final concentration(s) in the range of 0.01 fM to 100 pM or 0.01 pM to 100 nM of the respective bispecific molecules with effector cells but without ROR1-positive tumor target cells were also included. After incubation for 6 to 24 h (CD8 T cell clones as effectors) or 24 to 48 hrs (PBMC as effectors) at 37° C., 5% $CO_2$, cells were pelleted down by centrifugation (5 min, 350×g) and washed twice with 150 µl/well of FACS Stain Buffer (BD Biosciences). Surface staining of the effector cells with selected fluorochrome-conjugated antibodies against human CD4, CD8, CD69 or CD25 (BD Biosciences) was performed at 4° C. for 30 min, protected from light, in FACS Stain Buffer (BD Biosciences) according to the manufacturer's protocol. Cells were washed twice with 150 µl/well FACS Stain Buffer then fixed using 100 ul BD Fixation buffer per well (#BD Biosciences, 554655) at 4° C. for 20 min, resuspended in 120 µl FACS buffer and analyzed using BD FACSCANTO II. The expression of CD69 or CD25 activation markers were determined by measuring the mean fluorescence intensity gated on $CD4^+$ and $CD8^+$ T cell populations as represented in histograms or dot plots.

Figure 9C:
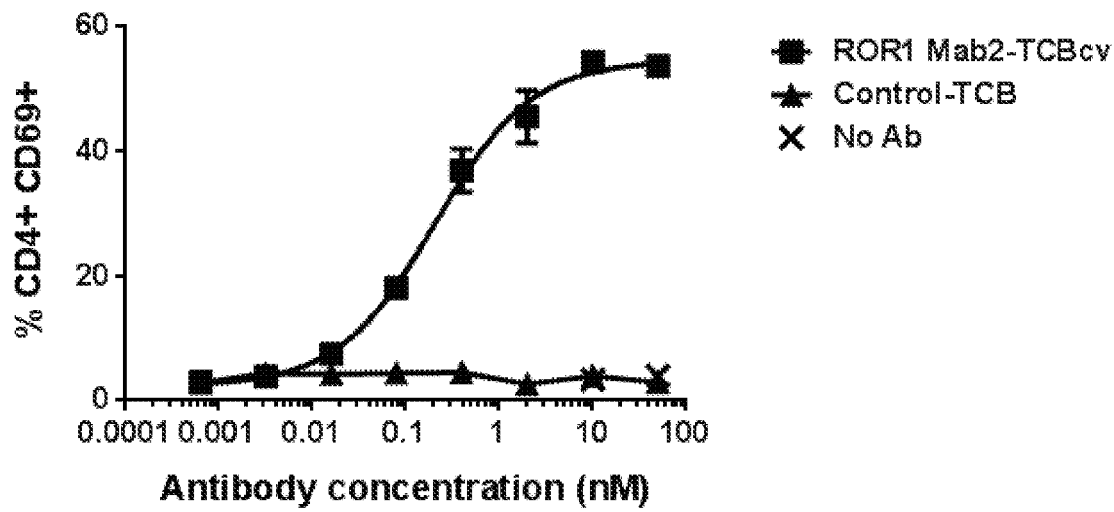
FIGS. 9C-9D. Up-regulation of T-cell activation markers by anti-ROR1/anti-CD3 TCB antibodies in presence of ovarian cancer target cells. The expression of activation markers was determined by measuring the median fluorescence intensity gated on CD4+ and CD8+ T cell populations. ROR1 Mab2-TCBcv (squares) induced a concentration-dependent increase of CD69 early activation marker which was observed on CD4+ T cells (9C) and CD8+ T cells (9D) in presence of ROR1-low expressing SK-OV-3 target cells while control-TCB (triangles) did not induce any T-cell activation. At a clinically relevant concentration of 1 nM of ROR1 Mab2-TCBcv, there was already up to 40% of activated CD4 T cells and 25% of activated CD8 T cells after 48 h of incubation.

FIG. 9A shows the concentration dependent increase in the mean fluorescence intensity of the late activation marker CD25 gated on CD8 T cells. The results indicates that anti-ROR1/anti-CD3 TCB1+1 antibody induced a significant concentration dependent activation of CD8 T cells in the presence of ROR1-positive Rec-1 cells and the maximum signal was reached with 100 pM of antibody. Unspecific activation of CD8 T cells was minimal upon binding of CD3 on T cells but without binding on ROR1-positive target cells obtained by non-binder TCB constructs. Although the activation of CD8 T cells was not as pronounced with anti-ROR1/anti-CD3 TCB2+1 antibody, there was a faint but noticeable increase in CD25 mean fluorescence intensity. However, unspecific activation could not be ruled out.

FIG. 9B shows the concentration dependent upregulation of CD25 on CD8 T cells mediated by anti-ROR1/anti-CD3 TCB1+1 and anti-ROR1/anti-CD3 TCB2+1 antibodies in the presence of ROR1-positive RPMI8226 MM cells. At the highest concentration (100 pM) of TCB antibodies tested there was no unspecific activation of CD8 T cells as shown in comparison to the non-binder TCB constructs.

Example 8.1—Activation of T Cells Upon Engagement of Anti-ROR1/Anti-CD3 T Cell Bispecific Antibodies in the Presence of Ovarian Cancer Cells (Flow Cytometry)

Figure 9D:
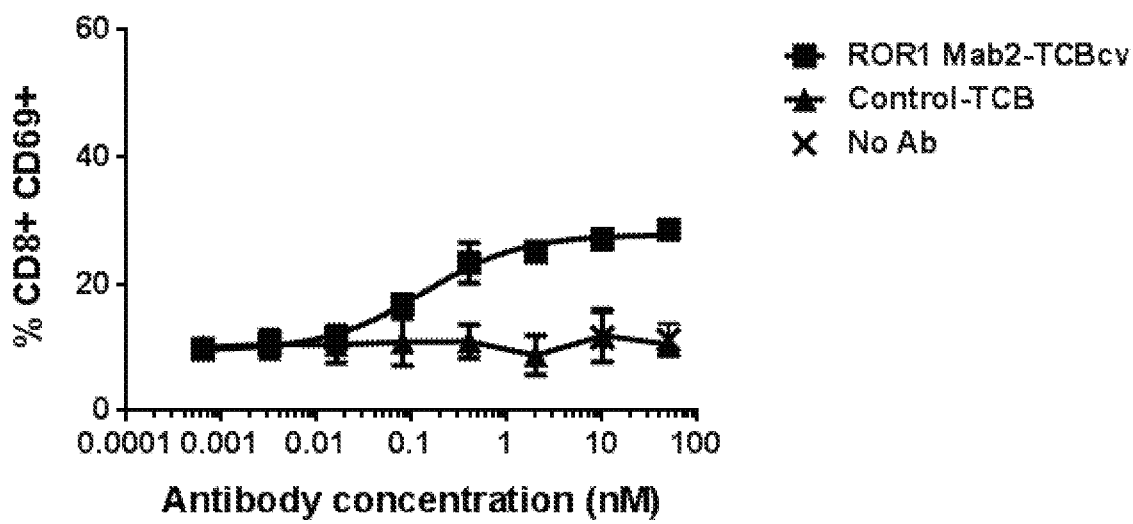

Anti-ROR1/anti-CD3 T cell bispecific antibodies generated in Example 5 were also analyzed by flow cytometry for their potential to induce T-cell activation by evaluating the surface expression of the early activation marker CD69 and/or the late activation marker CD25 on $CD4^+$ and $CD8^+$ T cells in the presence of ROR1-positive human ovarian cancer cell lines PA-1 and/or SK-OV-3. Briefly, human ovarian cancer target cells were harvested with Trypsin/EDTA, washed, and plated at density of 25,000 cells/well using flat-bottom 96-well plates. Cells were left to adhere overnight. Peripheral blood mononuclear cells (PBMCs) were prepared by HISTOPAQUE™ density centrifugation of enriched lymphocyte preparations (buffy coats) obtained from healthy human donors. Fresh blood was diluted with sterile PBS and layered over HISTOPAQUE™ gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (VI-CELL) and stored in respective culture medium according to the cell line supplier (see Example 2.1) at 370 C, 5% $CO_2$ in a cell incubator until further use (no longer than 24 h). To examine T-cell activation induced by anti-ROR1/anti-CD3 T cell bispecific antibodies, human ovarian cancer cells were exposed to the bispecific antibody at the indicated concentrations (range of 0.1 pM to 200 nM in triplicates). PBMCs were then added to the human ovarian cancer target cells at final effector to target (E:T) ratio of 10:1. T-cell activation was assessed after 24 to 48 h of incubation at 37° C., 5% $CO_2$. After the incubation period, cells were collected from the wells, pelleted down by centrifugation (5 min, 350×g) and washed twice with 150 µl/well of FACS Stain Buffer (BD Biosciences). Surface staining of the effector cells with selected fluorochrome-conjugated antibodies against human CD4 (mouse IgGl, K; clone RPA-T4), CD8 (mouse IgGl, K; clone HIT8a; BD #555635), CD69 (mouse IgGl; clone L78; BD #340560) and CD25 (mouse IgGl, K; clone M-A251; BD #555434) was performed at 4° C. for 30 min, protected from light, in FACS Stain Buffer (BD Biosciences) according to the manufacturer's protocol. Cells were washed twice with 150 µl/well FACS Stain Buffer then fixed using 100 ul BD Fixation buffer per well (#BD Biosciences, 554655) at 4° C. for 20 min, resuspended in 120 µl FACS buffer and analyzed using BD FACSCANTO II. The expression of CD69 or CD25 activation markers were determined by measuring the median fluorescence intensity gated on $CD4^+$ and $CD8^+$ T cell populations as represented in histograms or dot plots. As shown in FIG. 9.1, ROR1 Mab2-TCBcv (squares) induced a concentration-dependent increase of CD69 early activation marker which was observed on CD4+ T cells (A) and CD8+ T cells (B) in presence of ROR1-low expressing SK-OV-3 target cells while control-TCB (triangles) did not induce any T-cell activation. At a clinically relevant concentration of 1 nM of ROR1 Mab2-TCBcv, there was already up to 40% of activated CD4 T cells and 25% of activated CD8 T cells after 48 h of incubation.

Example 9—Redirected T Cell Cytotoxicity of Multiple Myeloma Cells Upon Cross-Linking of Anti-ROR1/Anti-CD3 T Cell Bispecific Antibodies to CD3 on T Cells and ROR1 on Multiple Myeloma Cells (LDH Release Assay)

Anti-ROR1/anti-CD3 T cell bispecific antibodies generated in Example 5 were also analyzed for their potential to induce T cell-mediated apoptosis in ROR1-expressing multiple myeloma cells upon crosslinking of the construct via binding of the antigen binding moieties to ROR1 on cells. Briefly, human ROR1-expressing RPMI-8226 multiple myeloma target cells (available from American Type Culture Collection; ATCC CCL-155) were harvested with Cell Dissociation Buffer, washed and resuspended in RPMI supplemented with 10% FCS. Approximately, 30,000 cells per well were plated in a round-bottom 96-well plate and the respective dilution of the construct was added for a desired final concentration (in triplicates); final concentrations ranging from 0.01 fM to 100 pM or 0.2 nM to 30 nM. For an appropriate comparison, all T cell bispecific constructs and controls were adjusted to the same molarity. Human total T cells or CD8 T cell clones (effectors) were added into the wells to obtain a final E:T ratio of 3:1. When human PBMC were used as effector cells, a final E:T ratio of 10:1 was used. PHA-L (Sigma) was used as positive control for human T cell activation at a concentration of 1 µg/ml. Negative control groups were represented by effector or target cells only. For normalization, maximal lysis of the RPMI-8226 multiple myeloma target cells (=100%) was determined by incubation of the target cells with a final concentration of 1% TRITON X-100, inducing cell death. Minimal lysis (=0%) was represented by target cells co-incubated with effector cells only, i.e. without any T cell bispecific antibody. After 6 to 24 hrs incubation (CD8 T cell clones as effectors) or 24 to 48 hrs incubation (PBMC as effectors) at 37° C., 5% $CO_2$, LDH release from the apoptotic/necrotic ROR1-positive target cells into the supernatant was then measured with the LDH detection kit (Roche Applied Science), following the manufacturer's instructions. The percentage of LDH release was plotted against the concentrations of anti-ROR1/anti-CD3 T cell bispecific antibodies in concentration-response curves. The $IC_{50}$ values were measured using PRISM software (GRAPHPAD) and determined as the T cell bispecific antibody concentration that results in 50% of maximum LDH release.

Figure 10A:
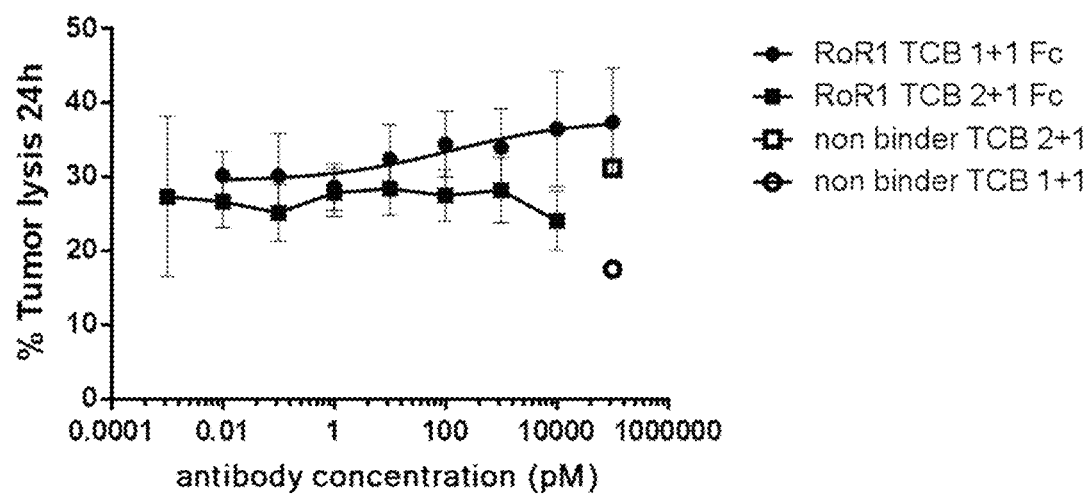
FIG. 10. Redirected T cell killing of ROR1-positive RPMI8226 MM target cells by CD8 T cells activated by anti-ROR1/anti-CD3 TCB antibodies. Specific cytotoxicity of target cells (tumor lysis) induced by anti-ROR1/anti-CD3 TCB antibodies was measured by LDH release. (A) Experiment 1 (14 h time point): 30% of tumor lysis was already observed with the lowest concentration tested of 0.01 pM anti-ROR1/anti-CD3 TCB1+1 antibody and up to 37.5% tumor lysis was reached with 30 nM of anti-ROR1/anti-CD3 TCB antibodies in experimental conditions with E:T ratio of 3:1 i.e. 3 CD8 T cells for 1 RPMI 8226 target cell. The 37.5% tumor lysis observed at 30 nM as detected by LDH release could not have been attributed only to unspecific killing of target cells as there was only 17% unspecific target cell lysis with 30 nM of non-binder TCB1+1 (i.e. binds to effector cells but not to target cells). For anti-ROR1/anti-CD3 TCB2+1 antibody, a maximum target cell lysis of 30% was already observed at the lowest concentration tested of 0.2 fM and there was no concentration dependent response with increasing concentrations for up to 10 nM. 30 nM non-binding TCB2+1 had close to 30% tumor lysis. (B) Experiment 2 (20 h time point): 30-40% target cell lysis was observed with anti-ROR1/anti-CD3 TCB1+1 and TCB2+1 antibodies at a concentration of 100 pM while non-binder TCB controls did not induce any tumor lysis at the same concentration.
Figure 10B:
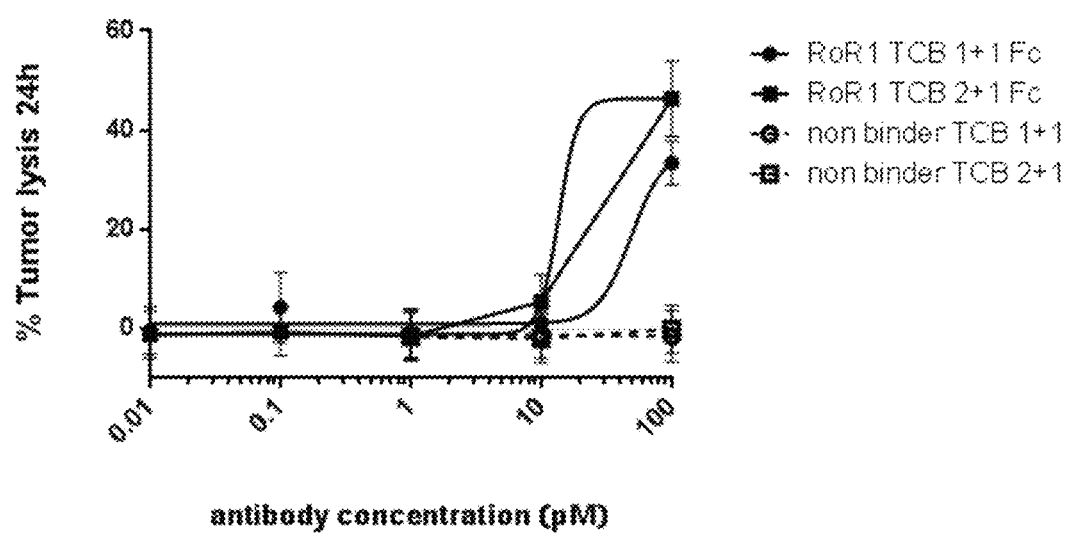

FIG. 10 shows the redirected T cell killing of ROR1-positive RPMI8226 MM target cells by CD8 T cells activated by anti-ROR1/anti-CD3 TCB antibodies. Specific cytotoxicity of target cells (tumor lysis) induced by anti-ROR1/anti-CD3 TCB antibodies was measured by LDH release. (A) Experiment 1 (14 h time point): A very slight concentration dependent increase of tumor lysis response was observed with anti-ROR1/anti-CD3 TCB1+1 antibody. 30% of tumor lysis was already observed with the lowest concentration tested of 0.01 pM anti-ROR1/anti-CD3 TCB1+1 antibody and up to 37.5% tumor lysis was reached with 30 nM of anti-ROR1/anti-CD3 TCB antibodies in experimental conditions reflecting clinically relevant E:T ratio of 3:1 i.e. 3 CD8 T cells for 1 RPMI 8226 target cell. EC50 could not be calculated. The 37.5% tumor lysis observed at 30 nM as detected by LDH release could not have been attributed only to unspecific killing of target cells as there was only 17% unspecific target cell lysis with 30 nM of non-binder TCB1+1 (i.e. binds to effector cells but not to target cells). For anti-ROR1/anti-CD3 TCB2+1 antibody, a maximum target cell lysis of 30% was already observed at the lowest concentration tested of 0.2 fM and there was no concentration dependent response with increasing concentrations for up to 10 nM. However, cell lysis with the non-binder TCB 2+1 in a concentration of 30 nM was already close to 30%. (B) Experiment 2 (20 h time point): The study was repeated in ROR1-positive RPMI8226 and measurement of LDH release was assessed after 20 h incubation. 30-40% target cell lysis was observed with anti-ROR1/anti-CD3 TCB1+1 and TCB2+1 antibodies at a concentration of 100 pM while non-binder TCB controls at 100 pM did not induce any tumor lysis. The results corroborate with an increase in T cell activation as measured by upregulation of CD25 marker on the CD8 T cells (FIG. 9B).

Figure 11A:
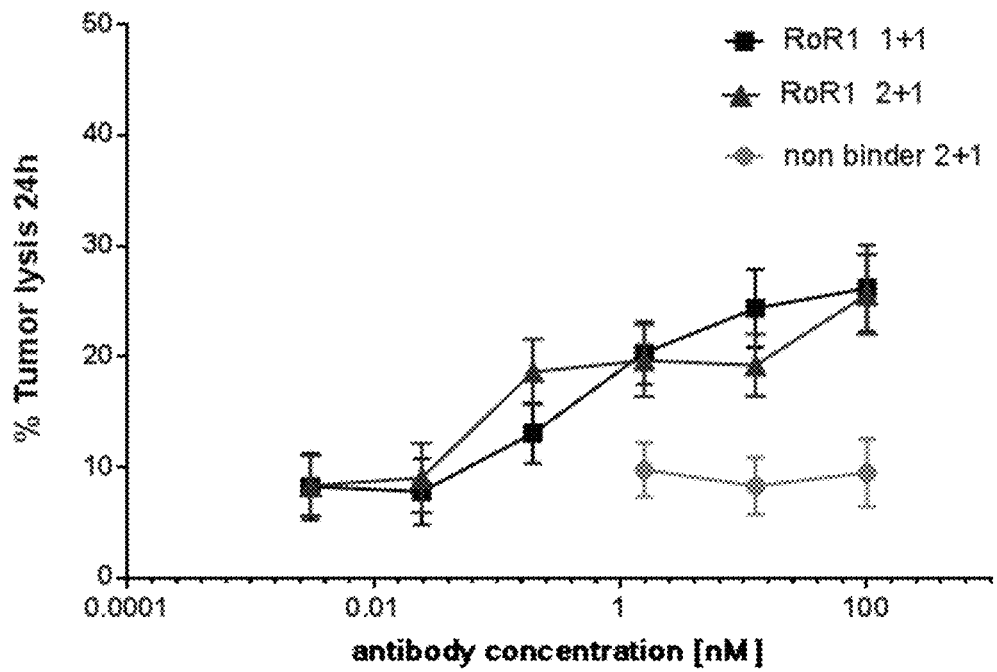
FIG. 11. Redirected T cell killing of ROR1-positive RPMI8226 MM target cells by T cells from PBMCs activated by anti-ROR1/anti-CD3 TCB antibodies at different effector cells to tumor cells (E:T) ratios. Specific cytotoxicity of target cells (tumor lysis) induced by anti-ROR1/anti-CD3 TCB antibodies was measured by LDH release. (A) E:T ratio=10 PBMCs:1 RPMI8226 MM cell (24 h time point): there was a concentration dependent response with increasing concentrations for up to 100 nM. A maximum mean of 25% of tumor lysis was observed with 100 nM concentration anti-ROR1/anti-CD3 TCB1+1 and anti-ROR1/anti-CD3 TCB2+1 antibodies in experimental conditions with E:T ratio of 10:1 i.e. 10 PBMCs for 1 RPMI8226 target cell. The 25% tumor lysis observed at 100 nM as detected by LDH release could not have been attributed only to unspecific killing of target cells as there was only 9% unspecific target cell lysis with 100 nM of non-binder TCB2+1 (i.e. binds to effector cells but not to target cells). (B) E:T ratio=25 PBMCs:1 RPMI8226 MM cell (24 h time point): there was a concentration dependent tumor lysis with increasing concentrations of anti-ROR1/anti-CD3 TCB1+1 for up to 2 nM. A maximum mean of 30% of tumor lysis was observed already with 2 nM concentration of anti-ROR1/anti-CD3 TCB1+1, but tumor lysis seemed to reach a plateau since 100 nM concentration was not associated with a higher response.
Figure 11B:
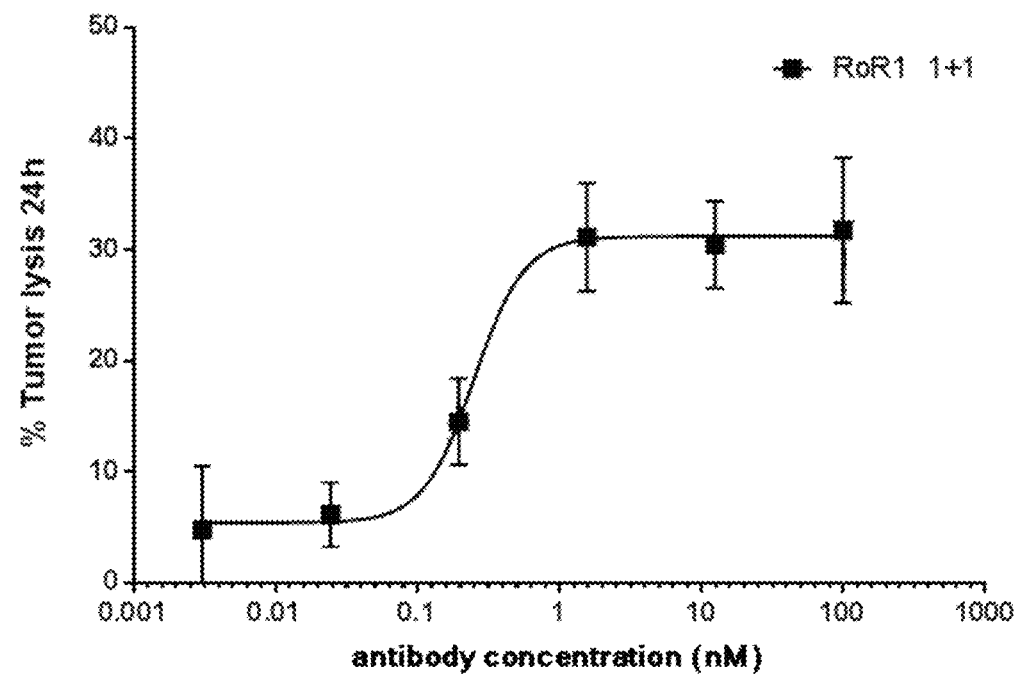
Figure 12A:
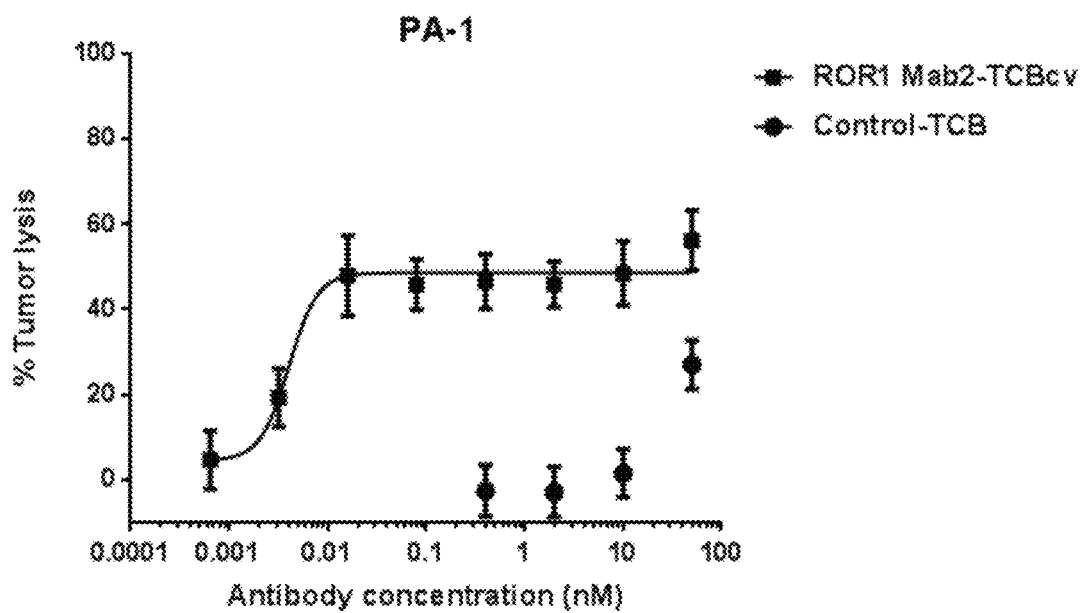
FIG. 12. Redirected T cell killing of ROR1-positive ovarian cancer target cells with different level of surface ROR1: high expressing PA-1 (A), medium expressing COLO-704 (B) and OVCAR-5 (C), and low expressing SK-OV-3 (D). Effector cells to tumor cells (E:T) ratios of 10 PBMCs:1 target cell. Specific cytotoxicity of target cells (tumor lysis) induced by anti-ROR1/anti-CD3 TCB antibodies was measured by LDH release (48 h culture). There was a concentration dependent response with increasing concentrations from 0.5 pM to 50 nM. ROR1 Mab2-TCBcv (squares) induced a concentration-dependent increase in tumor cell lysis of ROR1 high-expressing PA-1 ovarian cancer cells (A), ROR1 medium-expressing COLO-704 (B) and OVCAR-5 (C) ovarian cancer cells and ROR1 low-expressing SK-OV-3 ovarian cancer cells (D). In contrast, control-TCB (A, B, C; circles) which only binds to CD3 did not induce tumor cell lysis at clinically relevant concentrations (i.e. up to 10 nM). Representative experiments shown (n=1 to 5).
Figure 12B:
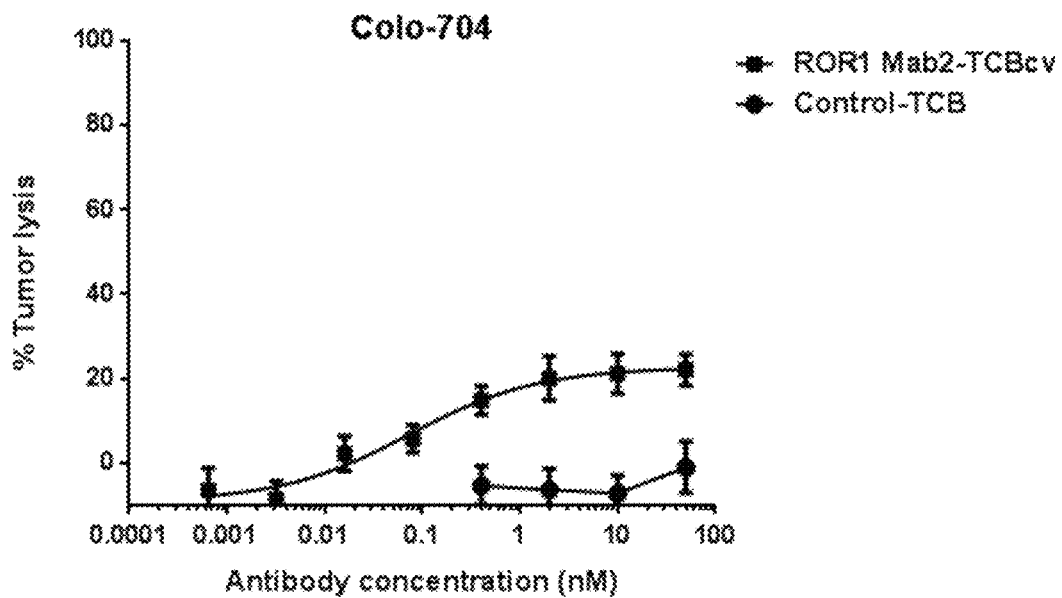
Figure 12C:
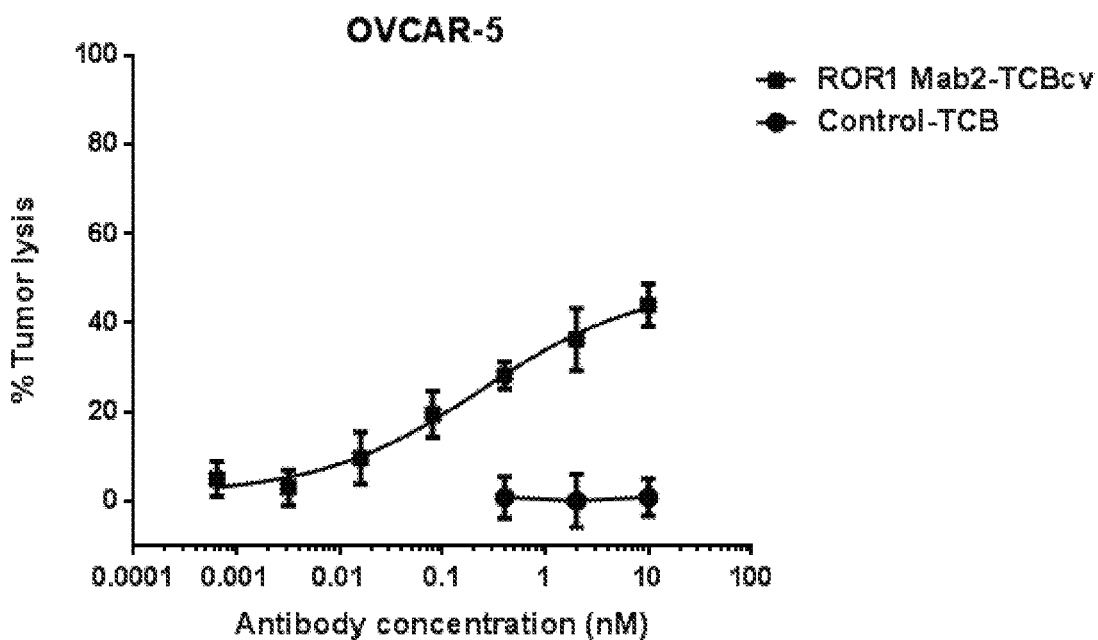
Figure 12D:
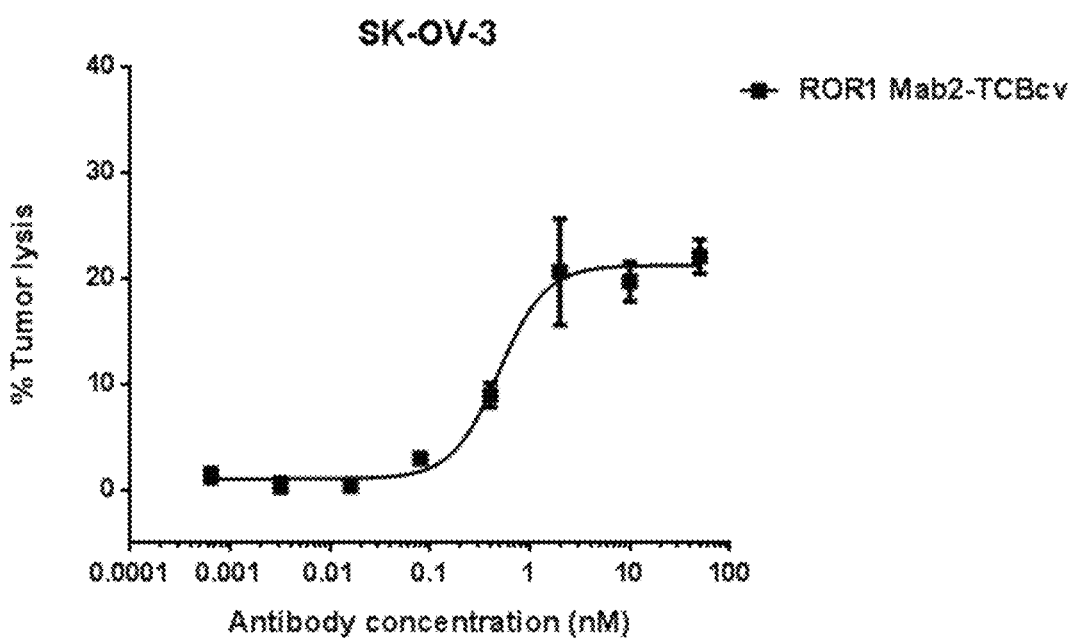

FIG. 11 shows the redirected T cell killing of ROR1-positive RPMI8226 MM target cells by T cells from PBMCs activated by anti-ROR1/anti-CD3 TCB antibodies at different effector cells to tumor cells (E:T) ratios. Specific cytotoxicity of target cells (tumor lysis) induced by anti-ROR1/anti-CD3 TCB antibodies was measured by LDH release. (A) E:T ratio=10 PBMCs:1 RPMI8226 MM cell (24 h time point): there was a concentration dependent response with increasing concentrations for up to 100 nM. A maximum mean of 25% of tumor lysis was observed with 100 nM concentration anti-ROR1/anti-CD3 TCB1+1 and anti-ROR1/anti-CD3 TCB2+1 antibodies in experimental conditions with E:T ratio of 10:1 i.e. 10 PBMCs for 1 RPMI8226 target cell. The 25% tumor lysis observed at 100 nM as detected by LDH release could not have been attributed only to unspecific killing of target cells as there was only 9% unspecific target cell lysis with 100 nM of non-binder TCB2+1 (i.e. binds to effector cells but not to target cells). (B) E:T ratio=25 PBMCs:1 RPMI8226 MM cell (24 h time point): there was a concentration dependent tumor lysis with increasing concentrations of anti-ROR1/anti-CD3 TCB1+1 for up to 2 nM. A maximum mean of 30% of tumor lysis was observed already with 2 nM concentration of anti-ROR1/anti-CD3 TCB1+1, but tumor lysis seemed to reach a plateau since 100 nM concentration was not associated with a higher response.

The overall in vitro results with ROR1-positive blood cancer cells (CLL, MM, and MCL) clearly show that anti-ROR1/anti-CD3 TCB1+1 and anti-ROR1/anti-CD3 TCB2+1 molecules act like T cell bispecific antibodies as they 1) bind to ROR1-positive target cells; 2) bind to CD3-positive T cells; 3) mediate T cell activation upon simultaneous binding to target cells and T cells; and 4) induce redirected T cell cytotoxicity of ROR1-positive target cells in a concentration-dependent manner which corroborate with the upregulation of CD25 on T cells.

Example 10—Cell Lysis of Human Ovarian Cancer Cells (LDH Release Assay)

Anti-ROR1/anti-CD3 T cell bispecific antibodies generated in Example 5 were analyzed for induction of T cell-mediated cytotoxicity in human ovarian cancer cells. Human ovarian cancer cell lines PA-1, COLO-704, SK-OV-3 and OVCAR-5. Briefly, human ovarian cancer target cells were harvested with Trypsin/EDTA, washed, and plated at density of 25,000 cells/well using flat-bottom 96-well plates. Cells were left to adhere overnight. Peripheral blood mononuclear cells (PBMCs) were prepared by HISTOPAQUE™ density centrifugation of enriched lymphocyte preparations (buffy coats) obtained from healthy human donors. Fresh blood was diluted with sterile PBS and layered over HISTOPAQUE™ gradient (Sigma, #H8889). After centrifugation (450×g, 30 minutes, room temperature), the plasma above the PBMC-containing interphase was discarded and PBMCs transferred in a new falcon tube subsequently filled with 50 ml of PBS. The mixture was centrifuged (400×g, 10 minutes, room temperature), the supernatant discarded and the PBMC pellet washed twice with sterile PBS (centrifugation steps 350×g, 10 minutes). The resulting PBMC population was counted automatically (VI-CELL) and stored in respective culture medium as suggested by the cell line supplier (see Example 2.1) at 370 C, 5% $CO_2$ in a cell incubator until further use (no longer than 24 h). For the killing assay, the TCB antibody was added at the indicated concentrations (range of 0.1 pM to 200 nM in triplicates). PBMCs were added to the human ovarian cancer target cells at final effector to target (E:T) ratio of 10:1. Target cell killing was assessed after 24 h to 48 h of incubation at 37° C., 5% $CO_2$ by quantification of LDH released into cell supernatants by apoptotic/necrotic cells (LDH detection kit, Roche Applied Science, #11 644 793 001) following the manufacturer's instructions. Maximal lysis of the target cells (=100%) was achieved by incubation of target cells with 1% TRITON X-100. Minimal lysis (=0%) refers to target cells co-incubated with effector cells without bispecific construct. The percentage of LDH release was plotted against the concentrations of anti-ROR1/anti-CD3 T cell bispecific antibodies in concentration-response curves. The $EC_{50}$ values were measured using PRISM software (GRAPHPAD) and determined as the T cell bispecific antibody concentration that results in 50% of maximum LDH release. As shown in FIG. 12, ROR1 Mab2-TCBcv (squares) induced a concentration-dependent increase in tumor cell lysis of ROR1 high-expressing PA-1 ovarian cancer cells (A), ROR1 medium-expressing COLO-704 (B) and OVCAR-5 (C) ovarian cancer cells and ROR1 low-expressing SK-OV-3 ovarian cancer cells (D). In contrast, control-TCB (A, B, C; circles) which only binds to CD3 did not induce tumor cell lysis at clinically relevant concentrations (i.e. up to 10 nM). Representative experiments shown.

TABLE 9

EC50 values for cell lysis of ovarian cancer cell lines
by anti-ROR1/anti-CD3 T cell bispecific antibodies

| | ROR1 Mab2-TCBcv | |
|---|---|---|
| Ovarian cancer cell lines | Mean EC50 (pM) | Mean EC50 (ng/mL) |
| PA-1 (n = 2) | 14.6 (4.7-24.5) | 2.9 (0.9-4.9) |
| COLO-704 (n = 1) | 73.3 | 14.3 |
| OVCAR-5 (n = 1) | 53.4 | 10.7 |
| SKOV-3 (n = 5) | 707 (456-1003) | 141.4 (91.2-200.6) |

The invention claimed is:

1. A bispecific antibody which specifically binds human CD3ε comprising SEQ ID NO: 63 and an extracellular domain of human ROR1 comprising SEQ ID NO: 1, said bispecific antibody comprising:
   (a) heavy chain polypeptides of SEQ ID NO: 37 and SEQ ID NO: 38, and light chain polypeptides of SEQ ID NO: 39 and SEQ ID NO: 40; or
   (b) heavy chain polypeptides of SEQ ID NO: 37 and SEQ ID NO: 38, and light chain polypeptides of SEQ ID NO: 39 and SEQ ID NO: 41.

2. A method for preparing a bispecific antibody according to claim 1 comprising the steps of:
   a) transforming a host cell with vectors comprising nucleic acid molecules encoding the bispecific antibody of claim 1,
   b) culturing the host cell under conditions that allow synthesis of said bispecific antibody; and
   c) recovering said bispecific antibody from said culture.

3. A host cell comprising vectors comprising nucleic acid molecules encoding the bispecific antibody of claim 1.

4. A pharmaceutical composition comprising the bispecific antibody of claim 1 and a pharmaceutically acceptable excipient.

5. A nucleic acid molecule or nucleic acid molecules encoding the bispecific antibody of claim 1.

6. A vector or vectors comprising the nucleic acid molecule or nucleic acid molecules of claim 5.

* * * * *

SEQUENCE LISTING

<160> NUMBER OF SEQ ID NOS: 63

<210> SEQ ID NO 1
<211> LENGTH: 937
<212> TYPE: PRT
<213> ORGANISM: Homo sapiens

<400> SEQUENCE: 1

```
Met His Arg Pro Arg Arg Arg Gly Thr Arg Pro Pro Leu Leu Ala Leu
1               5                  10                  15

Leu Ala Ala Leu Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285
```

-continued

```
Glu Ser Pro Glu Ala Ala Asn Cys Ile Arg Ile Gly Ile Pro Met Ala
    290                 295                 300
Asp Pro Ile Asn Lys Asn His Lys Cys Tyr Asn Ser Thr Gly Val Asp
305                 310                 315                 320
Tyr Arg Gly Thr Val Ser Val Thr Lys Ser Gly Arg Gln Cys Gln Pro
                325                 330                 335
Trp Asn Ser Gln Tyr Pro His Thr His Thr Phe Thr Ala Leu Arg Phe
            340                 345                 350
Pro Glu Leu Asn Gly Gly His Ser Tyr Cys Arg Asn Pro Gly Asn Gln
        355                 360                 365
Lys Glu Ala Pro Trp Cys Phe Thr Leu Asp Glu Asn Phe Lys Ser Asp
    370                 375                 380
Leu Cys Asp Ile Pro Ala Cys Asp Ser Lys Asp Ser Lys Glu Lys Asn
385                 390                 395                 400
Lys Met Glu Ile Leu Tyr Ile Leu Val Pro Ser Val Ala Ile Pro Leu
                405                 410                 415
Ala Ile Ala Leu Leu Phe Phe Ile Cys Val Cys Arg Asn Asn Gln
            420                 425                 430
Lys Ser Ser Ala Pro Val Gln Arg Gln Pro Lys His Val Arg Gly
        435                 440                 445
Gln Asn Val Glu Met Ser Met Leu Asn Ala Tyr Lys Pro Lys Ser Lys
    450                 455                 460
Ala Lys Glu Leu Pro Leu Ser Ala Val Arg Phe Met Glu Glu Leu Gly
465                 470                 475                 480
Glu Cys Ala Phe Gly Lys Ile Tyr Lys Gly His Leu Tyr Leu Pro Gly
                485                 490                 495
Met Asp His Ala Gln Leu Val Ala Ile Lys Thr Leu Lys Asp Tyr Asn
            500                 505                 510
Asn Pro Gln Gln Trp Thr Glu Phe Gln Gln Glu Ala Ser Leu Met Ala
        515                 520                 525
Glu Leu His His Pro Asn Ile Val Cys Leu Leu Gly Ala Val Thr Gln
    530                 535                 540
Glu Gln Pro Val Cys Met Leu Phe Glu Tyr Ile Asn Gln Gly Asp Leu
545                 550                 555                 560
His Glu Phe Leu Ile Met Arg Ser Pro His Ser Asp Val Gly Cys Ser
                565                 570                 575
Ser Asp Glu Asp Gly Thr Val Lys Ser Ser Leu Asp His Gly Asp Phe
            580                 585                 590
Leu His Ile Ala Ile Gln Ile Ala Ala Gly Met Glu Tyr Leu Ser Ser
        595                 600                 605
His Phe Phe Val His Lys Asp Leu Ala Ala Arg Asn Ile Leu Ile Gly
    610                 615                 620
Glu Gln Leu His Val Lys Ile Ser Asp Leu Gly Leu Ser Arg Glu Ile
625                 630                 635                 640
Tyr Ser Ala Asp Tyr Tyr Arg Val Gln Ser Lys Ser Leu Leu Pro Ile
                645                 650                 655
Arg Trp Met Pro Pro Glu Ala Ile Met Tyr Gly Lys Phe Ser Ser Asp
            660                 665                 670
Ser Asp Ile Trp Ser Phe Gly Val Val Leu Trp Glu Ile Phe Ser Phe
        675                 680                 685
Gly Leu Gln Pro Tyr Tyr Gly Phe Ser Asn Gln Glu Val Ile Glu Met
    690                 695                 700
```

```
Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
            740                 745                 750

Ser Ser His Thr Ser Ser Thr Thr Pro Ser Gly Gly Asn Ala Thr Thr
        755                 760                 765

Gln Thr Thr Ser Leu Ser Ala Ser Pro Val Ser Asn Leu Ser Asn Pro
    770                 775                 780

Arg Tyr Pro Asn Tyr Met Phe Pro Ser Gln Gly Ile Thr Pro Gln Gly
785                 790                 795                 800

Gln Ile Ala Gly Phe Ile Gly Pro Pro Ile Pro Gln Asn Gln Arg Phe
                805                 810                 815

Ile Pro Ile Asn Gly Tyr Pro Ile Pro Pro Gly Tyr Ala Ala Phe Pro
            820                 825                 830

Ala Ala His Tyr Gln Pro Thr Gly Pro Pro Arg Val Ile Gln His Cys
        835                 840                 845

Pro Pro Pro Lys Ser Arg Ser Pro Ser Ser Ala Ser Gly Ser Thr Ser
    850                 855                 860

Thr Gly His Val Thr Ser Leu Pro Ser Ser Gly Ser Asn Gln Glu Ala
865                 870                 875                 880

Asn Ile Pro Leu Leu Pro His Met Ser Ile Pro Asn His Pro Gly Gly
                885                 890                 895

Met Gly Ile Thr Val Phe Gly Asn Lys Ser Gln Lys Pro Tyr Lys Ile
            900                 905                 910

Asp Ser Lys Gln Ala Ser Leu Leu Gly Asp Ala Asn Ile His Gly His
        915                 920                 925

Thr Glu Ser Met Ile Ser Ala Glu Leu
    930                 935

<210> SEQ ID NO 2
<211> LENGTH: 112
<212> TYPE: PRT
<213> ORGANISM: Oryctolagus cuniculus

<400> SEQUENCE: 2

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
            100                 105                 110

<210> SEQ ID NO 3
<211> LENGTH: 12
<212> TYPE: PRT
<213> ORGANISM: Oryctolagus cuniculus
```

<400> SEQUENCE: 3

Thr Leu Ser Ser Ala His Lys Thr Asp Thr Ile Asp
1               5                   10

<210> SEQ ID NO 4
<211> LENGTH: 7
<212> TYPE: PRT
<213> ORGANISM: Oryctolagus cuniculus

<400> SEQUENCE: 4

Gly Ser Tyr Thr Lys Arg Pro
1               5

<210> SEQ ID NO 5
<211> LENGTH: 9
<212> TYPE: PRT
<213> ORGANISM: Oryctolagus cuniculus

<400> SEQUENCE: 5

Gly Ala Asp Tyr Ile Gly Gly Tyr Val
1               5

<210> SEQ ID NO 6
<211> LENGTH: 121
<212> TYPE: PRT
<213> ORGANISM: Oryctolagus cuniculus

<400> SEQUENCE: 6

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser
        115                 120

<210> SEQ ID NO 7
<211> LENGTH: 5
<212> TYPE: PRT
<213> ORGANISM: Oryctolagus cuniculus

<400> SEQUENCE: 7

Ala Tyr Tyr Met Ser
1               5

<210> SEQ ID NO 8
<211> LENGTH: 17
<212> TYPE: PRT
<213> ORGANISM: Oryctolagus cuniculus

<400> SEQUENCE: 8

```
Thr Ile Tyr Pro Ser Ser Gly Lys Thr Tyr Tyr Ala Thr Trp Val Asn
1               5                   10                  15

Gly

<210> SEQ ID NO 9
<211> LENGTH: 12
<212> TYPE: PRT
<213> ORGANISM: Oryctolagus cuniculus

<400> SEQUENCE: 9

Asp Ser Tyr Ala Asp Asp Gly Ala Leu Phe Asn Ile
1               5                   10

<210> SEQ ID NO 10
<211> LENGTH: 125
<212> TYPE: PRT
<213> ORGANISM: Mus musculus

<400> SEQUENCE: 10

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser
        115                 120                 125

<210> SEQ ID NO 11
<211> LENGTH: 109
<212> TYPE: PRT
<213> ORGANISM: Mus musculus

<400> SEQUENCE: 11

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
                20                  25                  30

Tyr Tyr Pro Asn Trp Val Gln Lys Pro Gly Gln Ala Pro Arg Gly
            35                  40                  45

Leu Ile Gly Gly Thr Lys Phe Leu Ala Pro Gly Thr Pro Ala Arg Phe
        50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu
            100                 105

<210> SEQ ID NO 12
```

-continued

```
<211> LENGTH: 10
<212> TYPE: PRT
<213> ORGANISM: Mus musculus

<400> SEQUENCE: 12

Gly Phe Thr Phe Asn Lys Tyr Ala Met Asn
1               5                   10

<210> SEQ ID NO 13
<211> LENGTH: 19
<212> TYPE: PRT
<213> ORGANISM: Mus musculus

<400> SEQUENCE: 13

Arg Ile Arg Ser Lys Tyr Asn Asn Tyr Ala Thr Tyr Tyr Ala Asp Ser
1               5                   10                  15

Val Lys Asp

<210> SEQ ID NO 14
<211> LENGTH: 14
<212> TYPE: PRT
<213> ORGANISM: Mus musculus

<400> SEQUENCE: 14

His Gly Asn Phe Gly Asn Ser Tyr Ile Ser Tyr Trp Ala Tyr
1               5                   10

<210> SEQ ID NO 15
<211> LENGTH: 14
<212> TYPE: PRT
<213> ORGANISM: Mus musculus

<400> SEQUENCE: 15

Gly Ser Ser Thr Gly Ala Val Thr Ser Gly Tyr Tyr Pro Asn
1               5                   10

<210> SEQ ID NO 16
<211> LENGTH: 7
<212> TYPE: PRT
<213> ORGANISM: Mus musculus

<400> SEQUENCE: 16

Gly Thr Lys Phe Leu Ala Pro
1               5

<210> SEQ ID NO 17
<211> LENGTH: 9
<212> TYPE: PRT
<213> ORGANISM: Mus musculus

<400> SEQUENCE: 17

Ala Leu Trp Tyr Ser Asn Arg Trp Val
1               5

<210> SEQ ID NO 18
<211> LENGTH: 15
<212> TYPE: PRT
<213> ORGANISM: Homo sapiens

<400> SEQUENCE: 18

Trp Asn Ile Ser Ser Glu Leu Asn Lys Asp Ser Tyr Leu Thr Leu
1               5                   10                  15

<210> SEQ ID NO 19
```

```
<211> LENGTH: 10
<212> TYPE: PRT
<213> ORGANISM: Artificial sequence
<220> FEATURE:
<223> OTHER INFORMATION: artificial linker sequence

<400> SEQUENCE: 19

Gly Gly Gly Gly Ser Gly Gly Gly Gly Ser
1               5                   10

<210> SEQ ID NO 20
<211> LENGTH: 14
<212> TYPE: PRT
<213> ORGANISM: Homo sapiens
<220> FEATURE:
<223> OTHER INFORMATION: Intracellular fragment of ROR1

<400> SEQUENCE: 20

Lys Ser Gln Lys Pro Tyr Lys Ile Asp Ser Lys Gln Ala Ser
1               5                   10

<210> SEQ ID NO 21
<211> LENGTH: 125
<212> TYPE: PRT
<213> ORGANISM: Mus musculus

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 22
<211> LENGTH: 109
<212> TYPE: PRT
<213> ORGANISM: Mus musculus

<400> SEQUENCE: 22

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80
```

```
Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 23
<211> LENGTH: 5
<212> TYPE: PRT
<213> ORGANISM: Mus musculus

<400> SEQUENCE: 23

Thr Tyr Ala Met Asn
1               5

<210> SEQ ID NO 24
<211> LENGTH: 19
<212> TYPE: PRT
<213> ORGANISM: Mus musculus

<400> SEQUENCE: 24

Arg Ile Arg Ser Lys Tyr Asn Asn Tyr Ala Thr Tyr Tyr Ala Asp Ser
1               5                   10                  15

Val Lys Gly

<210> SEQ ID NO 25
<211> LENGTH: 14
<212> TYPE: PRT
<213> ORGANISM: Mus musculus

<400> SEQUENCE: 25

His Gly Asn Phe Gly Asn Ser Tyr Val Ser Trp Phe Ala Tyr
1               5                   10

<210> SEQ ID NO 26
<211> LENGTH: 14
<212> TYPE: PRT
<213> ORGANISM: Mus musculus

<400> SEQUENCE: 26

Gly Ser Ser Thr Gly Ala Val Thr Thr Ser Asn Tyr Ala Asn
1               5                   10

<210> SEQ ID NO 27
<211> LENGTH: 7
<212> TYPE: PRT
<213> ORGANISM: Mus musculus

<400> SEQUENCE: 27

Gly Thr Asn Lys Arg Ala Pro
1               5

<210> SEQ ID NO 28
<211> LENGTH: 9
<212> TYPE: PRT
<213> ORGANISM: Mus musculus

<400> SEQUENCE: 28

Ala Leu Trp Tyr Ser Asn Leu Trp Val
1               5

<210> SEQ ID NO 29
<211> LENGTH: 451
<212> TYPE: PRT
<213> ORGANISM: Mus musculus
```

<400> SEQUENCE: 29

```
Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
```

405                 410                 415
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 30
<211> LENGTH: 236
<212> TYPE: PRT
<213> ORGANISM: Mus musculus

<400> SEQUENCE: 30

Met Gly Trp Ser Cys Ile Ile Leu Phe Leu Val Ala Thr Ala Thr Gly
1               5                   10                  15

Val His Ser Glu Leu Val Leu Thr Gln Ser Pro Ser Val Ser Ala Ala
            20                  25                  30

Leu Gly Ser Pro Ala Lys Ile Thr Cys Thr Leu Ser Ser Ala His Lys
        35                  40                  45

Thr Asp Thr Ile Asp Trp Tyr Gln Gln Leu Gln Gly Glu Ala Pro Arg
    50                  55                  60

Tyr Leu Met Gln Val Gln Ser Asp Gly Ser Tyr Thr Lys Arg Pro Gly
65                  70                  75                  80

Val Pro Asp Arg Phe Ser Gly Ser Ser Ser Gly Ala Asp Arg Tyr Leu
                85                  90                  95

Ile Ile Pro Ser Val Gln Ala Asp Asp Glu Ala Asp Tyr Tyr Cys Gly
            100                 105                 110

Ala Asp Tyr Ile Gly Gly Tyr Val Phe Gly Gly Gly Thr Gln Leu Thr
        115                 120                 125

Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 31
<211> LENGTH: 694
<212> TYPE: PRT
<213> ORGANISM: Mus musculus

<400> SEQUENCE: 31

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile

```
            35                  40                  45
Ala Thr Ile Tyr Pro Ser Ser Gly Lys Thr Tyr Tyr Ala Thr Trp Val
 50                  55                  60

Asn Gly Arg Phe Thr Ile Ser Ser Asp Asn Ala Gln Asn Thr Val Asp
 65                  70                  75                  80

Leu Gln Met Asn Ser Leu Thr Ala Ala Asp Arg Ala Thr Tyr Phe Cys
                 85                  90                  95

Ala Arg Asp Ser Tyr Ala Asp Asp Gly Ala Leu Phe Asn Ile Trp Gly
                100                 105                 110

Pro Gly Thr Leu Val Thr Ile Ser Ser Ala Ser Thr Lys Gly Pro Ser
                115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Lys Val Glu Pro Lys Ser Cys
210                 215                 220

Asp Gly Gly Gly Gly Ser Gly Gly Gly Gly Ser Glu Val Gln Leu Leu
225                 230                 235                 240

Glu Ser Gly Gly Gly Leu Val Gln Pro Gly Gly Ser Leu Arg Leu Ser
                245                 250                 255

Cys Ala Ala Ser Gly Phe Thr Phe Ser Thr Tyr Ala Met Asn Trp Val
                260                 265                 270

Arg Gln Ala Pro Gly Lys Gly Leu Glu Trp Val Ser Arg Ile Arg Ser
                275                 280                 285

Lys Tyr Asn Asn Tyr Ala Thr Tyr Tyr Ala Asp Ser Val Lys Gly Arg
                290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
                340                 345                 350

Gly Thr Leu Val Thr Val Ser Ser Ala Ser Val Ala Ala Pro Ser Val
                355                 360                 365

Phe Ile Phe Pro Pro Ser Asp Glu Gln Leu Lys Ser Gly Thr Ala Ser
                370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
                420                 425                 430

Thr Leu Ser Lys Ala Asp Tyr Glu Lys His Lys Val Tyr Ala Cys Glu
                435                 440                 445

Val Thr His Gln Gly Leu Ser Ser Pro Val Thr Lys Ser Phe Asn Arg
                450                 455                 460
```

```
Gly Glu Cys Asp Lys Thr His Thr Cys Pro Pro Cys Pro Ala Pro Glu
465                 470                 475                 480

Ala Ala Gly Gly Pro Ser Val Phe Leu Phe Pro Pro Lys Pro Lys Asp
                485                 490                 495

Thr Leu Met Ile Ser Arg Thr Pro Glu Val Thr Cys Val Val Val Asp
            500                 505                 510

Val Ser His Glu Asp Pro Glu Val Lys Phe Asn Trp Tyr Val Asp Gly
        515                 520                 525

Val Glu Val His Asn Ala Lys Thr Lys Pro Arg Glu Glu Gln Tyr Asn
    530                 535                 540

Ser Thr Tyr Arg Val Val Ser Val Leu Thr Val Leu His Gln Asp Trp
545                 550                 555                 560

Leu Asn Gly Lys Glu Tyr Lys Cys Lys Val Ser Asn Lys Ala Leu Gly
                565                 570                 575

Ala Pro Ile Glu Lys Thr Ile Ser Lys Ala Lys Gly Gln Pro Arg Glu
            580                 585                 590

Pro Gln Val Tyr Thr Leu Pro Pro Cys Arg Asp Glu Leu Thr Lys Asn
        595                 600                 605

Gln Val Ser Leu Trp Cys Leu Val Lys Gly Phe Tyr Pro Ser Asp Ile
    610                 615                 620

Ala Val Glu Trp Glu Ser Asn Gly Gln Pro Glu Asn Asn Tyr Lys Thr
625                 630                 635                 640

Thr Pro Pro Val Leu Asp Ser Asp Gly Ser Phe Phe Leu Tyr Ser Lys
                645                 650                 655

Leu Thr Val Asp Lys Ser Arg Trp Gln Gln Gly Asn Val Phe Ser Cys
            660                 665                 670

Ser Val Met His Glu Ala Leu His Asn His Tyr Thr Gln Lys Ser Leu
        675                 680                 685

Ser Leu Ser Pro Gly Lys
    690

<210> SEQ ID NO 32
<211> LENGTH: 451
<212> TYPE: PRT
<213> ORGANISM: Mus musculus

<400> SEQUENCE: 32

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Ala Ser Thr Lys Gly Pro Ser
        115                 120                 125

Val Phe Pro Leu Ala Pro Ser Ser Lys Ser Thr Ser Gly Gly Thr Ala
```

```
                130             135             140
    Ala Leu Gly Cys Leu Val Lys Asp Tyr Phe Pro Glu Pro Val Thr Val
    145                 150                 155                 160

Ser Trp Asn Ser Gly Ala Leu Thr Ser Gly Val His Thr Phe Pro Ala
                    165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                    195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
    225                 230                 235                 240

Gly Pro Ser Val Phe Leu Phe Pro Pro Lys Pro Lys Asp Thr Leu Met
                    245                 250                 255

Ile Ser Arg Thr Pro Glu Val Thr Cys Val Val Val Asp Val Ser His
                    260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
    305                 310                 315                 320

Lys Glu Tyr Lys Cys Lys Val Ser Asn Lys Ala Leu Gly Ala Pro Ile
                    325                 330                 335

Glu Lys Thr Ile Ser Lys Ala Lys Gly Gln Pro Arg Glu Pro Gln Val
                340                 345                 350

Cys Thr Leu Pro Pro Ser Arg Asp Glu Leu Thr Lys Asn Gln Val Ser
                    355                 360                 365

Leu Ser Cys Ala Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
    385                 390                 395                 400

Val Leu Asp Ser Asp Gly Ser Phe Phe Leu Val Ser Lys Leu Thr Val
                    405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                    435                 440                 445

Pro Gly Lys
    450

<210> SEQ ID NO 33
<211> LENGTH: 214
<212> TYPE: PRT
<213> ORGANISM: Mus musculus

<400> SEQUENCE: 33

Gln Ala Val Val Thr Gln Glu Pro Ser Leu Thr Val Ser Pro Gly Gly
    1               5                   10                  15

Thr Val Thr Leu Thr Cys Gly Ser Ser Thr Gly Ala Val Thr Thr Ser
                    20                  25                  30

Asn Tyr Ala Asn Trp Val Gln Glu Lys Pro Gly Gln Ala Phe Arg Gly
                35                  40                  45
```

Leu Ile Gly Gly Thr Asn Lys Arg Ala Pro Gly Thr Pro Ala Arg Phe
        50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Ser Ser Ala
            100                 105                 110

Ser Thr Lys Gly Pro Ser Val Phe Pro Leu Ala Pro Ser Ser Lys Ser
        115                 120                 125

Thr Ser Gly Gly Thr Ala Ala Leu Gly Cys Leu Val Lys Asp Tyr Phe
    130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Lys
        195                 200                 205

Val Glu Pro Lys Ser Cys
210

<210> SEQ ID NO 34
<211> LENGTH: 467
<212> TYPE: PRT
<213> ORGANISM: Mus musculus

<400> SEQUENCE: 34

Gln Glu Gln Leu Val Glu Ser Gly Gly Arg Leu Val Thr Pro Gly Gly
  1               5                  10                  15

Ser Leu Thr Leu Ser Cys Lys Ala Ser Gly Phe Asp Phe Ser Ala Tyr
             20                  25                  30

Tyr Met Ser Trp Val Arg Gln Ala Pro Gly Lys Gly Leu Glu Trp Ile
         35                  40                  45

Ala Thr Ile Tyr Pro Ser Ser Gly Lys Thr Tyr Tyr Ala Thr Trp Val
     50                  55                  60

Asn Gly Arg Phe Thr Ile Ser Ser Asp Asn Ala Gln Asn Thr Val Asp
 65                  70                  75                  80

Leu Gln Met Asn Ser Leu Thr Ala Ala Asp Arg Ala Thr Tyr Phe Cys
                 85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

-continued

Lys Pro Ser Asn Thr Lys Val Asp Lys Val Glu Pro Lys Ser Cys
210                 215                 220

Asp Gly Gly Gly Gly Ser Gly Gly Gly Ser Glu Val Gln Leu Leu
225                 230                 235                 240

Glu Ser Gly Gly Gly Leu Val Gln Pro Gly Gly Ser Leu Arg Leu Ser
            245                 250                 255

Cys Ala Ala Ser Gly Phe Thr Phe Ser Thr Tyr Ala Met Asn Trp Val
            260                 265                 270

Arg Gln Ala Pro Gly Lys Gly Leu Glu Trp Val Ser Arg Ile Arg Ser
            275                 280                 285

Lys Tyr Asn Asn Tyr Ala Thr Tyr Tyr Ala Asp Ser Val Lys Gly Arg
290                 295                 300

Phe Thr Ile Ser Arg Asp Asp Ser Lys Asn Thr Leu Tyr Leu Gln Met
305                 310                 315                 320

Asn Ser Leu Arg Ala Glu Asp Thr Ala Val Tyr Tyr Cys Val Arg His
            325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ala Ser Val Ala Ala Pro Ser Val
            355                 360                 365

Phe Ile Phe Pro Pro Ser Asp Glu Gln Leu Lys Ser Gly Thr Ala Ser
370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
            405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
            435                 440                 445

Val Thr His Gln Gly Leu Ser Ser Pro Val Thr Lys Ser Phe Asn Arg
450                 455                 460

Gly Glu Cys
465

<210> SEQ ID NO 35
<211> LENGTH: 702
<212> TYPE: PRT
<213> ORGANISM: Mus musculus

<400> SEQUENCE: 35

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
            35                  40                  45

Ala Thr Ile Tyr Pro Ser Ser Gly Lys Thr Tyr Tyr Ala Thr Trp Val
50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
            85                  90                  95

Ala Arg Asp Ser Tyr Ala Asp Asp Gly Ala Leu Phe Asn Ile Trp Gly

```
            100                 105                 110
Pro Gly Thr Leu Val Thr Ile Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                    165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Val Glu Pro Lys Ser Cys
            210                 215                 220

Asp Gly Gly Gly Ser Gly Gly Gly Ser Gln Glu Gln Leu Val
225                 230                 235                 240

Glu Ser Gly Gly Arg Leu Val Thr Pro Gly Gly Ser Leu Thr Leu Ser
                    245                 250                 255

Cys Lys Ala Ser Gly Phe Asp Phe Ser Ala Tyr Tyr Met Ser Trp Val
                    260                 265                 270

Arg Gln Ala Pro Gly Lys Gly Leu Glu Trp Ile Ala Thr Ile Tyr Pro
            275                 280                 285

Ser Ser Gly Lys Thr Tyr Tyr Ala Thr Trp Val Asn Gly Arg Phe Thr
            290                 295                 300

Ile Ser Ser Asp Asn Ala Gln Asn Thr Val Asp Leu Gln Met Asn Ser
305                 310                 315                 320

Leu Thr Ala Ala Asp Arg Ala Thr Tyr Phe Cys Ala Arg Asp Ser Tyr
                    325                 330                 335

Ala Asp Asp Gly Ala Leu Phe Asn Ile Trp Gly Pro Gly Thr Leu Val
                    340                 345                 350

Thr Ile Ser Ser Ala Ser Thr Lys Gly Pro Ser Val Phe Pro Leu Ala
            355                 360                 365

Pro Ser Ser Lys Ser Thr Ser Gly Gly Thr Ala Ala Leu Gly Cys Leu
            370                 375                 380

Val Lys Asp Tyr Phe Pro Glu Pro Val Thr Val Ser Trp Asn Ser Gly
385                 390                 395                 400

Ala Leu Thr Ser Gly Val His Thr Phe Pro Ala Val Leu Gln Ser Ser
                    405                 410                 415

Gly Leu Tyr Ser Leu Ser Ser Val Val Thr Val Pro Ser Ser Ser Leu
            420                 425                 430

Gly Thr Gln Thr Tyr Ile Cys Asn Val Asn His Lys Pro Ser Asn Thr
            435                 440                 445

Lys Val Asp Lys Val Glu Pro Lys Ser Cys Asp Gly Gly Gly
            450                 455                 460

Ser Gly Gly Gly Gly Ser Glu Val Gln Leu Leu Glu Ser Gly Gly Gly
465                 470                 475                 480

Leu Val Gln Pro Gly Gly Ser Leu Arg Leu Ser Cys Ala Ala Ser Gly
                    485                 490                 495

Phe Thr Phe Ser Thr Tyr Ala Met Asn Trp Val Arg Gln Ala Pro Gly
                    500                 505                 510

Lys Gly Leu Glu Trp Val Ser Arg Ile Arg Ser Lys Tyr Asn Asn Tyr
            515                 520                 525
```

```
Ala Thr Tyr Tyr Ala Asp Ser Val Lys Gly Arg Phe Thr Ile Ser Arg
            530                 535                 540

Asp Asp Ser Lys Asn Thr Leu Tyr Leu Gln Met Asn Ser Leu Arg Ala
545                 550                 555                 560

Glu Asp Thr Ala Val Tyr Tyr Cys Val Arg His Gly Asn Phe Gly Asn
                565                 570                 575

Ser Tyr Val Ser Trp Phe Ala Tyr Trp Gly Gln Gly Thr Leu Val Thr
            580                 585                 590

Val Ser Ser Ala Ser Val Ala Ala Pro Ser Val Phe Ile Phe Pro Pro
        595                 600                 605

Ser Asp Glu Gln Leu Lys Ser Gly Thr Ala Ser Val Val Cys Leu Leu
610                 615                 620

Asn Asn Phe Tyr Pro Arg Glu Ala Lys Val Gln Trp Lys Val Asp Asn
625                 630                 635                 640

Ala Leu Gln Ser Gly Asn Ser Gln Glu Ser Val Thr Glu Gln Asp Ser
                645                 650                 655

Lys Asp Ser Thr Tyr Ser Leu Ser Ser Thr Leu Thr Leu Ser Lys Ala
            660                 665                 670

Asp Tyr Glu Lys His Lys Val Tyr Ala Cys Glu Val Thr His Gln Gly
        675                 680                 685

Leu Ser Ser Pro Val Thr Lys Ser Phe Asn Arg Gly Glu Cys
690                 695                 700

<210> SEQ ID NO 36
<211> LENGTH: 246
<212> TYPE: PRT
<213> ORGANISM: Homo sapiens

<400> SEQUENCE: 36

Met Gly Trp Ser Cys Ile Ile Leu Phe Leu Val Ala Thr Ala Thr Gly
1               5                   10                  15

Val His Ser Asp Lys Thr His Thr Cys Pro Pro Cys Pro Ala Pro Glu
            20                  25                  30

Ala Ala Gly Gly Pro Ser Val Phe Leu Phe Pro Pro Lys Pro Lys Asp
        35                  40                  45

Thr Leu Met Ile Ser Arg Thr Pro Glu Val Thr Cys Val Val Val Asp
50                  55                  60

Val Ser His Glu Asp Pro Glu Val Lys Phe Asn Trp Tyr Val Asp Gly
65                  70                  75                  80

Val Glu Val His Asn Ala Lys Thr Lys Pro Arg Glu Glu Gln Tyr Asn
                85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Gly
        115                 120                 125

Ala Pro Ile Glu Lys Thr Ile Ser Lys Ala Lys Gly Gln Pro Arg Glu
130                 135                 140

Pro Gln Val Cys Thr Leu Pro Pro Ser Arg Asp Glu Leu Thr Lys Asn
145                 150                 155                 160

Gln Val Ser Leu Ser Cys Ala Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Val Ser Lys
```

```
                    195                 200                 205
Leu Thr Val Asp Lys Ser Arg Trp Gln Gln Gly Asn Val Phe Ser Cys
            210                 215                 220

Ser Val Met His Glu Ala Leu His Asn His Tyr Thr Gln Lys Ser Leu
225                 230                 235                 240

Ser Leu Ser Pro Gly Lys
                245

<210> SEQ ID NO 37
<211> LENGTH: 676
<212> TYPE: PRT
<213> ORGANISM: Artificial sequence
<220> FEATURE:
<223> OTHER INFORMATION: ROR1 R12 VH_CH1cv x CD3 VL_CH1 Fc knob LALA PG

<400> SEQUENCE: 37

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Gly Gly Gly Gly Ser Gly Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Gly Ser Ser Thr Gly Ala Val Thr Thr Ser Asn Tyr Ala Asn Trp
            260                 265                 270

Val Gln Glu Lys Pro Gly Gln Ala Phe Arg Gly Leu Ile Gly Gly Thr
        275                 280                 285

Asn Lys Arg Ala Pro Gly Thr Pro Ala Arg Phe Ser Gly Ser Leu Leu
    290                 295                 300

Gly Gly Lys Ala Ala Leu Thr Leu Ser Gly Ala Gln Pro Glu Asp Glu
```

```
            305                 310                 315                 320
Ala Glu Tyr Tyr Cys Ala Leu Trp Tyr Ser Asn Leu Trp Val Phe Gly
                325                 330                 335

Gly Gly Thr Lys Leu Thr Val Leu Ser Ser Ala Ser Thr Lys Gly Pro
                340                 345                 350

Ser Val Phe Pro Leu Ala Pro Ser Ser Lys Ser Thr Ser Gly Gly Thr
                355                 360                 365

Ala Ala Leu Gly Cys Leu Val Lys Asp Tyr Phe Pro Glu Pro Val Thr
                370                 375                 380

Val Ser Trp Asn Ser Gly Ala Leu Thr Ser Gly Val His Thr Phe Pro
385                 390                 395                 400

Ala Val Leu Gln Ser Ser Gly Leu Tyr Ser Leu Ser Ser Val Val Thr
                405                 410                 415

Val Pro Ser Ser Ser Leu Gly Thr Gln Thr Tyr Ile Cys Asn Val Asn
                420                 425                 430

His Lys Pro Ser Asn Thr Lys Val Asp Lys Lys Val Glu Pro Lys Ser
                435                 440                 445

Cys Asp Lys Thr His Thr Cys Pro Pro Cys Pro Ala Pro Glu Ala Ala
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
                500                 505                 510

Val His Asn Ala Lys Thr Lys Pro Arg Glu Glu Gln Tyr Asn Ser Thr
                515                 520                 525

Tyr Arg Val Val Ser Val Leu Thr Val Leu His Gln Asp Trp Leu Asn
                530                 535                 540

Gly Lys Glu Tyr Lys Cys Lys Val Ser Asn Lys Ala Leu Gly Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Cys Arg Asp Glu Leu Thr Lys Asn Gln Val
                580                 585                 590

Ser Leu Trp Cys Leu Val Lys Gly Phe Tyr Pro Ser Asp Ile Ala Val
                595                 600                 605

Glu Trp Glu Ser Asn Gly Gln Pro Glu Asn Asn Tyr Lys Thr Thr Pro
610                 615                 620

Pro Val Leu Asp Ser Asp Gly Ser Phe Phe Leu Tyr Ser Lys Leu Thr
625                 630                 635                 640

Val Asp Lys Ser Arg Trp Gln Gln Gly Asn Val Phe Ser Cys Ser Val
                645                 650                 655

Met His Glu Ala Leu His Asn His Tyr Thr Gln Lys Ser Leu Ser Leu
                660                 665                 670

Ser Pro Gly Lys
            675

<210> SEQ ID NO 38
<211> LENGTH: 451
<212> TYPE: PRT
<213> ORGANISM: Artificial sequence
<220> FEATURE:
<223> OTHER INFORMATION: ROR1 R12 VH_CH1cv HC hole LALA PG
```

<400> SEQUENCE: 38

```
Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Glu Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Glu Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Gly Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415
```

-continued

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 39
<211> LENGTH: 232
<212> TYPE: PRT
<213> ORGANISM: Artificial sequence
<220> FEATURE:
<223> OTHER INFORMATION: CD3 VH_CL

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
    130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 40
<211> LENGTH: 217
<212> TYPE: PRT
<213> ORGANISM: Artificial sequence
<220> FEATURE:
<223> OTHER INFORMATION: ROR1 R12 cv hum IgG1 lambda LC

<400> SEQUENCE: 40

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr

```
                 20                  25                  30

Ile Asp Trp Tyr Gln Gln Leu Gln Gly Glu Ala Pro Arg Tyr Leu Met
            35                  40                  45

Gln Val Gln Ser Asp Gly Ser Tyr Thr Lys Arg Pro Gly Val Pro Asp
        50                  55                  60

Arg Phe Ser Gly Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Leu Gly
            100                 105                 110

Gln Pro Lys Ala Ala Pro Ser Val Thr Leu Phe Pro Pro Ser Ser Lys
        115                 120                 125

Lys Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 41
<211> LENGTH: 218
<212> TYPE: PRT
<213> ORGANISM: Artificial sequence
<220> FEATURE:
<223> OTHER INFORMATION: ROR1 R12 cv hum IgG1 kappa LC

<400> SEQUENCE: 41

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Arg
            100                 105                 110

Thr Val Ala Ala Pro Ser Val Phe Ile Phe Pro Pro Ser Asp Arg Lys
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
```

```
              165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 42
<211> LENGTH: 119
<212> TYPE: PRT
<213> ORGANISM: Artificial sequence
<220> FEATURE:
<223> OTHER INFORMATION: Mab3 ROR1 VH

<400> SEQUENCE: 42

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115

<210> SEQ ID NO 43
<211> LENGTH: 117
<212> TYPE: PRT
<213> ORGANISM: Artificial sequence
<220> FEATURE:
<223> OTHER INFORMATION: Mab3 ROR1 VH

<400> SEQUENCE: 43

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser His Trp
            20                  25                  30

Met Ser Trp Val Arg Gln Ala Pro Gly Lys Gly Leu Glu Trp Ile Gly
        35                  40                  45

Ile Ile Ala Ala Ser Gly Ser Thr Tyr Tyr Ala Asn Trp Ala Lys Gly
    50                  55                  60

Arg Phe Thr Ile Ser Lys Thr Ser Thr Thr Val Asp Leu Arg Ile Ala
65                  70                  75                  80

Ser Pro Thr Thr Glu Asp Thr Ala Thr Tyr Phe Cys Ala Arg Asp Tyr
                85                  90                  95

Gly Asp Tyr Arg Leu Val Thr Phe Asn Ile Trp Gly Pro Gly Thr Leu
            100                 105                 110

Val Thr Val Ser Ser
        115
```

```
<210> SEQ ID NO 44
<211> LENGTH: 116
<212> TYPE: PRT
<213> ORGANISM: Artificial Sequence
<220> FEATURE:
<223> OTHER INFORMATION: Mab4 ROR1 VH

<400> SEQUENCE: 44

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65              70                  75                  80

Ser Leu Thr Thr Asp Asp Thr Ala Thr Tyr Phe Cys Ala Arg Gly Tyr
            85                  90                  95

Ser Thr Tyr Tyr Cys Asp Phe Asn Ile Trp Gly Pro Gly Thr Leu Val
            100                 105                 110

Thr Ile Ser Ser
        115

<210> SEQ ID NO 45
<211> LENGTH: 107
<212> TYPE: PRT
<213> ORGANISM: Artificial Sequence
<220> FEATURE:
<223> OTHER INFORMATION: Mab2 ROR1 VL

<400> SEQUENCE: 45

Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65              70                  75                  80

Glu Asp Met Gly Ile Tyr Tyr Cys Leu Gln Tyr Asp Glu Phe Pro Tyr
            85                  90                  95

Thr Phe Gly Gly Gly Thr Lys Leu Glu Met Lys
            100                 105

<210> SEQ ID NO 46
<211> LENGTH: 108
<212> TYPE: PRT
<213> ORGANISM: Artificial Sequence
<220> FEATURE:
<223> OTHER INFORMATION: Mab3 ROR1 VL

<400> SEQUENCE: 46

Glu Leu Val Met Thr Gln Thr Pro Ser Ser Val Ser Ala Ala Val Gly
1               5                   10                  15

Gly Thr Val Thr Ile Asn Cys Gln Ala Ser Gln Ser Ile Gly Ser Tyr
```

```
                    20                  25                  30
Leu Ala Trp Tyr Gln Gln Lys Pro Gly Gln Pro Pro Lys Leu Leu Ile
            35                  40                  45

Tyr Tyr Ala Ser Asn Leu Ala Ser Gly Val Pro Ser Arg Phe Ser Gly
        50                  55                  60

Ser Gly Ser Gly Thr Glu Tyr Thr Leu Thr Ile Ser Gly Val Gln Arg
65                  70                  75                  80

Glu Asp Ala Ala Thr Tyr Tyr Cys Leu Gly Ser Leu Ser Asn Ser Asp
                85                  90                  95

Asn Val Phe Gly Gly Gly Thr Glu Leu Glu Ile Leu
            100                 105

<210> SEQ ID NO 47
<211> LENGTH: 110
<212> TYPE: PRT
<213> ORGANISM: Artificial Sequence
<220> FEATURE:
<223> OTHER INFORMATION: Mab4 ROR1 VL

<400> SEQUENCE: 47

Glu Leu Val Met Thr Gln Thr Pro Ser Ser Thr Ser Gly Ala Val Gly
1               5                   10                  15

Gly Thr Val Thr Ile Asn Cys Gln Ala Ser Gln Ser Ile Asp Ser Asn
            20                  25                  30

Leu Ala Trp Phe Gln Gln Lys Pro Gly Gln Pro Pro Thr Leu Leu Ile
            35                  40                  45

Tyr Arg Ala Ser Asn Leu Ala Ser Gly Val Pro Ser Arg Phe Ser Gly
        50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Val Gly Asn Val Ser
                85                  90                  95

Tyr Arg Thr Ser Phe Gly Gly Gly Thr Glu Val Val Val Lys
            100                 105                 110

<210> SEQ ID NO 48
<211> LENGTH: 107
<212> TYPE: PRT
<213> ORGANISM: Artificial Sequence
<220> FEATURE:
<223> OTHER INFORMATION: Mab2 ROR1 CL

<400> SEQUENCE: 48

Arg Thr Val Ala Ala Pro Ser Val Phe Ile Phe Pro Pro Ser Asp Arg
1               5                   10                  15

Lys Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 49
<211> LENGTH: 107
<212> TYPE: PRT
<213> ORGANISM: Artificial Sequence
<220> FEATURE:
<223> OTHER INFORMATION: Mab3 ROR1 CL

<400> SEQUENCE: 49

Arg Thr Val Ala Ala Pro Ser Val Phe Ile Phe Pro Pro Ser Asp Arg
1               5                   10                  15

Lys Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 50
<211> LENGTH: 107
<212> TYPE: PRT
<213> ORGANISM: Artificial Sequence
<220> FEATURE:
<223> OTHER INFORMATION: Mab4 ROR1 CL

<400> SEQUENCE: 50

Arg Thr Val Ala Ala Pro Ser Val Phe Ile Phe Pro Pro Ser Asp Arg
1               5                   10                  15

Lys Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 51
<211> LENGTH: 103
<212> TYPE: PRT
<213> ORGANISM: Artificial Sequence
<220> FEATURE:
<223> OTHER INFORMATION: Mab2 ROR1 CH1

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
            20                  25                  30

Phe Pro Glu Pro Val Thr Val Ser Trp Asn Ser Gly Ala Leu Thr Ser 35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys
             100

<210> SEQ ID NO 52
<211> LENGTH: 103
<212> TYPE: PRT
<213> ORGANISM: Artificial Sequence
<220> FEATURE:
<223> OTHER INFORMATION: Mab3 ROR1 CH1

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys
             100

<210> SEQ ID NO 53
<211> LENGTH: 103
<212> TYPE: PRT
<213> ORGANISM: Artificial Sequence
<220> FEATURE:
<223> OTHER INFORMATION: Mab4 ROR1 CH1

<400> SEQUENCE: 53

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Glu Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Glu
                85                  90                  95

Lys Val Glu Pro Lys Ser Cys
             100

<210> SEQ ID NO 54
<211> LENGTH: 674

```
<212> TYPE: PRT
<213> ORGANISM: Artificial Sequence
<220> FEATURE:
<223> OTHER INFORMATION: Mab2 knob HC

<400> SEQUENCE: 54
```

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
    210                 215                 220

Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
            260                 265                 270

Glu Lys Pro Gly Gln Ala Phe Arg Gly Leu Ile Gly Gly Thr Asn Lys
        275                 280                 285

Arg Ala Pro Gly Thr Pro Ala Arg Phe Ser Gly Ser Leu Leu Gly Gly
    290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
            340                 345                 350

Phe Pro Leu Ala Pro Ser Ser Lys Ser Thr Ser Gly Gly Thr Ala Ala
        355                 360                 365

Leu Gly Cys Leu Val Lys Asp Tyr Phe Pro Glu Pro Val Thr Val Ser
    370                 375                 380

```
Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
            420                 425                 430

Pro Ser Asn Thr Lys Val Asp Lys Lys Val Glu Pro Lys Ser Cys Asp
        435                 440                 445

Lys Thr His Thr Cys Pro Pro Cys Pro Ala Pro Glu Ala Ala Gly Gly
    450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
            500                 505                 510

Asn Ala Lys Thr Lys Pro Arg Glu Glu Gln Tyr Asn Ser Thr Tyr Arg
        515                 520                 525

Val Val Ser Val Leu Thr Val Leu His Gln Asp Trp Leu Asn Gly Lys
    530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
            580                 585                 590

Trp Cys Leu Val Lys Gly Phe Tyr Pro Ser Asp Ile Ala Val Glu Trp
        595                 600                 605

Glu Ser Asn Gly Gln Pro Glu Asn Asn Tyr Lys Thr Thr Pro Pro Val
    610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
                645                 650                 655

Glu Ala Leu His Asn His Tyr Thr Gln Lys Ser Leu Ser Leu Ser Pro
            660                 665                 670

Gly Lys

<210> SEQ ID NO 55
<211> LENGTH: 449
<212> TYPE: PRT
<213> ORGANISM: Artificial Sequence
<220> FEATURE:
<223> OTHER INFORMATION: Mab2 hole HC

<400> SEQUENCE: 55

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
```

```
             65                  70                  75                  80
        Gln Met Ser Ser Leu Arg Ser Glu Asp Thr Ala Met Tyr Tyr Cys Gly
                         85                  90                  95

Arg Tyr Asp Tyr Asp Gly Tyr Tyr Ala Met Asp Tyr Trp Gly Gln Gly
                        100                 105                 110

Thr Ser Val Thr Val Ser Ser Ala Ser Thr Lys Gly Pro Ser Val Phe
                        115                 120                 125

Pro Leu Ala Pro Ser Ser Lys Ser Thr Ser Gly Gly Thr Ala Ala Leu
                    130                 135                 140

Gly Cys Leu Val Glu Asp Tyr Phe Pro Glu Pro Val Thr Val Ser Trp
        145                 150                 155                 160

Asn Ser Gly Ala Leu Thr Ser Gly Val His Thr Phe Pro Ala Val Leu
                        165                 170                 175

Gln Ser Ser Gly Leu Tyr Ser Leu Ser Ser Val Val Thr Val Pro Ser
                        180                 185                 190

Ser Ser Leu Gly Thr Gln Thr Tyr Ile Cys Asn Val Asn His Lys Pro
                    195                 200                 205

Ser Asn Thr Lys Val Asp Glu Lys Val Glu Pro Lys Ser Cys Asp Lys
        210                 215                 220

Thr His Thr Cys Pro Pro Cys Pro Ala Pro Glu Ala Ala Gly Gly Pro
        225                 230                 235                 240

Ser Val Phe Leu Phe Pro Pro Lys Pro Lys Asp Thr Leu Met Ile Ser
                        245                 250                 255

Arg Thr Pro Glu Val Thr Cys Val Val Val Asp Val Ser His Glu Asp
                        260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Thr Tyr Arg Val
                    290                 295                 300

Val Ser Val Leu Thr Val Leu His Gln Asp Trp Leu Asn Gly Lys Glu
        305                 310                 315                 320

Tyr Lys Cys Lys Val Ser Asn Lys Ala Leu Gly Ala Pro Ile Glu Lys
                        325                 330                 335

Thr Ile Ser Lys Ala Lys Gly Gln Pro Arg Glu Pro Gln Val Cys Thr
                    340                 345                 350

Leu Pro Pro Ser Arg Asp Glu Leu Thr Lys Asn Gln Val Ser Leu Ser
                    355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
        385                 390                 395                 400

Asp Ser Asp Gly Ser Phe Phe Leu Val Ser Lys Leu Thr Val Asp Lys
                        405                 410                 415

Ser Arg Trp Gln Gln Gly Asn Val Phe Ser Cys Ser Val Met His Glu
                        420                 425                 430

Ala Leu His Asn His Tyr Thr Gln Lys Ser Leu Ser Leu Ser Pro Gly
                        435                 440                 445

Lys

<210> SEQ ID NO 56
<211> LENGTH: 214
<212> TYPE: PRT
<213> ORGANISM: Artificial Sequence
<220> FEATURE:
```

<223> OTHER INFORMATION: Mab2 ROR1 LC

<400> SEQUENCE: 56

```
Asp Ile Lys Met Thr Gln Ser Pro Ser Ser Met Tyr Ala Ser Leu Gly
1               5                   10                  15

Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys Arg Thr Val Ala Ala
            100                 105                 110

Pro Ser Val Phe Ile Phe Pro Pro Ser Asp Arg Lys Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 57
<211> LENGTH: 672
<212> TYPE: PRT
<213> ORGANISM: Artificial Sequence
<220> FEATURE:
<223> OTHER INFORMATION: Mab3 ROR1 knob HC

<400> SEQUENCE: 57

```
Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser His Trp
            20                  25                  30

Met Ser Trp Val Arg Gln Ala Pro Gly Lys Gly Leu Glu Trp Ile Gly
        35                  40                  45

Ile Ile Ala Ala Ser Gly Ser Thr Tyr Tyr Ala Asn Trp Ala Lys Gly
50                  55                  60

Arg Phe Thr Ile Ser Lys Thr Ser Thr Thr Val Asp Leu Arg Ile Ala
65                  70                  75                  80

Ser Pro Thr Thr Glu Asp Thr Ala Thr Tyr Phe Cys Ala Arg Asp Tyr
                85                  90                  95

Gly Asp Tyr Arg Leu Val Thr Phe Asn Ile Trp Gly Pro Gly Thr Leu
            100                 105                 110

Val Thr Val Ser Ser Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Gly Gly Gly
    210                 215                 220

Gly Ser Gly Gly Gly Gly Ser Gln Ala Val Val Thr Gln Glu Pro Ser
225                 230                 235                 240

Leu Thr Val Ser Pro Gly Gly Thr Val Thr Leu Thr Cys Gly Ser Ser
                245                 250                 255

Thr Gly Ala Val Thr Thr Ser Asn Tyr Ala Asn Trp Val Gln Glu Lys
            260                 265                 270

Pro Gly Gln Ala Phe Arg Gly Leu Ile Gly Gly Thr Asn Lys Arg Ala
        275                 280                 285

Pro Gly Thr Pro Ala Arg Phe Ser Gly Ser Leu Leu Gly Gly Lys Ala
    290                 295                 300

Ala Leu Thr Leu Ser Gly Ala Gln Pro Glu Asp Glu Ala Glu Tyr Tyr
305                 310                 315                 320

Cys Ala Leu Trp Tyr Ser Asn Leu Trp Val Phe Gly Gly Gly Thr Lys
                325                 330                 335

Leu Thr Val Leu Ser Ser Ala Ser Thr Lys Gly Pro Ser Val Phe Pro
            340                 345                 350

Leu Ala Pro Ser Ser Lys Ser Thr Ser Gly Gly Thr Ala Ala Leu Gly
        355                 360                 365

Cys Leu Val Lys Asp Tyr Phe Pro Glu Pro Val Thr Val Ser Trp Asn
    370                 375                 380

Ser Gly Ala Leu Thr Ser Gly Val His Thr Phe Pro Ala Val Leu Gln
385                 390                 395                 400

Ser Ser Gly Leu Tyr Ser Leu Ser Ser Val Val Thr Val Pro Ser Ser
                405                 410                 415

Ser Leu Gly Thr Gln Thr Tyr Ile Cys Asn Val Asn His Lys Pro Ser
            420                 425                 430

Asn Thr Lys Val Asp Lys Lys Val Glu Pro Lys Ser Cys Asp Lys Thr
        435                 440                 445

His Thr Cys Pro Pro Cys Pro Ala Pro Glu Ala Ala Gly Gly Pro Ser
    450                 455                 460

Val Phe Leu Phe Pro Pro Lys Pro Lys Asp Thr Leu Met Ile Ser Arg
465                 470                 475                 480

Thr Pro Glu Val Thr Cys Val Val Val Asp Val Ser His Glu Asp Pro
                485                 490                 495

Glu Val Lys Phe Asn Trp Tyr Val Asp Gly Val Glu Val His Asn Ala
            500                 505                 510

Lys Thr Lys Pro Arg Glu Glu Gln Tyr Asn Ser Thr Tyr Arg Val Val
        515                 520                 525

Ser Val Leu Thr Val Leu His Gln Asp Trp Leu Asn Gly Lys Glu Tyr
    530                 535                 540
```

-continued

```
Lys Cys Lys Val Ser Asn Lys Ala Leu Gly Ala Pro Ile Glu Lys Thr
545                 550                 555                 560

Ile Ser Lys Ala Lys Gly Gln Pro Arg Glu Pro Gln Val Tyr Thr Leu
                565                 570                 575

Pro Pro Cys Arg Asp Glu Leu Thr Lys Asn Gln Val Ser Leu Trp Cys
            580                 585                 590

Leu Val Lys Gly Phe Tyr Pro Ser Asp Ile Ala Val Glu Trp Glu Ser
        595                 600                 605

Asn Gly Gln Pro Glu Asn Asn Tyr Lys Thr Thr Pro Pro Val Leu Asp
    610                 615                 620

Ser Asp Gly Ser Phe Phe Leu Tyr Ser Lys Leu Thr Val Asp Lys Ser
625                 630                 635                 640

Arg Trp Gln Gln Gly Asn Val Phe Ser Cys Ser Val Met His Glu Ala
                645                 650                 655

Leu His Asn His Tyr Thr Gln Lys Ser Leu Ser Leu Ser Pro Gly Lys
            660                 665                 670

<210> SEQ ID NO 58
<211> LENGTH: 447
<212> TYPE: PRT
<213> ORGANISM: Artificial Sequence
<220> FEATURE:
<223> OTHER INFORMATION: Mab3 ROR1 hole HC

<400> SEQUENCE: 58

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Asn Ser His Trp
                20                  25                  30

Met Ser Trp Val Arg Gln Ala Pro Gly Lys Gly Leu Glu Trp Ile Gly
            35                  40                  45

Ile Ile Ala Ala Ser Gly Ser Thr Tyr Tyr Ala Asn Trp Ala Lys Gly
        50                  55                  60

Arg Phe Thr Ile Ser Lys Thr Ser Thr Thr Val Asp Leu Arg Ile Ala
65                  70                  75                  80

Ser Pro Thr Thr Glu Asp Thr Ala Thr Tyr Phe Cys Ala Arg Asp Tyr
                85                  90                  95

Gly Asp Tyr Arg Leu Val Thr Phe Asn Ile Trp Gly Pro Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Glu Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Glu Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240
```

Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Gly Ala Pro Ile Glu Lys Thr Ile
                325                 330                 335

Ser Lys Ala Lys Gly Gln Pro Arg Glu Pro Gln Val Cys Thr Leu Pro
            340                 345                 350

Pro Ser Arg Asp Glu Leu Thr Lys Asn Gln Val Ser Leu Ser Cys Ala
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Val Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 59
<211> LENGTH: 215
<212> TYPE: PRT
<213> ORGANISM: Artificial Sequence
<220> FEATURE:
<223> OTHER INFORMATION: Mab3 ROR1 LC

<400> SEQUENCE: 59

Glu Leu Val Met Thr Gln Thr Pro Ser Ser Val Ser Ala Ala Val Gly
1               5                   10                  15

Gly Thr Val Thr Ile Asn Cys Gln Ala Ser Gln Ser Ile Gly Ser Tyr
            20                  25                  30

Leu Ala Trp Tyr Gln Gln Lys Pro Gly Gln Pro Pro Lys Leu Leu Ile
        35                  40                  45

Tyr Tyr Ala Ser Asn Leu Ala Ser Gly Val Pro Ser Arg Phe Ser Gly
    50                  55                  60

Ser Gly Ser Gly Thr Glu Tyr Thr Leu Thr Ile Ser Gly Val Gln Arg
65                  70                  75                  80

Glu Asp Ala Ala Thr Tyr Tyr Cys Leu Gly Ser Leu Ser Asn Ser Asp
                85                  90                  95

Asn Val Phe Gly Gly Gly Thr Glu Leu Glu Ile Leu Arg Thr Val Ala
            100                 105                 110

Ala Pro Ser Val Phe Ile Phe Pro Pro Ser Asp Arg Lys Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

-continued

```
Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 60
<211> LENGTH: 671
<212> TYPE: PRT
<213> ORGANISM: Artificial Sequence
<220> FEATURE:
<223> OTHER INFORMATION: Mab4 ROR1 knob HC

<400> SEQUENCE: 60

Gln Ser Val Lys Glu Ser Glu Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
                85                  90                  95

Ser Thr Tyr Tyr Cys Asp Phe Asn Ile Trp Gly Pro Gly Thr Leu Val
            100                 105                 110

Thr Ile Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Glu Lys Val Glu Pro Lys Ser Cys Asp Gly Gly Gly Gly
    210                 215                 220

Ser Gly Gly Gly Gly Ser Gln Ala Val Val Thr Gln Glu Pro Ser Leu
225                 230                 235                 240

Thr Val Ser Pro Gly Gly Thr Val Thr Leu Thr Cys Gly Ser Ser Thr
                245                 250                 255

Gly Ala Val Thr Thr Ser Asn Tyr Ala Asn Trp Val Gln Glu Lys Pro
            260                 265                 270

Gly Gln Ala Phe Arg Gly Leu Ile Gly Gly Thr Asn Lys Arg Ala Pro
        275                 280                 285

Gly Thr Pro Ala Arg Phe Ser Gly Ser Leu Leu Gly Gly Lys Ala Ala
    290                 295                 300
```

Leu Thr Leu Ser Gly Ala Gln Pro Glu Asp Glu Ala Glu Tyr Tyr Cys
305                 310                 315                 320

Ala Leu Trp Tyr Ser Asn Leu Trp Val Phe Gly Gly Gly Thr Lys Leu
            325                 330                 335

Thr Val Leu Ser Ser Ala Ser Thr Lys Gly Pro Ser Val Phe Pro Leu
        340                 345                 350

Ala Pro Ser Ser Lys Ser Thr Ser Gly Gly Thr Ala Ala Leu Gly Cys
    355                 360                 365

Leu Val Lys Asp Tyr Phe Pro Glu Pro Val Thr Val Ser Trp Asn Ser
370                 375                 380

Gly Ala Leu Thr Ser Gly Val His Thr Phe Pro Ala Val Leu Gln Ser
385                 390                 395                 400

Ser Gly Leu Tyr Ser Leu Ser Ser Val Val Thr Val Pro Ser Ser Ser
            405                 410                 415

Leu Gly Thr Gln Thr Tyr Ile Cys Asn Val Asn His Lys Pro Ser Asn
        420                 425                 430

Thr Lys Val Asp Lys Lys Val Glu Pro Lys Ser Cys Asp Lys Thr His
    435                 440                 445

Thr Cys Pro Pro Cys Pro Ala Pro Glu Ala Ala Gly Gly Pro Ser Val
450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
            485                 490                 495

Val Lys Phe Asn Trp Tyr Val Asp Gly Val Glu Val His Asn Ala Lys
        500                 505                 510

Thr Lys Pro Arg Glu Glu Gln Tyr Asn Ser Thr Tyr Arg Val Val Ser
    515                 520                 525

Val Leu Thr Val Leu His Gln Asp Trp Leu Asn Gly Lys Glu Tyr Lys
530                 535                 540

Cys Lys Val Ser Asn Lys Ala Leu Gly Ala Pro Ile Glu Lys Thr Ile
545                 550                 555                 560

Ser Lys Ala Lys Gly Gln Pro Arg Glu Pro Gln Val Tyr Thr Leu Pro
            565                 570                 575

Pro Cys Arg Asp Glu Leu Thr Lys Asn Gln Val Ser Leu Trp Cys Leu
        580                 585                 590

Val Lys Gly Phe Tyr Pro Ser Asp Ile Ala Val Glu Trp Glu Ser Asn
    595                 600                 605

Gly Gln Pro Glu Asn Asn Tyr Lys Thr Thr Pro Pro Val Leu Asp Ser
610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
            645                 650                 655

His Asn His Tyr Thr Gln Lys Ser Leu Ser Leu Ser Pro Gly Lys
        660                 665                 670

<210> SEQ ID NO 61
<211> LENGTH: 446
<212> TYPE: PRT
<213> ORGANISM: Artificial Sequence
<220> FEATURE:
<223> OTHER INFORMATION: Mab4 ROR1 hole HC

<400> SEQUENCE: 61

```
Gln Ser Val Lys Glu Ser Glu Gly Asp Leu Val Thr Pro Ala Gly Asn
  1               5                  10                  15

Leu Thr Leu Thr Cys Thr Ala Ser Gly Ser Asp Ile Asn Asp Tyr Pro
             20                  25                  30

Ile Ser Trp Val Arg Gln Ala Pro Gly Lys Gly Leu Glu Trp Ile Gly
         35                  40                  45

Phe Ile Asn Ser Gly Gly Ser Thr Trp Tyr Ala Ser Trp Val Lys Gly
     50                  55                  60

Arg Phe Thr Ile Ser Arg Thr Ser Thr Thr Val Asp Leu Lys Met Thr
 65                  70                  75                  80

Ser Leu Thr Thr Asp Asp Thr Ala Thr Tyr Phe Cys Ala Arg Gly Tyr
                 85                  90                  95

Ser Thr Tyr Tyr Cys Asp Phe Asn Ile Trp Gly Pro Gly Thr Leu Val
             100                 105                 110

Thr Ile Ser Ser Ala Ser Thr Lys Gly Pro Ser Val Phe Pro Leu Ala
         115                 120                 125

Pro Ser Ser Lys Ser Thr Ser Gly Gly Thr Ala Ala Leu Gly Cys Leu
 130                 135                 140

Val Glu Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                 165                 170                 175

Gly Leu Tyr Ser Leu Ser Ser Val Val Thr Val Pro Ser Ser Ser Leu
             180                 185                 190

Gly Thr Gln Thr Tyr Ile Cys Asn Val Asn His Lys Pro Ser Asn Thr
         195                 200                 205

Lys Val Asp Glu Lys Val Glu Pro Lys Ser Cys Asp Lys Thr His Thr
 210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                 245                 250                 255

Glu Val Thr Cys Val Val Val Asp Val Ser His Glu Asp Pro Glu Val
             260                 265                 270

Lys Phe Asn Trp Tyr Val Asp Gly Val Glu Val His Asn Ala Lys Thr
         275                 280                 285

Lys Pro Arg Glu Glu Gln Tyr Asn Ser Thr Tyr Arg Val Val Ser Val
 290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                 325                 330                 335

Lys Ala Lys Gly Gln Pro Arg Glu Pro Gln Val Cys Thr Leu Pro Pro
             340                 345                 350

Ser Arg Asp Glu Leu Thr Lys Asn Gln Val Ser Leu Ser Cys Ala Val
         355                 360                 365

Lys Gly Phe Tyr Pro Ser Asp Ile Ala Val Glu Trp Glu Ser Asn Gly
 370                 375                 380

Gln Pro Glu Asn Asn Tyr Lys Thr Thr Pro Pro Val Leu Asp Ser Asp
385                 390                 395                 400

Gly Ser Phe Phe Leu Val Ser Lys Leu Thr Val Asp Lys Ser Arg Trp
                 405                 410                 415

Gln Gln Gly Asn Val Phe Ser Cys Ser Val Met His Glu Ala Leu His
```

```
                    420               425               430
Asn His Tyr Thr Gln Lys Ser Leu Ser Leu Ser Pro Gly Lys
        435               440               445

<210> SEQ ID NO 62
<211> LENGTH: 217
<212> TYPE: PRT
<213> ORGANISM: Artificial Sequence
<220> FEATURE:
<223> OTHER INFORMATION: Mab4 ROR1 LC

<400> SEQUENCE: 62

Glu Leu Val Met Thr Gln Thr Pro Ser Ser Thr Ser Gly Ala Val Gly
1               5                   10                  15

Gly Thr Val Thr Ile Asn Cys Gln Ala Ser Gln Ser Ile Asp Ser Asn
            20                  25                  30

Leu Ala Trp Phe Gln Gln Lys Pro Gly Gln Pro Pro Thr Leu Leu Ile
        35                  40                  45

Tyr Arg Ala Ser Asn Leu Ala Ser Gly Val Pro Ser Arg Phe Ser Gly
    50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Val Gly Asn Val Ser
                85                  90                  95

Tyr Arg Thr Ser Phe Gly Gly Thr Glu Val Val Val Lys Arg Thr
            100                 105                 110

Val Ala Ala Pro Ser Val Phe Ile Phe Pro Pro Ser Asp Arg Lys Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 63
<211> LENGTH: 207
<212> TYPE: PRT
<213> ORGANISM: Homo sapiens

<400> SEQUENCE: 63

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80
```

-continued

```
His Leu Ser Leu Lys Glu Phe Ser Glu Leu Glu Gln Ser Gly Tyr Tyr
                 85              90              95

Val Cys Tyr Pro Arg Gly Ser Lys Pro Glu Asp Ala Asn Phe Tyr Leu
            100             105             110

Tyr Leu Arg Ala Arg Val Cys Glu Asn Cys Met Glu Met Asp Val Met
        115             120             125

Ser Val Ala Thr Ile Val Ile Val Asp Ile Cys Ile Thr Gly Gly Leu
        130             135             140

Leu Leu Leu Val Tyr Tyr Trp Ser Lys Asn Arg Lys Ala Lys Ala Lys
145             150             155             160

Pro Val Thr Arg Gly Ala Gly Ala Gly Gly Arg Gln Arg Gly Gln Asn
            165             170             175

Lys Glu Arg Pro Pro Val Pro Asn Pro Asp Tyr Glu Pro Ile Arg
            180             185             190

Lys Gly Gln Arg Asp Leu Tyr Ser Gly Leu Asn Gln Arg Arg Ile
            195             200             205
```